(12) United States Patent
Eriksson et al.

(10) Patent No.: US 7,807,878 B2
(45) Date of Patent: Oct. 5, 2010

(54) TRANSGENIC TREES EXHIBITING INCREASED GROWTH, BIOMASS PRODUCTION AND XYLEM FIBRE LENGTH, AND METHODS FOR THEIR PRODUCTION

(75) Inventors: Maria Eriksson, Umeå (SE); Thomas Moritz, Umeå (SE); Maria Israelsson, San Diego, CA (US); Oloff Olsson, Göteborg (SE)

(73) Assignee: SweTree Technologies AB, Umea (SE)

( * ) Notice: Subject to any disclaimer, the term of this patent is extended or adjusted under 35 U.S.C. 154(b) by 519 days.

(21) Appl. No.: 11/590,211

(22) Filed: Oct. 30, 2006

(65) Prior Publication Data

US 2007/0061924 A1 Mar. 15, 2007

Related U.S. Application Data

(63) Continuation-in-part of application No. 10/221,296, filed as application No. PCT/SE01/00451 on Mar. 2, 2001, now Pat. No. 7,141,422.

(60) Provisional application No. 60/240,319, filed on Oct. 13, 2000.

(30) Foreign Application Priority Data

Mar. 7, 2000 (SE) .................................... 0000751

(51) Int. Cl.
C12N 15/82 (2006.01)
C12N 5/04 (2006.01)
A01H 5/00 (2006.01)
A01H 5/10 (2006.01)

(52) U.S. Cl. ........................ 800/298; 800/290; 800/278; 800/287; 435/419

(58) Field of Classification Search ........................ None
See application file for complete search history.

(56) References Cited

U.S. PATENT DOCUMENTS 5,939,539 A * 8/1999 Lange et al. ................ 536/23.2

FOREIGN PATENT DOCUMENTS

WO WO-94/28141 12/1994

OTHER PUBLICATIONS

Eriksson (2005, NCBI Accession No. CAC00709).*
Huang et al (1998, Plant Physiology 118:773-781).*
Walden, R. et al. (1995). "Gene-transfer and Plant-Regeneration Techniques." Trends in Biotechnology 13:324-331.
Ahuja, M. R. et al. eds. (1996). Somatic Cell Genetics and Molecular Genetics of Trees. Kluwer Academic Publishers: Netherlands, pp. 89-96.
Huang, S. et al. (1998). "Overexpression of 20-Oxidase Confers a Gibberellin-Overproduction Phenotype in Arabidopsis," Plant Physiology. 118:773-781.
Fladung, M. (Sep. 22-25, 1999) "Transgenic Trees for a Better World?," Proceedings of the Internal Congress-Application of Biotechnology to Forest Genetics BioFor '99, Vitoria-Gasteiz, Spain, pp. 339-345.
Coles, J. P. et al. (1999). "Modification of Gibberellin Production and Plant Development in Arabidopsis by Sense and Antisense Expression of Gibberellin 20-Oxidase Genes," The Plant Journal 17(5): 547-556.
Ellis, D. et al. (2001) "Transgenic Trees: Where are We Now?," Proceedings of the First International Symposium on Ecological and Societal Aspects of Transgenic Plantations, Oregon State University, 2001, pp. 113-123.
Eriksson, M. E. et al. (2000). "Increased gibberellin biosynthesis in transgenic trees promotes growth, biomass production and xylem fiber length," Nature Biotechnology 18:784-788.

* cited by examiner

Primary Examiner—Stuart F. Baum
(74) Attorney, Agent, or Firm—Morrison & Foerster LLP

(57) ABSTRACT

Important aims in nearly all tree-breeding programs around the world are to produce plants with increased growth rates and stem volumes, and shorter rotation times. Such trees would yield more biomass per area unit. Here the present inventors have shown that when over-expressing a key regulatory gene in the biosynthesis of the plant hormone gibberellin (GA) in hybrid aspen (Populus tremula×P. tremuloides), improvements in valuable traits such as growth rate and biomass are obtained. In addition, these trees also have longer xylem fibres than unmodified wild type plants. Long fibers are very desirable in the production of strong paper, but it has not (as yet) proved possible to influence this trait by traditional breeding techniques. A further advantage of the present invention is that it may reduce or eliminate the use of growth influencing chemicals in forestry.

23 Claims, 6 Drawing Sheets

SEQUENCE LISTING

<160> NUMBER OF SEQ ID NOS: 73

<210> SEQ ID NO 1
<211> LENGTH: 373
<212> TYPE: PRT
<213> ORGANISM: Fragaria x ananassa

<400> SEQUENCE: 1

```
Met Ala Val Gly Cys Met Lys Thr Leu Ser His His Lys Glu Asp Asp
  1               5                  10                  15

Gln Lys Pro Leu Val Phe Asp Ala Ser Leu Leu Arg Tyr Glu Thr Asp
             20                  25                  30

Ile Pro Lys Gln Phe Ile Trp Pro Asp Asp Glu Lys Pro Cys Pro Asn
         35                  40                  45

Thr Arg Glu Leu Gln Val Pro Leu Ile Asp Leu Gly Asp Phe Leu Ser
     50                  55                  60

Gly Asn Pro Glu Ala Ala Met Lys Ala Ser Arg Leu Val Gly Glu Ala
 65                  70                  75                  80

Cys Glu Lys His Gly Phe Phe Leu Val Val Asn His Arg Val Lys Glu
                 85                  90                  95

Ser Leu Ile Ala Asp Ala His Gln Tyr Met Asp Glu Phe Phe Gly Leu
            100                 105                 110

Pro Leu Ser Glu Lys Gln Arg Thr Gln Arg Lys Ala Gly Glu His Cys
        115                 120                 125

Gly Tyr Ala Ser Ser Phe Thr Gly Arg Phe Ser Ser Lys Leu Pro Trp
130                 135                 140

Lys Glu Thr Leu Ser Phe Ser Tyr Thr Ala Asp Gln Ser Ser Ser Asn
145                 150                 155                 160

Val Val Lys Asp Tyr Leu Cys Asn Ala Met Gly Glu Glu Phe Asp Glu
                165                 170                 175

Phe Gly Arg Val Tyr Gln Asp Tyr Ser Glu Ala Met Ser Thr Leu Ser
            180                 185                 190

Ile Gly Ile Met Glu Leu Leu Gly Met Ser Leu Gly Val Gly Arg Thr
        195                 200                 205

His Phe Lys Glu Phe Phe Gly Asp Asn Asp Ser Ile Met Arg Leu Asn
210                 215                 220

Tyr Tyr Pro Pro Cys Gln Lys Pro Asp Gln Thr Leu Gly Thr Gly Pro
225                 230                 235                 240

His Cys Asp Pro Thr Ser Leu Thr Ile Leu His Gln Asp Gln Val Gly
                245                 250                 255

Gly Pro Glu Val Phe Val Asp Glu Glu Trp Arg Ser Ile Ser Pro Asn
            260                 265                 270

Leu Asn Ala Phe Val Val Asn Ile Gly Asp Ala Phe Met Ala Leu Ser
        275                 280                 285

Asn Gly Arg Tyr Lys Ser Cys Leu His Arg Ala Val Val Asn Ser Lys
290                 295                 300

Thr Pro Arg Lys Ser Leu Ala Phe Phe Leu Cys Pro Lys Asp Asp Lys
305                 310                 315                 320

Val Val Lys Pro Pro Arg Glu Leu Ile Asp Ser Ser Tyr Pro Arg Ile
                325                 330                 335

Tyr Pro Asp Phe Thr Trp Pro Met Leu Leu Glu Phe Thr Gln Lys His
            340                 345                 350

Tyr Arg Ala Asp Met Lys Thr Leu Gln Ala Phe Thr Asn Trp Leu Gln
        355                 360                 365

Glu Gln Arg Ser Ser
    370
```

<210> SEQ ID NO 2
<211> LENGTH: 392
<212> TYPE: PRT
<213> ORGANISM: Malus x domestica

<400> SEQUENCE: 2

```
Met Ala Val Glu Cys Met Ile Lys Pro Ser Ser Leu Gln Thr Met Thr
 1               5                  10                  15
Gln Pro Pro Ser Pro Lys Thr Gln Gln Thr Gln Gln His Lys Glu Asp
             20                  25                  30
Asp Gln Lys Pro Leu Val Phe Asp Ala Ser Val Phe Arg Tyr Gln Thr
         35                  40                  45
Glu Ile Pro Ser Gln Phe Ile Trp Pro Asp His Glu Lys Pro Cys Lys
     50                  55                  60
Asn Thr Pro Glu Leu Gln Val Ala Leu Ile Asp Leu Gly Gly Phe Leu
 65                  70                  75                  80
Ser Gly Asp Lys Glu Ala Val Ala Lys Ala Ser Gln Leu Val Gly Glu
                 85                  90                  95
Ala Cys Gln Lys His Gly Phe Phe Leu Ile Val Asn His Gly Val Asp
            100                 105                 110
Asn Lys Leu Ile Ala Asp Ala His Cys Tyr Met Asp Asp Phe Phe Gly
        115                 120                 125
Met Pro Leu Ser Glu Lys Gln Arg Ala Glu Arg Lys Ala Gly Glu Ser
    130                 135                 140
Cys Gly Tyr Ala Ser Ser Phe Thr Gly Arg Phe Ser Ser Lys Leu Pro
145                 150                 155                 160
Trp Lys Glu Thr Leu Ser Phe Ser Tyr Ser Ala Glu Lys Gly Ser Thr
                165                 170                 175
Asn Phe Ile Gln Asp Tyr Phe Cys Asp Lys Met Gly Glu Glu Phe Lys
            180                 185                 190
Glu Phe Gly Arg Val Tyr Gln Asp Tyr Cys Lys Ala Met Ser Thr Leu
        195                 200                 205
Ser Ile Gly Ile Met Glu Leu Leu Gly Leu Ser Leu Gly Val Asp Arg
    210                 215                 220
Ala Tyr Phe Lys Glu Phe Phe Glu Asp Asn Asn Ser Ile Met Arg Leu
225                 230                 235                 240
Asn Tyr Tyr Pro Pro Cys Gln Arg Pro Glu Gln Thr Leu Gly Thr Gly
                245                 250                 255
Pro His Cys Asp Pro Thr Ala Leu Thr Ile Leu His Gly Asp Gln Val
            260                 265                 270
Gly Gly Leu Glu Val Phe Val Asp Asp Gln Trp His Ser Val Thr Pro
        275                 280                 285
Asn Leu Asn Ala Phe Val Val Asn Ile Gly Asp Thr Phe Met Ala Leu
    290                 295                 300
Ser Asn Gly Lys Tyr Lys Ser Gly Leu His Arg Ala Val Val Asn Ser
305                 310                 315                 320
Glu Thr Pro Arg Lys Ser Leu Ala Phe Phe Leu Cys Pro Arg Asp Asp
                325                 330                 335
Lys Val Val Lys Pro Pro Ser Gly Leu Val Asp Thr Ser Ser Pro Arg
            340                 345                 350
Lys Tyr Pro Asp Phe Thr Trp Ser Met Leu Leu Glu Phe Thr Met Lys
        355                 360                 365
His Tyr Arg Ala Asp Met Lys Thr Leu Gln Val Phe Ser Asn Trp Val
    370                 375                 380
Gln Gln Lys Ser Asn Gln Lys Leu
385                 390
```

<210> SEQ ID NO 3
<211> LENGTH: 386
<212> TYPE: PRT
<213> ORGANISM: Cucurbita maxima

<400> SEQUENCE: 3

```
Met Ala Leu Asn Gly Lys Val Ala Thr Glu Ser Ala Pro Ser Asn Leu
  1               5                  10                  15

Asn Glu Glu Met Lys Gly Glu Tyr Arg Pro Pro Phe Gly Gly Ser Asp
             20                  25                  30

Glu Ser Lys Val Pro Glu Asp Phe Ile Trp Ser Glu Lys Phe Glu Ala
         35                  40                  45

Ser Glu Leu Leu Pro Val Leu Asp Val Pro Thr Ile Asp Leu Glu Lys
 50                  55                  60

Phe Met Ser Gly Asp Lys Ser Tyr Val Glu Ala Thr Arg Leu Val
 65                  70                  75                  80

Asp Glu Ala Cys Arg Gln His Gly Ile Phe Phe Val Val Asn His Gly
                 85                  90                  95

Val Asp Ile Glu Met Met Gly Arg Val His Asp Cys Met Asn Glu Phe
            100                 105                 110

Phe Thr Met Pro Leu Asp Val Lys Gln Arg Ala Lys Arg Lys Val Gly
            115                 120                 125

Glu Ser Tyr Gly Tyr Thr Asn Ser Phe Phe Gly Arg Phe Ala Ser Asn
        130                 135                 140

Leu Pro Trp Lys Glu Thr Phe Ser Leu Arg Cys Val Ala Ala Gln Asn
145                 150                 155                 160

Ser Ser Ala Ala His Asp Tyr Val Leu Asp Thr Leu Gly Ser Ser Phe
                165                 170                 175

Ser His His Gly Lys Ala Tyr Gln Glu Cys Gly Ile Ala Leu Asn Glu
            180                 185                 190

Leu Gly Thr Lys Ile Val Glu Leu Leu Gly Leu Ser Leu Gly Ile Ser
        195                 200                 205

Arg Glu Tyr Phe Lys Asn Phe Tyr Lys Asp Asn Asp Ser Ile Leu Arg
    210                 215                 220

Leu Asn Tyr Tyr Pro Thr Cys Asp Lys Pro Glu Val Val Leu Gly Thr
225                 230                 235                 240

Gly Pro His Thr Asp Pro Thr Ser Val Thr Ile Leu His Gln Asp Pro
                245                 250                 255

Val Ser Gly Leu Gln Val Cys Ser Asn Asp Gln Trp His Ser Val Thr
            260                 265                 270

Pro Asn Leu Asn Ala Phe Val Val Asn Ile Gly Asp Thr Phe Met Ala
        275                 280                 285

Leu Ser Asn Gly Lys Tyr Lys Ser Gly Leu His Arg Ala Val Val Asn
290                 295                 300

Ser Glu Thr Pro Arg Lys Ser Leu Ala Phe Phe Leu Cys Pro Arg Asp
305                 310                 315                 320

Asp Lys Val Val Lys Pro Pro Ser Gly Leu Val Asp Thr Ser Ser Pro
                325                 330                 335

Arg Lys Tyr Pro Asp Phe Thr Trp Ser Met Leu Leu Glu Phe Thr Met
            340                 345                 350

Lys His Tyr Arg Pro Ala Cys Asn Thr Leu Glu Ala Phe Lys Thr Trp
        355                 360                 365

Val Gln Glu Gly Lys Ala Leu Asp Thr Gly Ser Thr Ile Thr Ala Pro
    370                 375                 380
```

Ser Ala
385

<210> SEQ ID NO 4
<211> LENGTH: 386
<212> TYPE: PRT
<213> ORGANISM: Cucurbita maxima

<400> SEQUENCE: 4

```
Met Ala Leu Asn Gly Lys Val Ala Thr Glu Ser Ala Pro Ser Asn Leu
 1               5                  10                  15
Asn Glu Glu Met Lys Gly Glu Tyr Arg Pro Pro Phe Gly Gly Ser Asp
            20                  25                  30
Glu Ser Lys Val Pro Glu Asp Phe Ile Trp Ser Glu Lys Phe Glu Ala
        35                  40                  45
Ser Glu Leu Leu Pro Val Leu Asp Val Pro Thr Ile Asp Leu Glu Lys
    50                  55                  60
Phe Met Ser Gly Asp Lys Ser Tyr Val Glu Ala Thr Arg Leu Val
65                  70                  75                  80
Asp Glu Ala Cys Arg Gln His Gly Ile Phe Phe Val Val Asn His Gly
                85                  90                  95
Val Asp Ile Glu Met Met Gly Arg Val His Asp Cys Met Asn Glu Phe
            100                 105                 110
Phe Thr Met Pro Leu Asp Val Lys Gln Arg Ala Lys Arg Lys Val Gly
        115                 120                 125
Glu Ser Tyr Gly Tyr Thr Asn Ser Phe Phe Gly Arg Phe Ala Ser Asn
    130                 135                 140
Leu Pro Trp Lys Glu Thr Phe Ser Leu Arg Cys Val Ala Ala Gln Asn
145                 150                 155                 160
Ser Ser Ala Ala His Asp Tyr Val Leu Asp Thr Leu Gly Pro Ser Phe
                165                 170                 175
Ser His His Gly Lys Ala Tyr Gln Glu Cys Gly Ile Ala Leu Asn Glu
            180                 185                 190
Leu Gly Thr Lys Ile Val Glu Leu Leu Gly Leu Ser Leu Gly Ile Ser
        195                 200                 205
Arg Glu Tyr Phe Lys Asn Phe Phe Glu Asp Asn Asp Ser Ile Leu Arg
    210                 215                 220
Leu Asn Tyr Tyr Pro Thr Cys Asp Lys Pro Glu Val Val Leu Gly Thr
225                 230                 235                 240
Gly Pro His Thr Asp Pro Thr Ser Val Thr Ile Leu His Gln Asp Pro
                245                 250                 255
Val Ser Gly Leu Gln Val Cys Ser Asn Asp Gln Trp Tyr Ser Ile Pro
            260                 265                 270
Pro Asn Pro Glu Ala Phe Val Ile Asn Ile Gly Asp Thr Phe Thr Ser
        275                 280                 285
Leu Thr Asn Gly Ile Tyr Lys Gly Cys Ile His Arg Ala Val Val Asn
    290                 295                 300
Ser Met Asn Ala Arg Lys Ser Leu Ala Phe Phe Leu Cys Pro Ser His
305                 310                 315                 320
Asp Lys Val Val Arg Ala Pro Glu Glu Leu Val Glu Lys Ser Pro Pro
                325                 330                 335
Arg Lys Tyr Pro Asp Tyr Lys Trp Pro Met Leu Leu Glu Met Thr Gln
            340                 345                 350
Lys Arg Tyr Arg Pro Asp Cys Asn Thr Leu Glu Ala Phe Lys Thr Trp
        355                 360                 365
```

```
Val Gln Glu Gly Lys Ala Leu Asp Thr Gly Ser Thr Ile Thr Ala Pro
        370                 375                 380

Ser Ala
385

<210> SEQ ID NO 5
<211> LENGTH: 378
<212> TYPE: PRT
<213> ORGANISM: Cucurbita maxima

<400> SEQUENCE: 5

Met His Val Val Thr Ser Thr Pro Glu Ala Arg His Asp Gly Ala Pro
  1               5                  10                  15

Leu Val Phe Asp Ala Ser Val Leu Arg His Gln His Asn Ile Pro Lys
             20                  25                  30

Gln Phe Ile Trp Pro Asp Glu Lys Pro Ala Ala Thr Cys Pro Glu
         35                  40                  45

Leu Glu Val Pro Leu Ile Asp Leu Ser Gly Phe Leu Ser Gly Glu Lys
 50                  55                  60

Asp Ala Ala Glu Ala Val Arg Leu Val Gly Glu Ala Cys Glu Lys
 65                  70                  75                  80

His Gly Phe Phe Leu Val Val Asn His Gly Val Asp Arg Lys Leu Ile
                 85                  90                  95

Gly Glu Ala His Lys Tyr Met Asp Glu Phe Phe Glu Leu Pro Leu Ser
            100                 105                 110

Gln Lys Gln Ser Ala Gln Arg Lys Ala Gly Glu His Cys Gly Tyr Ala
        115                 120                 125

Ser Ser Phe Thr Gly Arg Phe Ser Ser Lys Leu Pro Trp Lys Glu Thr
    130                 135                 140

Leu Ser Phe Arg Phe Ala Ala Asp Glu Ser Leu Asn Asn Leu Val Leu
145                 150                 155                 160

His Tyr Leu Asn Asp Lys Leu Gly Asp Gln Phe Ala Lys Phe Gly Arg
                165                 170                 175

Val Tyr Gln Asp Tyr Cys Glu Ala Met Ser Gly Leu Ser Leu Gly Ile
            180                 185                 190

Met Glu Leu Leu Gly Lys Ser Leu Gly Val Glu Glu Gln Cys Phe Lys
        195                 200                 205

Asn Phe Phe Lys Asp Asn Asp Ser Ile Met Arg Leu Asn Phe Tyr Pro
    210                 215                 220

Pro Cys Gln Lys Pro His Leu Thr Leu Gly Thr Gly Pro His Cys Asp
225                 230                 235                 240

Pro Thr Ser Leu Thr Ile Leu His Gln Asp Gln Val Gly Gly Leu Gln
                245                 250                 255

Val Phe Val Asp Asn Gln Trp Arg Leu Ile Thr Pro Asn Phe Asp Ala
            260                 265                 270

Phe Val Val Asn Ile Gly Asp Thr Phe Met Ala Leu Ser Asn Gly Arg
        275                 280                 285

Tyr Lys Ser Cys Leu His Arg Ala Val Val Asn Ser Glu Arg Thr Arg
    290                 295                 300

Lys Ser Leu Ala Phe Phe Leu Cys Pro Arg Asn Asp Lys Val Val Arg
305                 310                 315                 320

Pro Pro Arg Glu Leu Val Asp Thr Gln Asn Pro Arg Arg Tyr Pro Asp
                325                 330                 335

Phe Thr Trp Ser Met Leu Leu Arg Phe Thr Gln Thr His Tyr Arg Ala
```

-continued

```
                340                 345                 350
Asp Met Lys Thr Leu Glu Ala Phe Ser Ala Trp Leu Gln Gln Glu Gln
        355                 360                 365

Gln Glu Gln Gln Glu Gln Gln Phe Asn Ile
    370                 375

<210> SEQ ID NO 6
<211> LENGTH: 379
<212> TYPE: PRT
<213> ORGANISM: Marah macrocarpus

<400> SEQUENCE: 6

Met Ala Ile Thr Cys Met Met Ala Thr Glu Ser Ser Pro Ala Glu Glu
1               5                   10                  15

Val Lys Arg Glu His Gln Val Ala Phe Gly Gly Ala Gly Glu Ser Ser
            20                  25                  30

Val Pro Glu Asn Phe Ile Trp Pro Asp Glu Phe Lys Ala Thr Ala Asp
        35                  40                  45

Ala Pro Glu Leu His Val Pro His Ile Asp Leu Lys Lys Val Leu Ser
    50                  55                  60

Gly Asp Glu Lys Asp Val Glu Glu Ala Thr Arg Leu Val Asp Glu Ala
65                  70                  75                  80

Cys Arg Lys His Gly Phe Phe Val Val Asn His Gly Val Asp Lys
                85                  90                  95

Glu Leu Met Asn Lys Val His Glu Cys Met Asn Glu Phe Phe Thr Leu
            100                 105                 110

Pro Leu Asp Val Lys Gln Lys Ala His Arg Lys Val Gly Glu Asn Phe
        115                 120                 125

Gly Tyr Ala Asn Ser Phe Ile Gly Arg Phe Ser Thr Lys Leu Pro Trp
    130                 135                 140

Lys Glu Thr Phe Ser Leu Arg Tyr Leu Ala His Glu Asn Ser Ser Thr
145                 150                 155                 160

Ala Arg Asp Tyr Val Ser Gln Val Leu Gly Pro Glu Phe Ser His His
                165                 170                 175

Gly Glu Val Tyr Gln Glu Cys Gly Lys Ala Leu Ser Asp Leu Ser Leu
            180                 185                 190

Arg Ile Val Glu Leu Leu Gly Leu Ser Leu Gly Ile Ser Arg Glu Thr
        195                 200                 205

Phe Arg Lys Phe Tyr Glu Asp Asn Asp Ser Ile Met Arg Met Asn Tyr
    210                 215                 220

Tyr Pro Arg Cys Glu Lys Pro Glu Leu Thr Leu Gly Thr Gly Pro His
225                 230                 235                 240

Cys Asp Pro Thr Ser Ile Thr Ile Leu His Gln Asp Asp Val Ser Gly
                245                 250                 255

Leu Gln Val Tyr Val Asp Asp Gln Trp His Ser Ile Pro Pro Thr Glu
            260                 265                 270

Asp Ser Phe Val Val Asn Val Gly Asp Thr Phe Met Ser Leu Thr Asn
        275                 280                 285

Gly Val Tyr Lys Ser Cys Phe His Arg Ala Val Val Asn Cys Lys Glu
    290                 295                 300

Ala Arg Lys Ser Met Ala Phe Phe Leu Cys Pro Ala Val Glu Lys Val
305                 310                 315                 320

Val Arg Ala Pro Glu Glu Leu Val Glu Lys Tyr Pro Pro Arg Lys Phe
                325                 330                 335
```

```
Pro Asp Tyr Thr Trp Pro Met Leu Leu Glu Met Thr Gln Lys Tyr Tyr
            340                 345                 350

Arg Ala Asp Ser Asn Thr Phe Asn Ala Phe Thr Thr Trp Ile Gln Gln
            355                 360                 365

Gln Asn Leu Asp Ser Thr Ala Ser Pro Ala Val
            370                 375

<210> SEQ ID NO 7
<211> LENGTH: 379
<212> TYPE: PRT
<213> ORGANISM: Citrullus lanatus

<400> SEQUENCE: 7

Met Ala Met Lys Cys Met Met Ser Thr Gly Glu Ser Lys Glu Met Lys
 1                5                  10                  15

Ser Lys Leu His Arg Val Glu Phe Gly Cys Ser Glu Glu Ser Met Val
            20                  25                  30

Pro Glu Asn Phe Val Trp Pro Asp Glu Phe Lys Ala Lys Asp Gly Ala
            35                  40                  45

Pro Glu Leu His Val Pro His Ile Asp Leu His Lys Phe Leu Asn Gly
            50                  55                  60

Asn Glu Ser Asp Ile Glu Ala Thr Arg Leu Val Asp Glu Ala Cys
65                  70                  75                  80

Arg Lys His Gly Phe Phe Val Leu Val Asn His Gly Val Asp Met Glu
                85                  90                  95

Leu Ile Lys Gly Val His Glu Cys Met Asp Glu Phe Phe Thr Leu Pro
            100                 105                 110

Phe Asp Val Lys Gln Lys Ser Gln Arg Lys Phe Gly Glu Asn Tyr Gly
            115                 120                 125

Tyr Ala Asn Ser Phe Ile Gly Arg Phe Ser Asn Asn Leu Pro Trp Lys
130                 135                 140

Glu Thr Leu Ser Leu Pro Tyr Val Ala Asn His Asn Ser Thr Ser Val
145                 150                 155                 160

Gln Asp Phe Val Ser Lys Cys Val Gly Pro Glu Leu Ser His Gln Gly
                165                 170                 175

Lys Val Tyr Gln Glu Cys Gly Lys Ala Leu Ser Asp Leu Ser Leu Lys
            180                 185                 190

Ile Val Glu Leu Leu Gly Leu Ser Leu Gly Val Pro Lys Glu Lys Phe
            195                 200                 205

Lys Lys Phe Tyr Glu Asp Asn Asp Ser Ile Ile Arg Leu Asn Tyr Tyr
210                 215                 220

Pro Pro Cys Glu Lys Pro Glu Leu Thr Leu Gly Thr Gly Pro His Cys
225                 230                 235                 240

Asp Pro Thr Ser Ile Thr Ile Leu His Gln Asp His Val Ser Gly Leu
                245                 250                 255

Gln Val Tyr Val Asp Asp Glu Trp His Ser Ile Pro Thr Lys Asp
            260                 265                 270

Ser Phe Val Ile Asn Ile Gly Asp Thr Phe Met Ala Leu Thr Asn Gly
            275                 280                 285

Val Tyr Lys Ser Cys Phe His Arg Ala Val Asn Cys Lys Glu Val
            290                 295                 300

Arg Lys Ser Met Ala Phe Phe Leu Cys Pro Ala Ala Asp Lys Val Val
305                 310                 315                 320

Arg Ala Pro Asp Glu Val Val Glu Lys Asn Pro Pro Arg Lys Phe Pro
                325                 330                 335
```

```
Asp Tyr Thr Trp Pro Met Leu Leu Glu Leu Thr Gln Lys Phe Tyr Arg
            340                 345                 350

Ala Asp Ser Asn Thr Phe Gln Ala Phe Ile Pro Trp Leu Glu Lys Gln
        355                 360                 365

Lys Ser Ala Asn Thr Ile Ala Pro Pro Ala Leu
    370                 375

<210> SEQ ID NO 8
<211> LENGTH: 293
<212> TYPE: PRT
<213> ORGANISM: Arabidopsis thaliana

<400> SEQUENCE: 8

Met Asp Pro Pro Phe Asn Glu Ile Tyr Asn Asn Leu Leu Tyr Asn Gln
1               5                   10                  15

Ile Thr Lys Lys Asp Asn Asp Val Ser Glu Ile Pro Phe Ser Phe Ser
            20                  25                  30

Val Thr Ala Val Val Glu Glu Val Glu Leu Pro Val Ile Asp Val Ser
        35                  40                  45

Arg Leu Ile Asp Gly Ala Glu Glu Arg Glu Lys Cys Lys Glu Ala
50                  55                  60

Ile Ala Arg Ala Ser Arg Glu Trp Gly Phe Phe Gln Val Ile Asn His
65                  70                  75                  80

Gly Ile Ser Met Asp Val Leu Glu Lys Met Arg Gln Glu Gln Ile Arg
                85                  90                  95

Val Phe Arg Glu Pro Phe Asp Lys Lys Ser Asn Ser Thr Met Glu Lys
            100                 105                 110

Phe Ala Ser Glu Ser Glu Ala Leu Ala Tyr Met Leu Ala Glu Val Leu
        115                 120                 125

Ala Glu Lys Ser Gly Gln Asn Ser Ser Phe Lys Glu Asn Cys Val
130                 135                 140

Arg Asn Thr Cys Tyr Leu Arg Met Asn Arg Tyr Pro Pro Cys Pro Lys
145                 150                 155                 160

Pro Ser Glu Val Tyr Gly Leu Met Pro His Thr Asp Ser Asp Phe Leu
                165                 170                 175

Thr Ile Leu Tyr Gln Asp Gln Val Gly Gly Leu Gln Leu Ile Lys Asp
            180                 185                 190

Asn Arg Trp Ile Ala Val Lys Pro Asn Pro Lys Ala Leu Ile Ile Asn
        195                 200                 205

Ile Gly Asp Leu Phe Gln Ala Trp Ser Asn Gly Met Tyr Lys Ser Val
210                 215                 220

Glu His Arg Val Met Thr Asn Pro Lys Val Glu Arg Phe Ser Thr Ala
225                 230                 235                 240

Tyr Phe Met Cys Pro Ser Tyr Asp Ala Val Ile Glu Cys Ser Ser Asp
                245                 250                 255

Arg Pro Ala Tyr Arg Asn Phe Ser Phe Arg Glu Phe Arg Gln Gln Val
            260                 265                 270

Gln Glu Asp Val Lys Lys Phe Gly Phe Lys Val Gly Leu Pro Arg Phe
        275                 280                 285

Leu Asn His Val Tyr
    290

<210> SEQ ID NO 9
<211> LENGTH: 376
<212> TYPE: PRT
```

<213> ORGANISM: Arabidopsis thaliana

<400> SEQUENCE: 9

Met Glu Cys Ile Ile Lys Leu Pro Gln Arg Phe Asn Lys Asn Lys Ser
1               5                   10                  15

Lys Lys Asn Pro Leu Arg Ile Phe Asp Ser Thr Val Leu Asn His Gln
            20                  25                  30

Pro Asp His Ile Pro Gln Glu Phe Val Trp Pro Asp His Glu Lys Pro
        35                  40                  45

Ser Lys Asn Val Pro Ile Leu Gln Val Pro Val Ile Asp Leu Ala Gly
    50                  55                  60

Phe Leu Ser Asn Asp Pro Leu Leu Val Ser Glu Ala Glu Arg Leu Val
65                  70                  75                  80

Ser Glu Ala Ala Lys His Gly Phe Phe Leu Val Thr Asn His Gly
                85                  90                  95

Val Asp Glu Arg Leu Leu Ser Thr Ala His Lys Leu Met Asp Thr Phe
            100                 105                 110

Phe Lys Ser Pro Asn Tyr Glu Lys Leu Lys Ala Gln Arg Lys Val Gly
        115                 120                 125

Glu Thr Thr Gly Tyr Ala Ser Ser Phe Val Gly Arg Phe Lys Glu Asn
    130                 135                 140

Leu Pro Trp Lys Glu Thr Leu Ser Phe Ser Phe Ser Pro Thr Glu Lys
145                 150                 155                 160

Ser Glu Asn Tyr Ser Gln Thr Val Lys Asn Tyr Ile Ser Lys Thr Met
                165                 170                 175

Gly Asp Gly Tyr Lys Asp Phe Gly Ser Val Tyr Gln Glu Tyr Ala Glu
            180                 185                 190

Thr Met Ser Asn Leu Ser Leu Lys Ile Met Glu Leu Leu Gly Met Ser
        195                 200                 205

Leu Gly Ile Lys Arg Glu His Phe Arg Glu Phe Phe Glu Asp Asn Glu
    210                 215                 220

Ser Ile Phe Arg Leu Asn Tyr Tyr Pro Lys Cys Lys Gln Pro Asp Leu
225                 230                 235                 240

Val Leu Gly Thr Gly Pro His Cys Asp Pro Thr Ser Leu Thr Ile Leu
                245                 250                 255

Gln Gln Asp Gln Val Ser Gly Leu Gln Val Phe Val Asp Asn Gln Trp
            260                 265                 270

Gln Ser Ile Pro Pro Ile Pro Gln Ala Leu Val Val Asn Ile Gly Asp
        275                 280                 285

Thr Leu Met Ala Leu Thr Asn Gly Ile Tyr Lys Ser Cys Leu His Arg
    290                 295                 300

Ala Val Val Asn Gly Glu Thr Thr Arg Lys Thr Leu Ala Phe Phe Leu
305                 310                 315                 320

Cys Pro Lys Val Asp Lys Val Val Lys Pro Pro Ser Glu Leu Glu Gly
                325                 330                 335

Glu Arg Ala Tyr Pro Asp Phe Thr Trp Ser Met Phe Leu Glu Phe Thr
            340                 345                 350

Met Lys His Tyr Arg Ala Asp Met Asn Thr Leu Glu Glu Phe Thr Asn
        355                 360                 365

Trp Leu Lys Asn Lys Gly Ser Phe
    370                 375

<210> SEQ ID NO 10
<211> LENGTH: 336

```
<212> TYPE: PRT
<213> ORGANISM: Arabidopsis thaliana

<400> SEQUENCE: 10

Met Ala Ser Gln Pro Pro Phe Lys Thr Asn Phe Cys Ser Ile Phe Gly
 1               5                  10                  15

Ser Ser Phe Pro Asn Ser Thr Ser Glu Ser Asn Thr Asn Thr Ser Thr
             20                  25                  30

Ile Gln Thr Ser Gly Ile Lys Leu Pro Val Ile Asp Leu Ser His Leu
         35                  40                  45

Thr Ser Gly Glu Glu Val Lys Arg Lys Arg Cys Val Lys Gln Met Val
 50                  55                  60

Ala Ala Ala Lys Glu Trp Gly Phe Phe Gln Ile Val Asn His Gly Ile
65                  70                  75                  80

Pro Lys Asp Val Phe Glu Met Met Leu Leu Glu Lys Lys Leu Phe
                 85                  90                  95

Asp Gln Pro Phe Ser Val Lys Val Arg Glu Arg Phe Ser Asp Leu Ser
                100                 105                 110

Lys Asn Ser Tyr Arg Trp Gly Asn Pro Ser Ala Thr Ser Pro Ala Gln
            115                 120                 125

Tyr Ser Val Ser Glu Ala Phe His Ile Ile Leu Ser Glu Val Ser Arg
        130                 135                 140

Ile Ser Asp Asp Arg Asn Asn Leu Arg Thr Ile Val Glu Thr Tyr Val
145                 150                 155                 160

Gln Glu Ile Ala Arg Val Ala Gln Met Ile Cys Glu Ile Leu Gly Lys
                165                 170                 175

Gln Val Asn Val Ser Ser Glu Tyr Phe Glu Asn Ile Phe Glu Leu Glu
            180                 185                 190

Asn Ser Phe Leu Arg Leu Asn Lys Tyr His Pro Ser Val Phe Gly Ser
        195                 200                 205

Glu Val Phe Gly Leu Val Pro His Thr Asp Thr Ser Phe Leu Thr Ile
    210                 215                 220

Leu Ser Gln Asp Gln Ile Gly Gly Leu Glu Leu Glu Asn Asn Gly Gln
225                 230                 235                 240

Trp Ile Ser Val Lys Pro Cys Leu Glu Ala Leu Thr Val Asn Ile Gly
                245                 250                 255

Asp Met Phe Gln Ala Leu Ser Asn Gly Val Tyr Gln Ser Val Arg His
            260                 265                 270

Arg Val Ile Ser Pro Ala Asn Ile Glu Arg Met Ser Ile Ala Phe Phe
        275                 280                 285

Val Cys Pro Tyr Leu Glu Thr Glu Ile Asp Cys Phe Gly Tyr Pro Lys
    290                 295                 300

Lys Tyr Arg Arg Phe Ser Phe Arg Glu Tyr Lys Glu Gln Ser Glu His
305                 310                 315                 320

Asp Val Lys Glu Thr Gly Asp Lys Val Gly Leu Ser Arg Phe Leu Ile
                325                 330                 335

<210> SEQ ID NO 11
<211> LENGTH: 377
<212> TYPE: PRT
<213> ORGANISM: Arabidopsis thaliana

<400> SEQUENCE: 11

Met Ala Val Ser Phe Val Thr Thr Ser Pro Glu Glu Glu Asp Lys Pro
 1               5                  10                  15
```

```
Lys Leu Gly Leu Gly Asn Ile Gln Thr Pro Leu Ile Phe Asn Pro Ser
             20                  25                  30

Met Leu Asn Leu Gln Ala Asn Ile Pro Asn Gln Phe Ile Trp Pro Asp
         35                  40                  45

Asp Glu Lys Pro Ser Ile Asn Val Leu Glu Leu Asp Val Pro Leu Ile
     50                  55                  60

Asp Leu Gln Asn Leu Leu Ser Asp Pro Ser Ser Thr Leu Asp Ala Ser
 65                  70                  75                  80

Arg Leu Ile Ser Glu Ala Cys Lys Lys His Gly Phe Phe Leu Val Val
                 85                  90                  95

Asn His Gly Ile Ser Glu Glu Leu Ile Ser Asp Ala His Glu Tyr Thr
            100                 105                 110

Ser Arg Phe Phe Asp Met Pro Leu Ser Glu Lys Gln Arg Val Leu Arg
        115                 120                 125

Lys Ser Gly Glu Ser Val Gly Tyr Ala Ser Ser Phe Thr Gly Arg Phe
    130                 135                 140

Ser Thr Lys Leu Pro Trp Lys Glu Thr Leu Ser Phe Arg Phe Cys Asp
145                 150                 155                 160

Asp Met Ser Arg Ser Lys Ser Val Gln Asp Tyr Phe Cys Asp Ala Leu
                165                 170                 175

Gly His Gly Phe Gln Pro Phe Gly Lys Val Tyr Gln Glu Tyr Cys Glu
            180                 185                 190

Ala Met Ser Ser Leu Ser Leu Lys Ile Met Glu Leu Leu Gly Leu Ser
        195                 200                 205

Leu Gly Val Lys Arg Asp Tyr Phe Arg Glu Phe Phe Glu Glu Asn Asp
    210                 215                 220

Ser Ile Met Arg Leu Asn Tyr Tyr Pro Pro Cys Ile Lys Pro Asp Leu
225                 230                 235                 240

Thr Leu Gly Thr Gly Pro His Cys Asp Pro Thr Ser Leu Thr Ile Leu
                245                 250                 255

His Gln Asp His Val Asn Gly Leu Gln Val Phe Val Glu Asn Gln Trp
            260                 265                 270

Arg Ser Ile Arg Pro Asn Pro Lys Ala Phe Val Val Asn Ile Gly Asp
        275                 280                 285

Thr Phe Met Ala Leu Ser Asn Asp Arg Tyr Lys Ser Cys Leu His Arg
    290                 295                 300

Ala Val Val Asn Ser Glu Ser Glu Arg Lys Ser Leu Ala Phe Phe Leu
305                 310                 315                 320

Cys Pro Lys Lys Asp Arg Val Val Thr Pro Arg Glu Leu Leu Asp
                325                 330                 335

Ser Ile Thr Ser Arg Arg Tyr Pro Asp Phe Thr Trp Ser Met Phe Leu
        340                 345                 350

Glu Phe Thr Gln Lys His Tyr Arg Ala Asp Met Asn Thr Leu Gln Ala
    355                 360                 365

Phe Ser Asp Trp Leu Thr Lys Pro Ile
370                 375

<210> SEQ ID NO 12
<211> LENGTH: 380
<212> TYPE: PRT
<213> ORGANISM: Arabidopsis thaliana

<400> SEQUENCE: 12

Met Ala Thr Glu Cys Ile Ala Thr Val Pro Gln Ile Phe Ser Glu Asn
 1               5                  10                  15
```

Lys Thr Lys Glu Asp Ser Ser Ile Phe Asp Ala Lys Leu Leu Asn Gln
            20                  25                  30

His Ser His His Ile Pro Gln Gln Phe Val Trp Pro Asp His Glu Lys
        35                  40                  45

Pro Ser Thr Asp Val Gln Pro Leu Gln Val Pro Leu Ile Asp Leu Ala
    50                  55                  60

Gly Phe Leu Ser Gly Asp Ser Cys Leu Ala Ser Glu Ala Thr Arg Leu
65                  70                  75                  80

Val Ser Lys Ala Ala Thr Lys His Gly Phe Phe Leu Ile Thr Asn His
                85                  90                  95

Gly Val Asp Glu Ser Leu Leu Ser Arg Ala Tyr Leu His Met Asp Ser
            100                 105                 110

Phe Phe Lys Ala Pro Ala Cys Glu Lys Gln Lys Ala Gln Arg Lys Trp
        115                 120                 125

Gly Glu Ser Ser Gly Tyr Ala Ser Ser Phe Val Gly Arg Phe Ser Ser
    130                 135                 140

Lys Leu Pro Trp Lys Glu Thr Leu Ser Phe Lys Phe Ser Pro Glu Glu
145                 150                 155                 160

Lys Ile His Ser Gln Thr Val Lys Asp Phe Val Ser Lys Lys Met Gly
                165                 170                 175

Asp Gly Tyr Glu Asp Phe Gly Lys Val Tyr Gln Glu Tyr Ala Glu Ala
            180                 185                 190

Met Asn Thr Leu Ser Leu Lys Ile Met Glu Leu Leu Gly Met Ser Leu
        195                 200                 205

Gly Val Glu Arg Arg Tyr Phe Lys Glu Phe Phe Glu Asp Ser Asp Ser
    210                 215                 220

Ile Phe Arg Leu Asn Tyr Tyr Pro Gln Cys Lys Gln Pro Glu Leu Ala
225                 230                 235                 240

Leu Gly Thr Gly Pro His Cys Asp Pro Thr Ser Leu Thr Ile Leu His
                245                 250                 255

Gln Asp Gln Val Gly Gly Leu Gln Val Phe Val Asp Asn Lys Trp Gln
            260                 265                 270

Ser Ile Pro Pro Asn Pro His Ala Phe Val Val Asn Ile Gly Asp Thr
        275                 280                 285

Phe Met Ala Leu Thr Asn Gly Arg Tyr Lys Ser Cys Leu His Arg Ala
    290                 295                 300

Val Val Asn Ser Glu Arg Glu Arg Lys Thr Phe Ala Phe Phe Leu Cys
305                 310                 315                 320

Pro Lys Gly Glu Lys Val Val Lys Pro Pro Glu Glu Leu Val Asn Gly
                325                 330                 335

Val Lys Ser Gly Glu Arg Lys Tyr Pro Asp Phe Thr Trp Ser Met Phe
            340                 345                 350

Leu Glu Phe Thr Gln Lys His Tyr Arg Ala Asp Met Asn Thr Leu Asp
        355                 360                 365

Glu Phe Ser Ile Trp Leu Lys Asn Arg Arg Ser Phe
    370                 375                 380

<210> SEQ ID NO 13
<211> LENGTH: 378
<212> TYPE: PRT
<213> ORGANISM: Arabidopsis thaliana

<400> SEQUENCE: 13

Met Ala Ile Leu Cys Thr Thr Thr Ser Pro Ala Glu Lys Glu His Glu

```
              1               5                  10                 15
        Pro Lys Gln Asp Leu Glu Lys Asp Gln Thr Ser Pro Leu Ile Phe Asn
                        20                  25                  30

Pro Ser Leu Leu Asn Leu Gln Ser Gln Ile Pro Asn Gln Phe Ile Trp
                        35                  40                  45

Pro Asp Glu Glu Lys Pro Ser Ile Asp Ile Pro Glu Leu Asn Val Pro
                        50                  55                  60

Phe Ile Asp Leu Ser Ser Gln Asp Ser Thr Leu Glu Ala Pro Arg Val
         65                  70                  75                  80

Ile Ala Glu Ala Cys Thr Lys His Gly Phe Phe Leu Val Val Asn His
                        85                  90                  95

Gly Val Ser Glu Ser Leu Ile Ala Asp Ala His Arg Leu Met Glu Ser
                        100                 105                 110

Phe Phe Asp Met Pro Leu Ala Gly Lys Gln Lys Ala Gln Arg Lys Pro
                        115                 120                 125

Gly Glu Ser Cys Gly Tyr Ala Ser Ser Phe Thr Gly Arg Phe Ser Thr
                        130                 135                 140

Lys Leu Pro Trp Lys Glu Thr Leu Ser Phe Gln Phe Ser Asn Asp Asn
        145                 150                 155                 160

Ser Gly Ser Arg Thr Val Gln Asp Tyr Phe Ser Asp Thr Leu Gly Gln
                        165                 170                 175

Glu Phe Glu Gln Phe Gly Lys Val Tyr Gln Asp Tyr Cys Glu Ala Met
                        180                 185                 190

Ser Ser Leu Ser Leu Lys Ile Met Glu Leu Leu Gly Leu Ser Leu Gly
                        195                 200                 205

Val Asn Arg Asp Tyr Phe Arg Gly Phe Phe Glu Glu Asn Asp Ser Ile
                        210                 215                 220

Met Arg Leu Asn His Tyr Pro Pro Cys Gln Thr Pro Asp Leu Thr Leu
        225                 230                 235                 240

Gly Thr Gly Pro His Cys Asp Pro Ser Ser Leu Thr Ile Leu His Gln
                        245                 250                 255

Asp His Val Asn Gly Leu Gln Val Phe Val Asp Asn Gln Trp Gln Ser
                        260                 265                 270

Ile Arg Pro Asn Pro Lys Ala Phe Val Val Asn Ile Gly Asp Thr Phe
                        275                 280                 285

Met Ala Leu Ser Asn Gly Ile Phe Lys Ser Cys Leu His Arg Ala Val
                        290                 295                 300

Val Asn Arg Glu Ser Ala Arg Lys Ser Met Ala Phe Phe Leu Cys Pro
        305                 310                 315                 320

Lys Lys Asp Lys Val Val Lys Pro Ser Asp Ile Leu Glu Lys Met
                        325                 330                 335

Lys Thr Arg Lys Tyr Pro Asp Phe Thr Trp Ser Met Phe Leu Glu Phe
                        340                 345                 350

Thr Gln Lys His Tyr Arg Ala Asp Val Asn Thr Leu Asp Ser Phe Ser
                        355                 360                 365

Asn Trp Val Ile Thr Asn Asn Asn Pro Ile
                        370                 375

<210> SEQ ID NO 14
<211> LENGTH: 372
<212> TYPE: PRT
<213> ORGANISM: Sesbania rostrata

<400> SEQUENCE: 14
```

-continued

```
Met Asp Ser Gly Leu Cys Leu Val Ser Gly Leu Asn His Lys Asp Val
 1               5                  10                  15

Gln Thr Arg Phe Phe Gly Pro Ser Trp Leu Gln Met Gln Ser His Val
                20                  25                  30

Pro Met Asn Phe Ile Trp Pro Lys Glu Cys Leu Val Asn Ala His Glu
             35                  40                  45

Glu Leu Gln Ala Pro Leu Val Asp Leu Asp Gly Phe Leu Arg Gly Asp
 50                  55                  60

Glu Glu Ala Thr His Arg Ala Ala Glu Leu Ile Ser Lys Ala Cys Leu
 65                  70                  75                  80

Thr His Gly Phe Phe Gln Val Ile Asn His Gly Val Asp Gln Arg Leu
                 85                  90                  95

Ile Gly Glu Ala Tyr Asn Gln Met Asp Gly Phe Phe Lys Leu Pro Ile
                100                 105                 110

Asp Arg Lys Leu Ser Val Arg Lys Ile Pro Gly Ser Met Trp Gly Tyr
            115                 120                 125

Ser Gly Ala His Ala Asp Arg Phe Ser Ser Lys Leu Pro Trp Lys Glu
130                 135                 140

Thr Leu Ser Phe Pro Phe His Asp Asn Asn Ser Glu Pro Val Val Thr
145                 150                 155                 160

Asn Tyr Phe Asn Ser Thr Leu Gly Lys Thr Phe Glu Gln Thr Gly Val
                165                 170                 175

Thr Phe Gln Lys Tyr Cys Glu Ala Met Lys Gly Leu Gly Met Lys Leu
            180                 185                 190

Met Glu Leu Leu Ala Ile Ser Leu Asp Val Asp Arg Phe His Tyr Lys
        195                 200                 205

Asp Leu Phe Glu Asp Gly Cys Ser Ile Met Arg Cys Asn Tyr Tyr Pro
210                 215                 220

Ser Cys Gln Gln Pro Ser Leu Ala Leu Gly Thr Gly Pro His Cys Asp
225                 230                 235                 240

Pro Thr Thr Leu Thr Ile Leu His Gln Asp Gln Val Gly Gly Leu Asp
                245                 250                 255

Val Phe Ala Asp Lys Lys Trp Gln Thr Val Arg Pro Leu Pro His Ala
            260                 265                 270

Leu Val Val Asn Ile Gly Asp Thr Phe Thr Ala Leu Ser Asn Gly Arg
        275                 280                 285

Tyr Lys Ser Cys Leu His Arg Ala Val Val Asn Gln Tyr Lys Glu Arg
290                 295                 300

Arg Ser Leu Ala Phe Phe Val Cys Pro Lys Glu Asp Lys Val Val Arg
305                 310                 315                 320

Pro Pro Glu Asp Ile Val Arg Arg Asp Gly Thr Lys Gln Tyr Pro Asp
                325                 330                 335

Phe Thr Trp Ser Lys Leu Leu Glu Phe Thr Gln Lys Tyr Tyr Arg Ala
            340                 345                 350

Asp Glu Asp Thr Leu Gln Asn Phe Thr Lys Trp Leu Leu Ser Ser Lys
        355                 360                 365

Pro Gln Thr Leu
    370
```

<210> SEQ ID NO 15
<211> LENGTH: 380
<212> TYPE: PRT
<213> ORGANISM: Pisum sativum

<400> SEQUENCE: 15

```
Met Ala Ile Glu Cys Ile Thr Ser Ser Ala Lys Leu Met Thr Gln Lys
 1               5                  10                  15

Ser Asp Lys Asn Glu Asn Glu Ser Ser Lys Leu Val Phe Asp Ala
            20                  25                  30

Ser Phe Leu Lys Asn Gln Leu Asn Leu Pro Lys Gln Phe Ile Trp Pro
         35                  40                  45

Asp Asp Glu Lys Pro Cys Met Asn Val Pro Glu Leu Asp Val Pro Leu
 50                  55                  60

Ile Asp Phe Lys Asn Phe Leu Ser Gly Asp Pro Phe Ala Ala Met Glu
 65                  70                  75                  80

Ala Ser Lys Thr Ile Gly Glu Ala Cys Glu Lys His Gly Phe Phe Leu
                 85                  90                  95

Val Val Asn His Gly Ile Asp Thr Lys Leu Ile Glu His Ala His Ser
            100                 105                 110

Tyr Met Asn Asp Phe Phe Glu Val Pro Leu Ser Gln Lys Gln Arg Cys
            115                 120                 125

Gln Arg Lys Thr Gly Glu His Cys Gly Tyr Ala Ser Ser Phe Thr Gly
130                 135                 140

Arg Phe Ser Ser Asn Leu Pro Trp Lys Glu Thr Leu Ser Phe Gln Phe
145                 150                 155                 160

Ser Asp Glu Lys Asn Ser Ser Asn Ile Val Lys Asp Tyr Leu Ser Asn
                165                 170                 175

Thr Leu Gly Glu Asp Phe Gln Gln Phe Gly Glu Val Tyr Gln Glu Tyr
            180                 185                 190

Cys Glu Ala Met Ser Lys Leu Ser Leu Gly Ile Met Glu Leu Leu Gly
            195                 200                 205

Met Ser Leu Gly Val Gly Lys Glu Cys Phe Arg Asp Phe Phe Glu Glu
            210                 215                 220

Asn Lys Ser Ile Met Arg Leu Asn Tyr Tyr Pro Pro Cys Gln Lys Pro
225                 230                 235                 240

Asp Leu Thr Leu Gly Thr Gly Pro His Cys Asp Pro Thr Ser Leu Thr
                245                 250                 255

Ile Leu His Gln Asp Gln Val Gly Gly Leu Gln Val Phe Val Asp Asn
            260                 265                 270

Glu Trp His Ser Ile Arg Pro Asn Phe Asn Ala Phe Val Val Asn Ile
            275                 280                 285

Gly Asp Thr Phe Met Ala Leu Ser Asn Gly Arg Tyr Lys Ser Cys Leu
        290                 295                 300

His Arg Ala Val Val Asn Asn Lys Thr Thr Arg Lys Ser Leu Ala Phe
305                 310                 315                 320

Phe Leu Cys Pro Lys Gly Asp Lys Val Val Ser Pro Ser Glu Leu
                325                 330                 335

Val Asn Asp Leu Thr Pro Arg Ile Tyr Pro Asp Phe Thr Trp Pro Met
            340                 345                 350

Leu Leu Glu Phe Thr Gln Lys His Tyr Arg Ala Asp Met Arg Thr Leu
            355                 360                 365

Glu Ala Phe Thr Lys Trp Ile Gln Gln Lys Gln Asn
        370                 375                 380

<210> SEQ ID NO 16
<211> LENGTH: 380
<212> TYPE: PRT
<213> ORGANISM: Pisum sativum
```

<400> SEQUENCE: 16

```
Met Ala Ile Glu Cys Ile Thr Ser Ser Ala Lys Leu Met Thr Gln Lys
  1               5                  10                  15

Ser Asp Lys Asn Glu Asn Glu Glu Ser Ser Lys Leu Val Phe Asp Ala
             20                  25                  30

Ser Phe Leu Lys Asn Gln Leu Asn Leu Pro Lys Arg Phe Ile Trp Pro
         35                  40                  45

Asp Asp Glu Lys Pro Cys Met Asn Val Pro Glu Leu Asp Val Pro Leu
     50                  55                  60

Ile Asp Phe Lys Asn Phe Leu Ser Gly Asp Pro Phe Ala Ala Met Glu
 65                  70                  75                  80

Ala Ser Lys Thr Ile Gly Glu Ala Cys Glu Lys His Gly Phe Phe Leu
                 85                  90                  95

Val Val Asn His Gly Ile Asp Thr Lys Leu Ile Glu His Ala His Ser
            100                 105                 110

Tyr Met Asn Asp Phe Phe Glu Val Pro Leu Ser Gln Lys Gln Arg Cys
        115                 120                 125

Gln Arg Lys Thr Gly Glu His Cys Gly Tyr Ala Ser Ser Phe Thr Gly
    130                 135                 140

Arg Phe Ser Ser Asn Leu Pro Trp Lys Glu Thr Leu Ser Phe Gln Phe
145                 150                 155                 160

Ser Asp Glu Lys Asn Pro Ser His Ile Val Lys Asp Tyr Leu Ser Asn
                165                 170                 175

Thr Leu Gly Glu Asp Phe Gln Gln Phe Gly Glu Val Tyr Gln Glu Tyr
            180                 185                 190

Cys Glu Ala Met Ser Lys Leu Ser Leu Gly Ile Met Glu Leu Leu Gly
        195                 200                 205

Met Ser Leu Gly Val Gly Lys Glu Cys Phe Arg Asp Phe Phe Glu Glu
    210                 215                 220

Asn Lys Ser Ile Met Arg Leu Asn Tyr Tyr Pro Pro Cys Gln Lys Pro
225                 230                 235                 240

Asp Leu Thr Leu Gly Thr Gly Pro His Cys Asp Pro Thr Ser Leu Thr
                245                 250                 255

Ile Leu His Gln Asp Gln Val Gly Gly Leu Gln Val Phe Val Asp Asn
            260                 265                 270

Glu Trp His Ser Ile Arg Pro Asn Phe Asn Ala Phe Val Val Asn Ile
        275                 280                 285

Gly Asp Thr Phe Met Ala Leu Ser Asn Gly Arg Tyr Lys Ser Cys Leu
    290                 295                 300

His Arg Ala Val Val Asn Asn Lys Thr Thr Arg Lys Ser Leu Ala Phe
305                 310                 315                 320

Phe Leu Cys Pro Lys Gly Asp Lys Val Val Ser Pro Ser Glu Leu
                325                 330                 335

Val Asn Asp Leu Thr Pro Arg Ile Tyr Pro Asp Phe Thr Trp Pro Met
            340                 345                 350

Leu Leu Glu Phe Thr Gln Lys His Tyr Arg Ala Asp Met Arg Thr Leu
        355                 360                 365

Glu Ala Phe Thr Lys Trp Ile Gln Gln Lys Gln Asn
    370                 375                 380

<210> SEQ ID NO 17
<211> LENGTH: 379
<212> TYPE: PRT
<213> ORGANISM: Pisum sativum
```

<400> SEQUENCE: 17

```
Met Lys Val Leu Cys Ser Ser Met Leu Phe Ala Pro Pro Asn Ala Asn
 1               5                  10                  15
Glu Ser Phe Met Asn Glu Gln Lys Gln Cys Leu Asp Asn Thr Ser Ser
             20                  25                  30
Leu Pro Leu Gln Ile Thr Asn Ile Pro Ser Glu Phe Ile Trp Pro Asp
         35                  40                  45
His Glu Lys Pro Cys Leu Thr Pro Pro Lys Leu Glu Val Pro Pro Ile
     50                  55                  60
Asp Leu Lys Ala Phe Leu Ser Asp Pro Lys Ser Ile Ser Asn Ala
 65                  70                  75                  80
Cys Ser Lys Val Asn His Ala Cys Lys Lys His Gly Phe Phe Leu Val
                 85                  90                  95
Val Asn His Gly Val Asp Asn Lys Leu Ile Ala Gln Ala His Lys Leu
             100                 105                 110
Val Asp Glu Phe Phe Cys Met Gln Leu Ser Glu Lys Gln Arg Ala Gln
         115                 120                 125
Arg Lys Ile Gly Glu His Cys Gly Tyr Ala Asn Ser Phe Ile Gly Arg
     130                 135                 140
Phe Ser Ser Lys Leu Pro Trp Lys Glu Thr Leu Ser Phe Arg Tyr Ser
145                 150                 155                 160
Ala Asp Glu Ser Cys Arg Thr Val Glu Asp Tyr Phe Val Asn Ile Met
                 165                 170                 175
Gly Glu Asp Phe Arg Gln Phe Gly Ile Val Tyr Gln Lys Tyr Cys Glu
             180                 185                 190
Ala Met Ser Asn Leu Ser Leu Gly Ile Met Glu Leu Leu Gly Met Ser
         195                 200                 205
Leu Gly Val Gly Lys Glu Tyr Phe Arg Glu Phe Phe Glu Gly Asn Glu
     210                 215                 220
Ser Val Met Arg Leu Asn Tyr Tyr Pro Pro Cys Lys Asn Pro Asp Leu
225                 230                 235                 240
Ala Phe Gly Thr Gly Pro His Cys Asp Pro Thr Ser Leu Thr Ile Leu
                 245                 250                 255
His Gln Asp Gln Val Glu Gly Leu Gln Val Leu Val Asp Gly Ile Trp
             260                 265                 270
His Ser Val Val Pro Lys Glu Asp Ala Phe Val Val Asn Ile Gly Asp
         275                 280                 285
Thr Phe Met Ala Leu Ser Asn Gly Met Phe Lys Ser Cys Leu His Arg
     290                 295                 300
Ala Ile Val Asn Asp Lys Ile Val Arg Lys Ser Leu Ala Phe Phe Leu
305                 310                 315                 320
Cys Pro Asn Glu Asp Lys Ile Val Thr Pro Pro Lys Glu Leu Ile Asp
                 325                 330                 335
Lys Glu Asn Pro Arg Lys Tyr Pro Asn Phe Thr Trp Pro Ser Leu Leu
             340                 345                 350
Glu Phe Thr Gln Lys His Tyr Arg Ala Asp Glu Arg Thr Leu Asp Ala
         355                 360                 365
Phe Ser Met Trp Leu Gln Glu Lys Thr Thr Thr
     370                 375
```

<210> SEQ ID NO 18
<211> LENGTH: 177
<212> TYPE: PRT

<213> ORGANISM: Fagus sylvatica

<400> SEQUENCE: 18

```
Asn Phe Pro Trp Lys Glu Thr Leu Ser Phe Arg Ser Ser Ala Gln Pro
1               5                   10                  15

Asp Ser Ser Asn Ile Val Gln Asp Tyr Leu Cys Asn Thr Met Gly Glu
            20                  25                  30

Asp Phe Lys Pro Phe Gly Lys Val Tyr Gln Asp Tyr Cys Asp Ala Met
        35                  40                  45

Ser Thr Leu Ser Leu Gly Ile Met Glu Leu Leu Gly Met Ser Leu Gly
    50                  55                  60

Val Ser Gln Gly His Tyr Arg Glu Phe Phe Glu Glu Asn Glu Ser Ile
65                  70                  75                  80

Met Arg Leu Asn Tyr Tyr Pro Pro Cys Gln Lys Pro Asp Leu Thr Leu
                85                  90                  95

Gly Thr Gly Pro His Cys Asp Pro Thr Ser Leu Thr Ile Leu His Gln
            100                 105                 110

Asp Gln Val Gly Gly Leu Gln Val Phe Val Asp Glu Glu Trp Arg Ser
        115                 120                 125

Ile Thr Pro Asn Phe Asn Ala Phe Val Val Asn Ile Gly Asp Thr Phe
    130                 135                 140

Met Ala Leu Ser Asn Gly Arg Tyr Lys Ser Cys Leu His Arg Ala Met
145                 150                 155                 160

Val Asn Ser Lys Thr Pro Arg Lys Ser Leu Ala Phe Phe Cys Pro
                165                 170                 175

Lys
```

<210> SEQ ID NO 19
<211> LENGTH: 379
<212> TYPE: PRT
<213> ORGANISM: Fagus sylvatica

<400> SEQUENCE: 19

```
Met Ala Ile Asp Cys Ile Thr Asn Ile Thr Ser Met Pro His Pro Pro
1               5                   10                  15

Lys Glu Glu His Lys Asp His Gln Lys Gln Leu Val Phe Asp Ala Ser
            20                  25                  30

Val Leu Arg His Gln Thr Asn Ile Pro Gln Gln Phe Ile Trp Pro Asp
        35                  40                  45

Glu Glu Lys Pro Arg Ala Asn Ala Pro Glu Leu Gln Val Pro Leu Ile
    50                  55                  60

Asp Leu Arg Gly Phe Leu Ser Gly Asp Pro Thr Ala Ala Asn Glu Ala
65                  70                  75                  80

Ser Ser Leu Val Gly Lys Ala Cys Gln Lys His Gly Phe Phe Leu Val
                85                  90                  95

Val Asn His Gly Val Asp Asp Lys Leu Ile Ala His Ala His Gln Tyr
            100                 105                 110

Ile Asp Tyr Phe Phe Glu Leu Pro Met Ser Ala Lys Gln Arg Ala Gln
        115                 120                 125

Arg Lys Val Gly Glu His Cys Gly Tyr Ala Ser Ser Phe Thr Gly Arg
    130                 135                 140

Phe Ser Phe Lys Leu Pro Trp Lys Glu Thr Leu Ser Phe Arg Ser Ser
145                 150                 155                 160

Ala Gln Pro Asp Ser Ser Asn Ile Val Gln Asp Tyr Leu Cys Asn Thr
                165                 170                 175
```

```
Met Gly Glu Asp Phe Lys Pro Phe Gly Lys Val Tyr Gln Asp Tyr Cys
            180                 185                 190

Asp Ala Met Ser Thr Leu Ser Leu Gly Ile Met Glu Leu Leu Gly Met
            195                 200                 205

Ser Leu Gly Val Ser Gln Gly His Tyr Arg Glu Phe Phe Glu Glu Asn
            210                 215                 220

Glu Ser Ile Met Arg Leu Asn Tyr Tyr Pro Cys Gln Lys Pro Asp
225                 230                 235                 240

Leu Thr Leu Gly Thr Gly Pro His Cys Asp Pro Thr Ser Leu Thr Ile
            245                 250                 255

Leu His Gln Asp Gln Val Gly Gly Leu Gln Val Phe Val Asp Glu Glu
            260                 265                 270

Trp Arg Ser Ile Thr Pro Asn Phe Asn Ala Phe Val Val Asn Ile Gly
            275                 280                 285

Asp Thr Phe Met Ala Leu Ser Asn Gly Arg Tyr Lys Ser Cys Leu His
            290                 295                 300

Arg Ala Val Val Asn Ser Lys Thr Pro Arg Lys Ser Leu Ala Phe Phe
305                 310                 315                 320

Leu Cys Pro Lys Asn Asp Lys Val Val Ser Pro Ser Glu Leu Val
            325                 330                 335

Asp Ser Leu Cys Pro Arg Val Tyr Pro Asp Phe Thr Trp Pro Met Leu
            340                 345                 350

Leu Glu Phe Thr Gln Lys His Tyr Arg Ala Asp Val Lys Thr Leu Glu
            355                 360                 365

Val Phe Ser Asn Trp Leu Gln Gln Lys Asn Ser
            370                 375

<210> SEQ ID NO 20
<211> LENGTH: 382
<212> TYPE: PRT
<213> ORGANISM: Phaseolus vulgaris

<400> SEQUENCE: 20

Met Ala Ile Asp Cys Met Thr Asn Ile Gln Thr Met Ser Gln Pro Gln
1               5                   10                  15

Lys His His Gln Asp Asn Lys Glu Asp Glu Ala Pro Leu Val Phe
            20                  25                  30

Asp Ala Ser Leu Leu Arg His Gln Leu Asn Leu Pro Lys Gln Phe Ile
            35                  40                  45

Trp Pro Asp Asp Glu Lys Pro Cys Met Asn Val Pro Glu Leu Val Val
50                  55                  60

Pro Leu Ile Asp Leu Arg Gly Phe Leu Ser Gly Asp Pro Val Ala Thr
65                  70                  75                  80

Met Glu Ala Ala Arg Met Val Gly Glu Ala Cys Gln Lys His Gly Phe
            85                  90                  95

Phe Leu Val Val Asn His Gly Ile Asp Ala Asn Leu Ile Ser His Ala
            100                 105                 110

His Ser Tyr Met Asp Asp Phe Phe Glu Val Pro Leu Thr Gln Lys Gln
            115                 120                 125

Arg Ala Gln Arg Lys Thr Gly Glu His Cys Gly Tyr Ala Ser Ser Phe
130                 135                 140

Thr Gly Arg Phe Ser Ser Lys Leu Pro Trp Lys Glu Thr Leu Ser Phe
145                 150                 155                 160

Gln Phe Ser Ala Glu Glu Lys Ser Ser Thr Ile Val Lys Asp Tyr Leu
```

-continued

```
                165                 170                 175
Cys Asn Thr Leu Gly Gln Glu Phe Glu Gln Phe Gly Arg Val Tyr Gln
            180                 185                 190

Asp Tyr Cys Asp Ala Met Ser Asn Leu Ser Leu Gly Ile Met Glu Leu
            195                 200                 205

Leu Gly Met Ser Leu Gly Val Gly Lys Ala Cys Phe Arg Glu Phe Phe
            210                 215                 220

Glu Glu Asn Asp Ser Ile Met Arg Leu Asn Tyr Tyr Pro Pro Cys Gln
225                 230                 235                 240

Lys Pro Asp Leu Thr Leu Gly Thr Gly Pro His Cys Asp Pro Thr Ser
            245                 250                 255

Leu Thr Ile Leu His Gln Asp Gln Val Gly Gly Leu Gln Val Phe Val
            260                 265                 270

Asp Asn Glu Trp His Ser Ile Asn Pro Asn Phe Asn Ala Phe Val Val
            275                 280                 285

Asn Ile Gly Asp Thr Phe Met Ala Leu Ser Asn Gly Arg Tyr Lys Ser
            290                 295                 300

Cys Leu His Arg Ala Val Val Asn Ser Lys Thr Thr Arg Lys Ser Leu
305                 310                 315                 320

Ala Phe Phe Leu Cys Pro Lys Gly Asp Lys Val Val Ser Pro Pro Ser
            325                 330                 335

Glu Leu Val Asp Asp Leu Thr Pro Arg Leu Tyr Pro Asp Phe Thr Trp
            340                 345                 350

Pro Met Leu Leu Glu Phe Thr Gln Lys His Tyr Arg Ala Asp Met Lys
            355                 360                 365

Thr Leu Glu Ala Phe Thr Asn Trp Leu Gln Gln Lys Arg Ser
            370                 375                 380

<210> SEQ ID NO 21
<211> LENGTH: 370
<212> TYPE: PRT
<213> ORGANISM: Phaseolus vulgaris

<400> SEQUENCE: 21

Met Leu Ile Pro His Pro Ser Met Leu Leu Ala Ser Gln Asn Thr Asn
1               5                   10                  15

Met Glu Pro Gln Gln Ile Asn Leu Gln Ala Pro Thr Pro Asn Gln Ser
            20                  25                  30

Asn Ile Pro Ser Glu Phe Val Trp Pro Asp Asn Glu Lys Pro Cys Leu
            35                  40                  45

Glu Pro Pro Lys Leu Lys Ile Pro Pro Ile Asp Met Lys Gly Phe Leu
        50                  55                  60

Ser Gly Asp Pro Glu Thr Val Ser Ala Ile Cys Ala Glu Val Asn Ala
65                  70                  75                  80

Ala Cys Arg Lys His Gly Phe Phe Leu Val Val Asn His Gly Val Asp
            85                  90                  95

Lys Lys Leu Val Glu Lys Ala His Lys Leu Ile Asp Thr Phe Phe Cys
            100                 105                 110

Met Glu Leu Pro Glu Lys Gln Lys Leu Gln Arg Lys Leu Gly Glu His
            115                 120                 125

Cys Gly Tyr Ala Asn Ser Phe Ile Gly Arg Phe Ser Ser Lys Leu Pro
            130                 135                 140

Trp Lys Glu Thr Leu Ser Phe His Tyr Ala Pro Asp Thr Lys Thr Val
145                 150                 155                 160
```

```
Glu Asp Tyr Phe Leu Asn Ser Met Gly Glu Glu Phe Arg Glu Phe Gly
                165                 170                 175

Ser Phe Phe Gln Glu Tyr Cys Glu Val Met Ser Asn Leu Ser Leu Glu
            180                 185                 190

Ile Met Glu Leu Leu Gly Met Ser Leu Gly Val Ser Arg Glu Cys Phe
        195                 200                 205

Arg Asp Phe Phe Lys Asn Asn Glu Ser Val Met Arg Leu Asn Tyr Tyr
    210                 215                 220

Pro Pro Cys His Lys Pro Glu Leu Ala Leu Gly Thr Gly Pro His Cys
225                 230                 235                 240

Asp Pro Thr Ser Leu Thr Val Leu His Gln Asp Val Glu Gly Leu
                245                 250                 255

Gln Val Phe Val Asp Gly Lys Trp Cys Ser Val Ala Pro Lys Glu Asp
            260                 265                 270

Ala Phe Val Val Asn Ile Gly Asp Thr Phe Met Ala Leu Ser Asn Gly
        275                 280                 285

Ile Phe Lys Ser Cys Leu His Arg Ala Val Val Asn Asn Gln Ile Val
    290                 295                 300

Arg Lys Ser Leu Ala Phe Phe Leu Cys Pro Asn Lys Asp Lys Val Val
305                 310                 315                 320

Ser Ala Pro Lys Glu Leu Ile Thr Val Glu Asn Pro Lys Lys Tyr Pro
                325                 330                 335

Asp Phe Thr Trp Pro Asn Leu Leu Glu Phe Thr Gln Leu His Tyr Arg
            340                 345                 350

Ser Asp Pro Glu Thr Leu Asp Ala Phe Ala Asn Trp Val Leu Glu Lys
        355                 360                 365

Asn Lys
    370

<210> SEQ ID NO 22
<211> LENGTH: 385
<212> TYPE: PRT
<213> ORGANISM: Phaseolus vulgaris

<400> SEQUENCE: 22

Met Ala Ile Asp Met His Pro Ile Pro Ile Met Pro Gln Pro Ser Asn
1               5                   10                  15

Gln Glu Ile Lys Glu Gln Asp Gln His Pro Leu Val Phe Asp Ala Ser
                20                  25                  30

Leu Leu Arg His Gln Leu His Ile Pro Ser Gln Phe Val Trp Pro Asp
            35                  40                  45

Glu Glu Lys Ala Cys Leu Asn Glu Pro Glu Leu Pro Val Pro Phe Ile
        50                  55                  60

Asp Leu Gly Gly Phe Leu Ser Gly Asp Pro Leu Ala Ala Thr Glu Ala
65                  70                  75                  80

Ser Arg Leu Val Gly Glu Ala Cys Gln Lys His Gly Phe Phe Leu Val
                85                  90                  95

Val Asn His Gly Ile Gln Gln Leu Ile Ser Asp Ala His Leu Tyr
            100                 105                 110

Met Asp His Phe Phe Ala Leu Pro Leu Ser His Lys Gln Arg Ala Gln
        115                 120                 125

Arg Met Pro Gly Glu His Cys Gly Tyr Ala Ser Ser Phe Thr Gly Arg
    130                 135                 140

Phe Ser Ser Lys Leu Pro Trp Lys Glu Thr Leu Ser Phe Gln Tyr Ser
145                 150                 155                 160
```

Pro Arg Asn Asp Ser Gln Thr Leu Val Lys Asp Tyr Leu Cys Asp Lys
                165                 170                 175

Met Gly Lys Glu Phe Glu Lys Phe Gly Asn Val Tyr Gln Asp Tyr Cys
            180                 185                 190

Glu Ala Met Ser Asn Leu Ser Leu Gly Ile Met Glu Leu Leu Gly Leu
        195                 200                 205

Ser Leu Gly Val Gly Arg Gly Tyr Phe Arg Glu Phe Phe Glu Glu Asn
    210                 215                 220

Asn Ser Ile Met Arg Leu Asn Tyr Tyr Pro Cys Gln Lys Pro Asp
225                 230                 235                 240

Leu Thr Leu Gly Thr Gly Pro His Cys Asp Pro Thr Ser Leu Thr Ile
                245                 250                 255

Leu His Gln Asp Gln Val Gly Gly Leu Gln Val Cys Val Asp Asn Glu
            260                 265                 270

Trp His Ser Ile Lys Pro Asp Val Asn Ala Phe Val Val Asn Val Gly
        275                 280                 285

Asp Thr Phe Met Ala Leu Ser Asn Gly Arg Tyr Lys Ser Cys Leu His
    290                 295                 300

Arg Ala Val Val Asn Ser Glu Thr Thr Arg Lys Ser Leu Ala Phe Phe
305                 310                 315                 320

Leu Cys Pro Arg Ser Asp Lys Val Ser Pro Pro Cys Glu Leu Val
                325                 330                 335

Asp Lys Leu Ser Pro Arg Leu Tyr Pro Asp Phe Thr Trp Pro Met Leu
            340                 345                 350

Leu Glu Phe Thr Gln Lys His Tyr Arg Ala Asp Met Lys Thr Leu Glu
        355                 360                 365

Ala Phe Thr Asn Trp Leu Gln Arg Arg Ser Asn Phe Asp Asn His Ile
    370                 375                 380

Met
385

<210> SEQ ID NO 23
<211> LENGTH: 385
<212> TYPE: PRT
<213> ORGANISM: Gossypium hirsutum

<400> SEQUENCE: 23

Met Val His Cys Leu Pro Lys Val Ser Val Ile Gln Asp Lys Pro Met
1               5                   10                  15

Leu Pro Pro Thr Ala Ala Val Ala Lys Asn Lys His Arg Pro Leu Ala
            20                  25                  30

Phe Asp Ala Ser Ile Leu Gly Ser Glu Ile Ser Ser Gln Phe Ile Trp
        35                  40                  45

Pro Asp Asp Lys Pro Cys Leu Asp Ala Pro Glu Leu Val Ile Pro
    50                  55                  60

Thr Ile Asp Leu Gly Ala Phe Leu Leu Gly Asp Ser Leu Ala Val Ser
65                  70                  75                  80

Lys Ala Ala Glu Ala Val Asn Glu Ala Cys Lys Lys His Gly Phe Phe
                85                  90                  95

Leu Val Val Asn His Gly Val Asp Ser Gly Leu Ile Asp Lys Ala His
            100                 105                 110

Gln Tyr Met Asp Arg Phe Phe Ser Leu Gln Leu Ser Glu Lys Gln Lys
        115                 120                 125

Ala Lys Arg Lys Val Gly Glu Ser Tyr Gly Tyr Ala Ser Ser Phe Val

-continued

```
            130                 135                 140
Gly Arg Phe Ser Ser Lys Leu Pro Trp Lys Glu Thr Leu Ser Phe Arg
145                 150                 155                 160

Tyr Cys Pro His Thr Gln Asn Ile Val Gln His Tyr Met Val Asn Trp
                165                 170                 175

Met Gly Glu Asp Phe Arg Asp Phe Gly Arg Leu Tyr Gln Glu Tyr Cys
            180                 185                 190

Glu Ala Met Asn Lys Val Ser Gln Glu Ile Met Gly Leu Leu Gly Ile
                195                 200                 205

Ser Leu Gly Leu Asp Gln Ala Tyr Phe Lys Asp Phe Phe Asp Glu Asn
210                 215                 220

Asp Ser Ile Leu Arg Leu Asn His Tyr Pro Pro Cys Gln Lys Pro Glu
225                 230                 235                 240

Leu Thr Leu Gly Thr Gly Pro His Thr Asp Pro Thr Ser Leu Thr Ile
                245                 250                 255

Leu His Gln Asp Gln Val Gly Gly Leu Gln Val Phe Ala Asp Glu Lys
                260                 265                 270

Trp His Ser Val Ala Pro Ile Pro Arg Ala Phe Val Val Asn Ile Gly
            275                 280                 285

Asp Thr Phe Met Ala Leu Thr Asn Gly Ile Tyr Lys Ser Cys Leu His
            290                 295                 300

Arg Ala Val Val Asn Thr Glu Thr Val Arg Lys Ser Leu Val Phe Phe
305                 310                 315                 320

Leu Cys Pro Lys Leu Glu Arg Pro Val Thr Pro Ala Ala Gly Leu Val
                325                 330                 335

Asn Ala Ala Asn Ser Arg Lys Tyr Pro Asp Phe Thr Trp Ala Ala Leu
                340                 345                 350

Leu Glu Phe Thr Gln Asn His Tyr Arg Ala Asp Met Lys Thr Leu Val
                355                 360                 365

Ala Phe Ser Lys Trp Val Gln Glu Gln Glu Ser Asn Asn Lys Leu Ile
            370                 375                 380

Pro
385

<210> SEQ ID NO 24
<211> LENGTH: 387
<212> TYPE: PRT
<213> ORGANISM: Gossypium hirsutum

<400> SEQUENCE: 24

Met Val His Cys Leu Pro Lys Val Phe Val Ile Gln Asp Lys Pro Met
1               5                   10                  15

Leu Pro Ser Thr Ala Ala Val Ala Lys Asp Glu His Arg Pro Leu Ala
                20                  25                  30

Phe Asp Ala Ser Ile Leu Gly Ser Glu Ser Asn Ile Pro Ser Gln Phe
            35                  40                  45

Ile Trp Pro Asp Asp Glu Lys Pro Cys Leu Asp Ala Pro Ala Leu Val
50                  55                  60

Ile Pro Thr Ile Asp Leu Gly Ala Phe Leu Leu Gly Asp Ser Leu Ala
65                  70                  75                  80

Val Ser Lys Ala Ala Glu Val Val Asn Glu Ala Cys Lys Lys His Gly
                85                  90                  95

Phe Phe Leu Val Val Asn His Gly Val Asp Ser Gly Leu Ile Asp Lys
            100                 105                 110
```

```
Ala His Gln Tyr Met Asp Arg Phe Phe Ser Leu Gln Leu Ser Glu Lys
            115                 120                 125

Gln Lys Ala Lys Arg Lys Val Gly Glu Ser Tyr Gly Tyr Ala Ser Ser
        130                 135                 140

Phe Val Gly Arg Phe Ser Ser Lys Leu Pro Trp Lys Glu Thr Leu Ser
145                 150                 155                 160

Phe Arg Tyr Cys Pro His Thr Gln Asn Ile Val Gln His Tyr Met Val
                165                 170                 175

Asn Trp Met Gly Glu Asp Phe Arg Asp Phe Gly Arg Leu Tyr Gln Glu
            180                 185                 190

Tyr Cys Glu Ala Met Asn Lys Val Ser Gln Glu Ile Met Gly Leu Leu
        195                 200                 205

Gly Ile Ser Leu Gly Leu Asp Gln Ala Tyr Phe Lys Asp Phe Phe Glu
    210                 215                 220

Gln Asn Asp Ser Ile Leu Arg Leu Asn His Tyr Pro Pro Cys Gln Lys
225                 230                 235                 240

Pro Glu Leu Thr Leu Gly Thr Gly Pro His Thr Asp Pro Thr Ser Leu
                245                 250                 255

Thr Ile Leu His Gln Asp Gln Val Gly Gly Leu Gln Val Phe Ala Asp
            260                 265                 270

Glu Lys Trp His Ser Val Ala Pro Ile Pro Gly Ala Phe Val Val Asn
        275                 280                 285

Val Gly Asp Thr Phe Met Ala Leu Thr Asn Gly Phe Tyr Lys Ser Cys
    290                 295                 300

Leu His Arg Ala Val Val Asn Thr Glu Thr Val Arg Lys Ser Leu Ala
305                 310                 315                 320

Phe Phe Leu Cys Pro Lys Leu Glu Arg Pro Val Thr Pro Ala Ala Gly
                325                 330                 335

Leu Val Thr Ala Glu Asn Pro Arg Lys Tyr Pro Asp Phe Thr Trp Ala
            340                 345                 350

Ala Leu Leu Lys Phe Thr Gln Asn His Tyr Arg Ala Asp Met Lys Thr
        355                 360                 365

Leu Val Ala Phe Ser Lys Trp Val Gln Glu Gln Glu Ser Asn Tyr Lys
    370                 375                 380

Leu Ile Pro
385

<210> SEQ ID NO 25
<211> LENGTH: 388
<212> TYPE: PRT
<213> ORGANISM: Gossypium hirsutum

<400> SEQUENCE: 25

Met Val His Cys Leu Pro Lys Val Phe Val Ile Gln Asp Lys Pro Ile
1               5                   10                  15

Leu Pro Ser Thr Ala Val Ala Lys Asp Glu Tyr Trp Pro Pro Leu
            20                  25                  30

Ala Phe Asp Ala Ser Ile Leu Gly Ser Glu Ser Asn Ile Pro Ser Gln
        35                  40                  45

Phe Ile Trp Pro Asp Asp Glu Lys Pro Cys Leu Asp Ala Pro Glu Leu
    50                  55                  60

Val Ile Pro Thr Ile Asp Leu Gly Ala Phe Leu Leu Arg Tyr Ser Leu
65                  70                  75                  80

Ala Val Ser Lys Ala Ala Glu Val Val Asn Glu Ala Cys Lys Lys His
            85                  90                  95
```

Gly Phe Phe Leu Val Val Asn His Gly Val Asp Ser Gly Leu Ile Asp
            100                 105                 110

Lys Ala His Gln Tyr Met Asp Arg Phe Phe Ser Leu Gln Leu Ser Glu
        115                 120                 125

Lys Gln Lys Ala Lys Arg Lys Val Gly Glu Ser Tyr Gly Tyr Ala Ser
    130                 135                 140

Ser Phe Val Gly Arg Phe Ser Ser Lys Leu Pro Trp Lys Glu Thr Leu
145                 150                 155                 160

Ser Phe Arg Tyr Cys Pro Arg Thr Gln Asn Ile Val Gln His Tyr Met
                165                 170                 175

Val Asn Leu Met Gly Glu Asp Phe Arg Asp Phe Gly Arg Leu Tyr Gln
            180                 185                 190

Glu Tyr Cys Glu Ala Met Asn Lys Val Ser Gln Glu Ile Met Gly Leu
        195                 200                 205

Leu Gly Ile Ser Leu Gly Leu Asp Gln Ala Tyr Phe Lys Asp Phe Phe
    210                 215                 220

Glu Gln Asn Asp Ser Ile Leu Arg Leu Asn His Tyr Pro Pro Cys Gln
225                 230                 235                 240

Lys Pro Glu Leu Thr Leu Gly Thr Gly Pro His Thr Asp Pro Thr Ser
                245                 250                 255

Leu Thr Ile Leu His Gln Asp Gln Val Gly Gly Leu Gln Val Phe Ala
            260                 265                 270

Asp Glu Lys Trp His Ser Val Ala Pro Tyr Pro Gly Ala Phe Val Val
        275                 280                 285

Asn Val Gly Asp Thr Phe Met Ala Leu Thr Lys Ala Phe Tyr Lys Ser
    290                 295                 300

Cys Leu His Arg Ala Val Asn Thr Glu Thr Val Arg Lys Ser Leu
305                 310                 315                 320

Arg Phe Phe Leu Cys Pro Lys Leu Glu Arg Pro Val Thr Pro Ala Ala
                325                 330                 335

Gly Leu Val Thr Ala Glu Asn Pro Arg Lys Tyr Pro Asp Phe Thr Trp
            340                 345                 350

Ala Ala Leu Leu Lys Phe Thr Gln Asn His Tyr Arg Ala Asp Met Lys
        355                 360                 365

Thr Leu Val Ala Phe Ser Lys Trp Val Gln Gln Glu Ser Asn Tyr
    370                 375                 380

Lys Leu Ile Pro
385

<210> SEQ ID NO 26
<211> LENGTH: 386
<212> TYPE: PRT
<213> ORGANISM: Ipomoea nil

<400> SEQUENCE: 26

Met Ala Ile Glu Cys Met Ile Pro Thr Pro Thr Pro Asn His Glu Arg
1               5                   10                  15

Gln Glu Ile Glu Asn Lys Pro Ala Ala Val Val Phe Asp Ser Pro
            20                  25                  30

Val Leu Arg His Glu Ser Asn Ile Pro Thr Glu Phe Leu Trp Pro Asp
        35                  40                  45

His Glu Lys Pro Gly Pro Tyr Ala Ala Arg Glu Phe Gln Val Pro Val
    50                  55                  60

Ile Asp Met Ala Ala Phe Arg Ser Gly Asp Pro Val Ala Val Ala Glu

```
             65                  70                  75                  80
Thr Cys Lys Leu Val Asp Glu Ala Cys Lys Lys His Gly Phe Phe Leu
                        85                  90                  95

Val Val Asn His Gly Val Asp Thr Glu Leu Leu Ser Asp Gly Val Arg
            100                 105                 110

Glu Met Asp Arg Tyr Phe Glu Leu Pro Leu Ser Phe Lys Glu Lys Ala
            115                 120                 125

Leu Arg Lys Leu Gly Glu His Cys Gly Tyr Ala Ser Ser Phe Thr Gly
            130                 135                 140

Arg Phe Asn Ala Lys Leu Pro Trp Lys Glu Thr Leu Ser Phe Arg Phe
145                 150                 155                 160

Ser Ala Glu Lys Glu Cys Ser His Val Val Gly Glu Tyr Phe Glu Lys
                165                 170                 175

Thr Leu Gly Gln Glu Phe Ala Asp Leu Gly Glu Leu Tyr Gln Lys Tyr
                180                 185                 190

Cys Asn Ala Met Asn Thr Leu Ala Leu Glu Ile Thr Glu Leu Leu Gly
                195                 200                 205

Met Gly Leu Gly Val Asp Arg Lys His Phe Ser Glu Phe Tyr Gln Glu
            210                 215                 220

Asn Asp Ser Val Leu Arg Leu Asn Tyr Tyr Pro Pro Cys Gln Lys Pro
225                 230                 235                 240

Glu Leu Thr Leu Gly Thr Gly Pro His Cys Asp Pro Thr Ser Leu Thr
                    245                 250                 255

Ile Leu His Gln Asp Ser Val Ser Gly Leu Gln Val Phe Val Asp Asn
                260                 265                 270

Glu Trp Arg Ala Val Asn Pro Thr Pro Asn Ala Phe Val Val Asn Ile
            275                 280                 285

Gly Asp Thr Phe Met Ala Leu Ser Asn Gly Leu Tyr Lys Ser Cys Met
            290                 295                 300

His Arg Ala Val Val Asn Asn Glu Ile Pro Arg Lys Ser Ile Ala Phe
305                 310                 315                 320

Phe Leu Cys Pro His Lys Asp Lys Val Val Thr Pro Pro Glu Leu
                325                 330                 335

Val Asp Ala Thr His Pro Lys Leu Tyr Pro Asp Phe Lys Trp Pro Ala
            340                 345                 350

Leu Leu Glu Tyr Thr Gln Leu His Tyr Arg Ser Asp Thr Asp Thr Leu
                355                 360                 365

Leu Asn Phe Ala Thr Trp Leu Gln Gln Asn Gln Thr Leu His Ala Thr
            370                 375                 380

Gln Ala
385

<210> SEQ ID NO 27
<211> LENGTH: 381
<212> TYPE: PRT
<213> ORGANISM: Ipomoea nil

<400> SEQUENCE: 27

Met Ala Ile Glu Cys Val Thr Thr Thr Pro Thr Arg Ser Asp Asp Pro
1               5                  10                  15

Lys Ala Ala Ala Val Val Phe Asp Ser Ser Val Leu Arg His Glu Thr
            20                  25                  30

Asn Ile Pro Thr Glu Phe Val Trp Pro Glu His Glu Lys Pro Gly Ser
        35                  40                  45
```

```
Tyr Ala Ala Pro Glu Cys Pro Val Pro Val Ile Asp Leu Ala Ala Phe
        50              55                  60

Arg Ser Gly Asp Pro Ala Val Ala Glu Thr Leu Lys Leu Val Asn
 65              70                  75                  80

Glu Ala Cys Lys Lys His Gly Phe Phe Leu Val Val Asn His Gly Val
                 85                  90                  95

Asp Pro Asp Arg Ile Ser Asp Ala Ile Arg His Met Asp Arg Phe Phe
                100                 105                 110

Asp Leu Pro Leu Ser Ser Lys Glu Lys Ala Leu Arg Lys Val Gly Glu
            115                 120                 125

Ser Cys Gly Tyr Ala Ser Ser Phe Thr Gly Arg Phe Ser Ala Lys Leu
        130                 135                 140

Pro Trp Lys Glu Thr Leu Ser Phe Arg Tyr Ser Ala Gln Lys Glu Cys
145                 150                 155                 160

Ser His Ile Val Glu Glu Tyr Phe Gln Glu Ser Leu Gly Gln Asp Phe
                165                 170                 175

Ala His Ile Gly Leu Val Tyr Gln Lys Tyr Ser Asn Glu Met Ser Lys
                180                 185                 190

Leu Ala Leu Glu Ile Met Glu Val Leu Gly Met Gly Leu Gly Val Asn
            195                 200                 205

Arg Lys His Phe Ser Asp Phe Phe Gln Glu Asn Asp Ser Val Met Arg
        210                 215                 220

Leu Asn Tyr Cys Pro Pro Cys Gln Lys Pro Glu Ile Thr Leu Gly Thr
225                 230                 235                 240

Gly Pro His Cys Asp Pro Thr Ser Leu Thr Ile Leu His Gln Asp Asn
                245                 250                 255

Ser Val Asn Gly Leu Gln Val Cys Val Asp Asn Glu Trp Arg Ser Val
            260                 265                 270

Ser Pro Ser Pro Asn Ala Phe Val Val Asn Ile Gly Asp Thr Phe Met
        275                 280                 285

Ala Leu Ser Asn Gly Ile Tyr Lys Ser Cys Leu His Arg Ala Val Val
290                 295                 300

Asn Ser Thr Ile Thr Arg Lys Ser Met Ala Phe Phe Leu Cys Pro His
305                 310                 315                 320

Glu Asp Lys Val Val Thr Pro Pro Glu Leu Val Asp Ser Thr His
                325                 330                 335

Pro Arg Leu Tyr Pro Asp Phe Lys Trp Pro Thr Leu Leu Glu Phe Thr
            340                 345                 350

Gln Lys His Tyr Arg Ser Asp Thr Asp Thr Leu Leu Ser Phe Ser Ala
        355                 360                 365

Trp Leu Gln Gln Asn Gln Thr Pro His Ala Thr His Pro
370                 375                 380

<210> SEQ ID NO 28
<211> LENGTH: 379
<212> TYPE: PRT
<213> ORGANISM: Nicotiana tabacum

<400> SEQUENCE: 28

Met Ala Ile Asp Cys Met Ile Thr Asn Val Asn Ser Pro Met Leu Arg
 1               5                  10                  15

Ile Leu Glu Asp Asp Lys Lys Pro Leu Ile Phe Asp Ala Ser Gln Met
             20                  25                  30

Lys Arg Glu Tyr Asn Ile Pro Thr Gln Phe Ile Trp Pro Asp Asp Glu
         35                  40                  45
```

```
Lys Pro Arg Ala Val Ala Arg Glu Leu Pro Val Pro Leu Ile Asp Leu
     50                  55                  60

Gly Gly Phe Leu Ser Gly Asp Pro Val Ala Ala Gln Gln Ala Ser Arg
 65                  70                  75                  80

Leu Val Gly Glu Ala Cys Arg Asn His Gly Phe Phe Leu Val Val Asn
                 85                  90                  95

His Gly Val Asn Ala Asn Leu Ile Ser Asn Ala His Arg Tyr Met Asp
            100                 105                 110

Met Phe Phe Asp Leu Pro Leu Ser Glu Lys Gln Lys Ala Gln Arg Lys
                115                 120                 125

Leu Glu Glu His Cys Gly Tyr Ala Ser Ser Phe Thr Gly Arg Phe Ser
            130                 135                 140

Ser Lys Leu Pro Trp Lys Glu Thr Leu Ser Phe Arg Tyr Ser Ala Glu
145                 150                 155                 160

Glu Asp Ser Ser His Ile Val Glu Glu Tyr Phe Gln Asn Thr Met Gly
                165                 170                 175

Glu Ser Phe Ser His Leu Gly Asn Val Tyr Gln Glu Tyr Cys Asn Ser
                180                 185                 190

Met Ser Thr Leu Ser Leu Gly Ile Met Glu Leu Leu Gly Met Ser Leu
            195                 200                 205

Gly Val Gly Arg Glu His Phe Lys Glu Phe Glu Glu Asn Glu Ser
    210                 215                 220

Ile Met Arg Leu Asn Tyr Tyr Pro Pro Cys Gln Lys Pro Asp Leu Thr
225                 230                 235                 240

Leu Gly Thr Gly Pro His Cys Asp Pro Thr Ser Leu Thr Ile Leu His
                245                 250                 255

Gln Asp Ser Val Gly Gly Leu Gln Val Phe Val Asp Asn Glu Trp Arg
            260                 265                 270

Ser Val Ser Pro Asn Phe Asn Ala Phe Val Val Asn Ile Gly Asp Thr
        275                 280                 285

Phe Met Ala Leu Ser Asn Gly Arg Tyr Lys Ser Cys Leu His Arg Ala
    290                 295                 300

Val Val Asn Asn Lys Thr Pro Arg Lys Ser Leu Ala Phe Phe Leu Val
305                 310                 315                 320

Pro Lys Lys Asp Lys Val Ser Pro Asn Glu Leu Val Asp Thr
                325                 330                 335

Asn Asn Pro Arg Ile Tyr Pro Asp Phe Thr Trp Pro Thr Leu Leu Glu
            340                 345                 350

Phe Thr Gln Lys His Tyr Arg Ala Asp Met Asn Thr Leu Gln Thr Phe
            355                 360                 365

Ser Asn Trp Leu Lys Gln Lys Thr Ala Gln Val
            370                 375

<210> SEQ ID NO 29
<211> LENGTH: 384
<212> TYPE: PRT
<213> ORGANISM: Solanum demissum

<400> SEQUENCE: 29

Met Ala Ile Asp Cys Met Ile Thr Arg Asn Asn Met Thr Ser Lys
 1               5                  10                  15

Glu Gly Gln Glu Tyr Asp Ile Ile Lys Thr Asn Lys Ser Leu Ser Phe
             20                  25                  30

Asp Ala Ser Leu Met Lys Asn Glu Ser Asn Ile Pro Ser Gln Phe Ile
```

-continued

```
                35                  40                  45
Trp Pro Asp His Glu Lys Pro Asn Cys Ala Ser Val Thr Arg Glu Leu
 50                  55                  60
Gln Val Pro Leu Ile Asp Leu Ser Gly Val Leu Ser Asn Asp Pro Ile
 65                  70                  75                  80
Glu Ile Lys Lys Ala Thr Arg Leu Val Asn Glu Ala Cys Thr Lys His
                 85                  90                  95
Gly Phe Phe Leu Val Thr Asn His Gly Val Asp Thr Asn Leu Ile Lys
                100                 105                 110
Lys Ala His Val Tyr Ile Asp Lys Phe Phe Glu Leu Pro Leu Cys Glu
            115                 120                 125
Lys Gln Lys Ala Gln Arg Arg Val Gly Glu His Cys Gly Tyr Ala Ser
130                 135                 140
Ser Phe Ile Gly Arg Phe Ser Ser Lys Leu Pro Trp Lys Glu Thr Leu
145                 150                 155                 160
Ser Phe Gln Tyr Ser Asp Glu Lys Gly Ser His Ile Val Glu Gln
                165                 170                 175
Tyr Phe Gln Arg Thr Leu Gly Glu Lys Phe Ser His Ile Gly Lys Ile
            180                 185                 190
Tyr Gln Glu Tyr Cys Asn Ala Met Ser Thr Leu Ser Leu Gly Ile Met
        195                 200                 205
Glu Leu Leu Gly Leu Ser Leu Gly Val Ser Lys Asn His Phe Lys Glu
210                 215                 220
Phe Phe Gln Glu Asn Glu Ser Ile Met Arg Leu Asn Tyr Tyr Pro Thr
225                 230                 235                 240
Cys Gln Lys Pro Glu Leu Thr Leu Gly Thr Gly Pro His Cys Asp Pro
                245                 250                 255
Thr Ser Leu Thr Ile Leu His Gln Asp Ser Val Gly Gly Leu Gln Val
            260                 265                 270
Phe Val Asp Asn Glu Trp His Ser Ile Thr Pro Asn Phe Asn Ala Phe
        275                 280                 285
Val Val Asn Ile Gly Asp Thr Phe Met Ala Leu Ser Asn Gly Arg Tyr
    290                 295                 300
Lys Ser Cys Leu His Arg Ala Leu Val Asn Asn Lys Val Pro Arg Lys
305                 310                 315                 320
Ser Leu Thr Phe Phe Leu Cys Pro Lys Lys Asp Lys Val Val Thr Pro
                325                 330                 335
Pro Ile Glu Leu Val Asp Ser Asn Asn Pro Arg Ile Tyr Pro Asp Phe
            340                 345                 350
Thr Trp Pro Thr Leu Leu Glu Phe Thr Gln Lys Gln Tyr Arg Ala Asp
        355                 360                 365
Met Asn Thr Leu Gln Thr Phe Ser Asn Trp Leu Lys Lys Thr His Pro
    370                 375                 380
```

<210> SEQ ID NO 30
<211> LENGTH: 376
<212> TYPE: PRT
<213> ORGANISM: Solanum dulcamara

<400> SEQUENCE: 30

```
Met Ala Ile Asp Cys Met Ile Thr Asn Gly Lys Ser Pro Met Leu Asp
  1               5                  10                  15
Glu Lys Lys Thr Leu Ile Phe Asp Ala Ser His Met Lys Arg Glu Ser
             20                  25                  30
```

```
Asn Ile Pro Thr Gln Phe Ile Trp Pro Asp His Glu Lys Pro Cys Ala
         35                  40                  45

Val Ala Gln Gln Leu Ala Val Pro Leu Ile Asp Leu Arg Gly Phe Leu
 50                  55                  60

Ser Gly Asp Ser Asp Ala Gln Gln Ala Ser Lys Leu Val Gly Glu
 65                  70                  75                  80

Ala Cys Arg Ser His Gly Phe Phe Leu Val Val Asn His Gly Val Glu
                 85                  90                  95

Ala Asn Leu Ile Ser Asn Ala His Arg Tyr Met Asp Thr Phe Phe Asp
            100                 105                 110

Leu Pro Leu Ser Glu Lys Gln Lys Ala Gln Arg Lys Ile Gly Glu His
        115                 120                 125

Cys Gly Tyr Ala Ser Ser Phe Thr Gly Arg Phe Ser Ser Lys Leu Pro
    130                 135                 140

Trp Lys Glu Thr Leu Ser Phe Arg Tyr Ser Ala Glu Glu Asn Ser Ser
145                 150                 155                 160

His Ile Val Glu Glu Tyr Phe Gln Arg Thr Leu Gly Glu Ser Phe Asn
                165                 170                 175

His Leu Gly Asn Val Tyr Gln Glu Tyr Cys Asn Ser Met Asn Thr Leu
            180                 185                 190

Ser Leu Gly Ile Met Glu Leu Leu Gly Met Ser Leu Gly Val Glu Lys
        195                 200                 205

Ser His Phe Lys Glu Phe Phe Glu Glu Asn Asp Ser Ile Met Arg Leu
    210                 215                 220

Asn Tyr Tyr Pro Pro Cys Gln Lys Pro Glu Leu Thr Leu Gly Thr Gly
225                 230                 235                 240

Pro His Cys Asp Pro Thr Ser Leu Thr Ile Leu His Gln Asp Cys Val
                245                 250                 255

Gly Gly Leu Gln Val Phe Val Asp Asp Glu Trp Arg Ser Ile Thr Pro
            260                 265                 270

Thr Phe Asn Ala Phe Val Val Asn Ile Gly Asp Thr Phe Met Ala Leu
        275                 280                 285

Ser Asn Gly Arg Tyr Lys Ser Cys Leu His Arg Ala Val Val Asn Asn
    290                 295                 300

Lys Thr Pro Arg Lys Ser Leu Ala Phe Phe Leu Cys Pro Asn Lys Asp
305                 310                 315                 320

Lys Val Val Ser Pro Pro Asn Glu Leu Val Asp Ser Asn Asn Pro Arg
                325                 330                 335

Ile Tyr Pro Asp Phe Thr Trp Pro Thr Leu Leu Glu Phe Thr Gln Lys
            340                 345                 350

His Tyr Arg Ala Asp Met Asn Thr Leu Gln Thr Phe Ser Asn Trp Leu
        355                 360                 365

Gln His Asn Thr Thr Ala Gln Leu
    370                 375

<210> SEQ ID NO 31
<211> LENGTH: 225
<212> TYPE: PRT
<213> ORGANISM: Solanum dulcamara

<400> SEQUENCE: 31

Leu Ser Phe Gln Tyr Ser Asp Glu Glu Gly Ser Ser His Ile Val Glu
 1                   5                  10                  15

Asp Tyr Phe Gln Arg Thr Met Gly Glu Lys Phe Ser His Leu Gly Lys
                 20                  25                  30
```

```
Val Tyr Gln Asp Tyr Cys Asn Ala Met Ser Thr Leu Ser Leu Arg Ile
                 35                  40                  45

Met Glu Leu Leu Gly Leu Ser Leu Gly Val Ser Arg Asn His Phe Lys
 50                  55                  60

Glu Phe Phe Gln Glu Asn Glu Ser Ile Met Arg Leu Asn Tyr Tyr Pro
 65                  70                  75                  80

Thr Cys Gln Lys Pro Glu Leu Thr Leu Gly Thr Gly Pro His Cys Asp
                 85                  90                  95

Pro Thr Ser Leu Thr Ile Leu His Gln Asp Ser Val Gly Gly Leu Gln
                100                 105                 110

Val Phe Val Asp Asn Glu Trp His Ser Ile Thr Pro Asn Phe Asn Ala
                115                 120                 125

Phe Val Val Asn Ile Gly Asp Thr Phe Met Ala Leu Ser Asn Gly Arg
                130                 135                 140

Tyr Lys Ser Cys Leu His Arg Ala Val Asn Asn Lys Ile Pro Arg
145                 150                 155                 160

Lys Ser Leu Ala Phe Phe Leu Cys Pro Lys Lys Asp Lys Val Val Thr
                165                 170                 175

Pro Pro Ile Glu Leu Val Asp Ser Asn Asn Pro Arg Ile Tyr Pro Asp
                180                 185                 190

Phe Thr Trp Pro Asp Leu Leu Glu Phe Thr Gln Lys Gln Tyr Arg Ala
                195                 200                 205

Asp Met Asn Thr Leu Gln Thr Phe Ser Ile Trp Leu Gln Lys Thr Gln
                210                 215                 220

Val
225

<210> SEQ ID NO 32
<211> LENGTH: 271
<212> TYPE: PRT
<213> ORGANISM: Solanum tuberosum

<400> SEQUENCE: 32

Ala Gln Val Tyr Ile Asp Lys Phe Phe Glu Leu Pro Leu Cys Glu Lys
  1               5                  10                  15

Gln Lys Ala Gln Arg Arg Val Gly Glu His Cys Gly Tyr Ala Ser Ser
                 20                  25                  30

Phe Ile Gly Gly Phe Ser Ser Lys Leu Pro Trp Lys Glu Thr Leu Ser
                 35                  40                  45

Phe Gln Tyr Ser Asp Glu Glu Gly Ser Ser His Ile Val Glu Gln Tyr
 50                  55                  60

Phe Gln Arg Thr Leu Gly Glu Gln Phe Ser Tyr Ile Gly Lys Ile Tyr
 65                  70                  75                  80

Gln Glu Tyr Cys Asn Ala Met Ser Thr Leu Ser Leu Gly Ile Met Glu
                 85                  90                  95

Leu Leu Gly Leu Ser Leu Gly Val Ser Lys Asn His Phe Lys Glu Phe
                100                 105                 110

Phe Gln Glu Asn Glu Ser Ile Met Arg Leu Asn Tyr Tyr Pro Thr Cys
                115                 120                 125

Gln Lys Pro Glu Leu Thr Leu Gly Thr Gly Pro His Cys Asp Pro Thr
                130                 135                 140

Ser Leu Thr Ile Leu His Gln Asp Ser Val Gly Gly Leu Gln Val Phe
145                 150                 155                 160

Val Asp Asn Glu Trp His Ser Ile Thr Pro Asn Phe Asn Ala Phe Val
```

```
                165                 170                 175
Val Asn Ile Gly Asp Thr Phe Met Ala Leu Ser Asn Gly Arg Tyr Lys
            180                 185                 190

Ser Cys Leu His Arg Ala Leu Val Asn Asn Lys Val Pro Arg Lys Ser
            195                 200                 205

Leu Thr Phe Phe Leu Cys Pro Lys Lys Asp Lys Val Val Thr Pro Pro
            210                 215                 220

Ile Glu Leu Val Asp Ser Asn Asn Pro Arg Ile Tyr Pro Asp Phe Thr
225                 230                 235                 240

Trp Pro Thr Leu Leu Glu Phe Thr Gln Lys Gln Tyr Arg Ala Asp Met
                245                 250                 255

Asn Thr Leu Gln Thr Phe Ser Asn Trp Leu Lys Lys Thr His Pro
            260                 265                 270

<210> SEQ ID NO 33
<211> LENGTH: 375
<212> TYPE: PRT
<213> ORGANISM: Solanum tuberosum

<400> SEQUENCE: 33

Met Ala Ile Asp Cys Met Val Met Pro Met Ile Gln Thr Ser Ser Asp
  1               5                  10                  15

Glu Lys Asn Pro Leu Ile Phe Asp Ser Ser Val Leu Lys His Glu Ser
             20                  25                  30

Asn Ile Pro Arg Gln Phe Ile Trp Pro Asp His Glu Lys Pro Ser Gly
         35                  40                  45

Gly Val Pro Glu Leu Asp Val Pro Leu Ile Asp Leu Gly Ala Phe Leu
     50                  55                  60

Ser Gly Asp Pro Ile Ala Ala Lys Arg Glu Ser Arg Leu Val Asp Glu
65                  70                  75                  80

Ala Cys Lys Asn His Gly Phe Phe Leu Val Gly Asn His Gly Val Asp
                 85                  90                  95

Thr Asn Leu Ile Ser Leu Ala His Arg Tyr Met Asn Met Phe Phe Glu
            100                 105                 110

Leu Pro Leu Ser Asn Lys Gln Met Ile Gln Arg Lys Arg Gly Asp His
            115                 120                 125

Cys Gly Tyr Ala Ser Ser Phe Thr Glu Arg Phe Ser Ser Lys Leu Pro
        130                 135                 140

Trp Lys Glu Thr Leu Ser Phe Ser Tyr Ser Ala Leu Gln Gly Ser Ser
145                 150                 155                 160

His Met Val Asp Gln Tyr Phe Leu Lys Thr Met Gly Glu Asp Phe Ser
                165                 170                 175

His Ile Gly Lys Phe Tyr Gln Glu Tyr Cys Asn Ala Met Ser Thr Leu
            180                 185                 190

Ser Ser Gly Ile Met Glu Leu Leu Gly Glu Ser Leu Gly Val Ser Lys
        195                 200                 205

Asn His Phe Lys Gln Phe Phe Glu Glu Asn Glu Ser Ile Met Arg Leu
    210                 215                 220

Asn Tyr Tyr Pro Thr Cys Gln Lys Pro Asp Leu Ala Leu Gly Thr Gly
225                 230                 235                 240

Pro His Cys Asp Pro Thr Ser Leu Thr Ile Leu His Gln Asp Ser Val
                245                 250                 255

Ser Gly Leu Gln Val Phe Met Asp Asn Gln Trp Arg Ser Ile Ser Pro
            260                 265                 270
```

```
Asn Leu Ser Ala Phe Val Val Asn Ile Gly Asp Thr Phe Met Ala Leu
            275                 280                 285

Ser Asn Gly Arg Tyr Lys Ser Cys Leu His Arg Ala Val Asn Asn
    290                 295                 300

Lys Thr Pro Arg Lys Ser Leu Ala Phe Phe Leu Cys Pro Lys Lys Asp
305                 310                 315                 320

Lys Val Val Arg Pro Pro Ala Glu Leu Val Asp Ser Asn Asn Pro Arg
                325                 330                 335

Ile Tyr Pro Asp Phe Thr Trp Pro Thr Leu Leu Glu Phe Thr Gln Lys
                340                 345                 350

His Tyr Arg Ala Asp Thr Asn Thr Leu Gln Phe Phe Ser Asn Trp Leu
            355                 360                 365

Gln Gln Arg Thr Thr Glu Val
    370                 375

<210> SEQ ID NO 34
<211> LENGTH: 378
<212> TYPE: PRT
<213> ORGANISM: Solanum tuberosum

<400> SEQUENCE: 34

Met Ala Ile Asp Cys Met Ile Thr Asn Ala Lys Ser Pro Met Ile Asp
  1               5                  10                  15

Glu Thr Lys Gln Phe Ile Phe Asp Ala Ser His Met Lys Arg Glu Ser
                 20                  25                  30

Asn Ile Pro Thr Gln Phe Ile Trp Pro Asp His Glu Lys Pro Cys Ala
             35                  40                  45

Val Val Gln Glu Leu His Val Pro Leu Ile Asp Leu Arg Gly Phe Leu
         50                  55                  60

Ser Gly Asp Ser Asp Ala Ala Gln Gln Ala Ser Lys Leu Val Gly Glu
 65                  70                  75                  80

Ala Cys Arg Ser His Gly Phe Phe Leu Val Val Asn His Gly Val Asp
                 85                  90                  95

Ala Asn Leu Ile Ser Asn Ala His Arg Tyr Met Asp Thr Phe Phe Asp
            100                 105                 110

Leu Pro Leu Leu Glu Lys Gln Lys Ala Gln Arg Lys Ile Gly Glu His
        115                 120                 125

Cys Gly Tyr Ala Ser Ser Phe Thr Gly Arg Phe Ser Ser Lys Leu Pro
130                 135                 140

Trp Lys Glu Thr Leu Ser Phe Arg Tyr Ser Ala Glu Glu Glu Ser Ser
145                 150                 155                 160

His Ile Val Glu Asp Ile Phe Lys Gly His Trp Val Lys Ile Leu Thr
                165                 170                 175

Ile Leu Gly Asn Val Tyr Gln Glu Tyr Cys Asn Ser Lys Asn Thr Leu
            180                 185                 190

Ser Leu Gly Ile Met Glu Leu Leu Gly Met Ser Leu Gly Val Glu Lys
        195                 200                 205

Ser His Phe Lys Glu Phe Phe Glu Glu Asn Asp Ser Ile Met Arg Leu
    210                 215                 220

Asn Tyr Tyr Pro Pro Cys Gln Lys Pro Glu Leu Thr Leu Gly Thr Gly
225                 230                 235                 240

Pro His Cys Asp Pro Thr Ser Leu Thr Ile Leu His Gln Asp Cys Val
                245                 250                 255

Gly Gly Leu Gln Val Phe Val Asp Asp Glu Trp Arg Ser Ile Ser Pro
            260                 265                 270
```

```
Asn Phe Asn Ala Phe Val Val Asn Ile Gly Asp Thr Phe Met Ala Leu
        275                 280                 285

Ser Asn Gly Arg Tyr Lys Ser Cys Leu His Arg Ala Val Val Asn Asn
        290                 295                 300

Lys Thr Pro Arg Lys Ser Leu Ala Phe Phe Leu Cys Pro Asn Lys Asp
305                 310                 315                 320

Lys Val Val Ser Pro Asn Glu Leu Val Asp Ser Asn Asn Pro Arg
                325                 330                 335

Ile Tyr Pro Asp Phe Thr Trp Pro Thr Leu Leu Glu Phe Thr Gln Lys
        340                 345                 350

His Tyr Arg Ala Asp Met Asn Thr Leu Gln Thr Phe Ser Asn Trp Val
        355                 360                 365

His Asp Gln His Asn Thr Lys Thr Gln Val
        370                 375

<210> SEQ ID NO 35
<211> LENGTH: 66
<212> TYPE: PRT
<213> ORGANISM: Eustoma grandiflorum

<400> SEQUENCE: 35

Gly Thr Gly Pro His Cys Asp Pro Thr Ser Leu Thr Ile Leu His Gln
1               5                   10                  15

Asp Ser Val Gly Gly Leu Gln Val Phe Val Asp Asp Glu Trp Arg Ser
            20                  25                  30

Ile Ser Pro Asn Ala Gly Ala Phe Val Val Asn Ile Gly Asp Thr Phe
        35                  40                  45

Met Ala Leu Ser Asn Gly Arg Tyr Lys Ser Cys Leu His Arg Ala Val
    50                  55                  60

Val Asn
65

<210> SEQ ID NO 36
<211> LENGTH: 383
<212> TYPE: PRT
<213> ORGANISM: Citrus sinensis

<400> SEQUENCE: 36

Met Ala Ile Asp Cys Ile Lys Asn Ile Pro Thr Met Leu His Gln Pro
1               5                   10                  15

Lys Glu Glu Tyr Lys Asp Glu Gln Lys Pro Leu Val Phe Asp Ala Ser
            20                  25                  30

Val Leu Lys His Gln Thr Gln Ile Pro Lys Gln Phe Ile Trp Pro Asp
        35                  40                  45

Asp Glu Lys Pro Cys Val Asn Ala Pro Glu Leu Gln Val Pro Leu Ile
    50                  55                  60

Asp Leu Gly Gly Phe Leu Ser Asp Asp Pro Val Ala Ala Lys Glu Ala
65                  70                  75                  80

Ser Arg Leu Val Gly Glu Ala Cys Arg Lys His Gly Phe Phe Leu Val
            85                  90                  95

Val Asn His Gly Val Asp Ser Ser Leu Ile Ala Asp Ala His Arg Tyr
        100                 105                 110

Met Asp His Phe Phe Glu Leu Pro Leu Asn Glu Lys Gln Arg Ala Arg
        115                 120                 125

Arg Lys Leu Gly Glu His Cys Gly Tyr Ala Ser Ser Phe Thr Gly Arg
        130                 135                 140
```

```
Phe Ser Ser Lys Leu Pro Trp Lys Glu Thr Leu Ser Phe Arg Tyr Ser
145                 150                 155                 160

Ala Glu Lys Ser Leu Ser Asn Asn Ile Val Glu Asp Tyr Leu Leu Asn
                165                 170                 175

Thr Met Gly Asp Glu Phe Lys Gln Phe Gly Arg Val Tyr Gln Asp Tyr
            180                 185                 190

Cys Glu Ser Met Ser Arg Leu Ser Leu Gly Ile Met Glu Leu Leu Ala
            195                 200                 205

Ile Ser Leu Gly Val Gly Arg Ala His Phe Lys Glu Phe Phe Glu Glu
        210                 215                 220

Asn Asp Ser Ile Met Arg Leu Asn Tyr Tyr Pro Pro Cys Gln Lys Pro
225                 230                 235                 240

Glu Leu Thr Leu Gly Thr Gly Pro His Cys Asp Pro Thr Ser Leu Thr
                245                 250                 255

Ile Leu His Gln Asp Gln Val Gly Gly Leu Gln Val Phe Val Asp Asn
            260                 265                 270

Glu Trp Arg Ser Ile Ser Pro Asn Phe Glu Ala Phe Val Val Asn Ile
        275                 280                 285

Gly Asp Thr Phe Met Ala Leu Ser Asn Gly Arg Tyr Lys Ser Cys Leu
290                 295                 300

His Arg Ala Val Val Asn Ser Gln Thr Thr Arg Lys Ser Leu Ala Phe
305                 310                 315                 320

Phe Leu Cys Pro Lys Asn Asp Lys Val Val Ser Pro Ser Glu Leu
                325                 330                 335

Val Asp Thr Tyr Ser Ser Pro Arg Ile Tyr Pro Asp Phe Thr Trp Pro
            340                 345                 350

Met Leu Leu Glu Phe Thr Gln Lys His Tyr Arg Ala Asp Met Lys Thr
        355                 360                 365

Leu Glu Ala Phe Thr Asn Trp Leu Gln Gln Lys Lys Gln Leu Lys
370                 375                 380

<210> SEQ ID NO 37
<211> LENGTH: 374
<212> TYPE: PRT
<213> ORGANISM: Spinacia oleracea

<400> SEQUENCE: 37

Met Met Gln Pro Leu Leu Thr Ile Pro Pro Leu Pro Thr Thr Ser
1               5                   10                  15

Leu Phe Asp Thr Ser Phe Leu Lys His Glu Asp Asn Ile Pro Ser Gln
            20                  25                  30

Phe Ile Trp Pro Asp Asp Glu Lys Pro Cys Ser Glu Thr Pro Pro Glu
        35                  40                  45

Leu Glu Val Pro Pro Ile Asp Leu Gly Gly Phe Leu Ser Gly Asp Pro
    50                  55                  60

Val Ala Val Ser Lys Ala Thr Thr Leu Ala Asn Glu Ala Cys Lys Trp
65                  70                  75                  80

His Gly Phe Phe Leu Ile Val Asn His Asp Ile Tyr Phe Glu Leu Leu
                85                  90                  95

Val Lys Ala His Glu Ala Met Asp Tyr Phe Phe Ser Gln Pro Phe Ser
            100                 105                 110

Gln Lys Gln Lys Ala Leu Arg Lys Gln Gly Asp His Cys Gly Tyr Ala
        115                 120                 125

Ser Ser Phe Leu Gly Arg Phe Ala Thr Lys Leu Pro Trp Lys Glu Thr
```

```
            130                 135                 140
Leu Ser Phe Arg Tyr Tyr Asp Asp Asp Asp Lys Ser Ser Lys Met
145                 150                 155                 160

Val Gln Asn Tyr Ile Ser Asn Leu Met Gly Thr Asp Phe Gln Glu Phe
                165                 170                 175

Gly Arg Val Tyr Gln Glu Tyr Cys Lys Ala Met Ser Lys Leu Ser Leu
            180                 185                 190

Gly Ile Met Glu Leu Leu Gly Met Ser Leu Gly Val Gly Arg Asn Tyr
            195                 200                 205

Phe Arg Glu Phe Phe Lys Gly Asn Asp Ser Ile Ile Arg Leu Asn Tyr
    210                 215                 220

Tyr Pro Pro Cys Gln Lys Pro Glu Leu Thr Leu Gly Thr Gly Pro His
225                 230                 235                 240

Cys Asp Pro Thr Ser Leu Thr Ile Leu His Gln Asp His Val Gly Gly
                245                 250                 255

Leu Glu Val Phe Val Asp Gln Lys Trp Tyr Ser Ile Arg Pro Asn Gln
            260                 265                 270

Lys Ala Phe Val Val Asn Ile Gly Asp Thr Phe Met Ala Leu Ser Asn
        275                 280                 285

Gly Lys Tyr Lys Ser Cys Leu His Arg Ala Val Val Asn Ser Lys Thr
    290                 295                 300

Pro Arg Lys Ser Val Ala Phe Phe Leu Cys Pro Arg Gly Asn Lys Val
305                 310                 315                 320

Ile Arg Pro Pro Ile Glu Leu Gly His Pro Arg Val Tyr Pro Asp Phe
                325                 330                 335

Thr Trp Pro Leu Leu Leu Glu Phe Thr Gln Lys His Tyr Arg Ala Asp
            340                 345                 350

Thr Lys Thr Leu Asp Ser Phe Thr Lys Trp Leu Gln Lys Arg Ser Thr
        355                 360                 365

Glu Asp Glu Arg Val Lys
    370

<210> SEQ ID NO 38
<211> LENGTH: 382
<212> TYPE: PRT
<213> ORGANISM: Vitis vinifera

<400> SEQUENCE: 38

Met Ser Ile Val Cys Val Glu Gly Asn Pro Pro Ser Met Phe Asn Pro
1               5                   10                  15

Pro Thr Asp Asp His Lys Asn Gln Glu Pro Leu Val Phe Asp Ala Ser
            20                  25                  30

Val Leu Arg His Gln Ser Asn Ile Pro Lys Gln Phe Ile Trp Pro Asp
        35                  40                  45

Ala Glu Lys Pro Gly Asp Lys Ala Thr Glu Leu Ser Val Pro Leu Ile
    50                  55                  60

Asp Leu Gly Gly Phe Leu Ser Gly Asp Pro Ala Ala Ala Met Glu Ala
65                  70                  75                  80

Thr Arg Leu Val Arg Glu Ala Cys Gln Lys His Gly Phe Phe Leu Val
                85                  90                  95

Val Asn His Gly Val Asp Asp Lys Leu Ile Tyr Lys Ala His Gln Tyr
            100                 105                 110

Met Asp Ser Phe Phe Gly Leu Pro Leu Ala Lys Lys Gln Arg Ala Gln
        115                 120                 125
```

```
Arg Lys Leu Gly Glu His Cys Gly Tyr Ala Ser Ser Phe Ile Gly Arg
            130                 135                 140

Phe Ser Ser Lys Leu Pro Trp Lys Glu Thr Leu Ser Phe Ser Tyr Ser
145                 150                 155                 160

Ala Glu Lys Lys Ser Ser Asn Ala Val Gln Glu Tyr Phe Leu Asn Lys
                165                 170                 175

Met Gly Glu Asp Phe Ser Glu Phe Gly Gln Val Tyr Gln Asp Tyr Cys
            180                 185                 190

Glu Ala Met Ser Thr Leu Ser Leu Val Ile Met Glu Leu Leu Gly Met
            195                 200                 205

Ser Leu Gly Ile Gly Gly Ala His Phe Arg Glu Phe Phe Glu Glu Asn
210                 215                 220

Asp Ser Ile Met Arg Leu Asn Tyr Tyr Pro Pro Cys Leu Lys Pro Asp
225                 230                 235                 240

Leu Thr Leu Gly Thr Gly Pro His Cys Asp Pro Thr Ser Leu Thr Ile
            245                 250                 255

Leu His Gln Asp Gln Val Gly Gly Leu Gln Val Phe Val Asp Asp Lys
            260                 265                 270

Trp Trp Ser Ile Ser Pro Asn Phe Asp Ala Phe Val Val Asn Ile Gly
            275                 280                 285

Asp Thr Phe Met Ala Leu Ser Asn Gly Arg Tyr Lys Ser Cys Leu His
290                 295                 300

Arg Ala Val Val Asn Ser Gln Thr Pro Arg Lys Ser Leu Ala Phe Phe
305                 310                 315                 320

Leu Cys Pro Glu Lys Asp Lys Val Val Arg Pro Thr Glu Leu Val
            325                 330                 335

Asp Thr Asn Ser Pro Arg Ile Tyr Pro Asp Phe Thr Trp Ser Asn Leu
            340                 345                 350

Leu Glu Phe Thr Gln Lys His Tyr Arg Ala Asp Met Lys Thr Leu Glu
            355                 360                 365

Val Phe Ser Ser Trp Leu Gln Gln Lys Thr Ala Glu Ala Gly
            370                 375                 380

<210> SEQ ID NO 39
<211> LENGTH: 385
<212> TYPE: PRT
<213> ORGANISM: Populus tremula x tremuloides

<400> SEQUENCE: 39

Met Ala Ile Asp Cys Ile Lys Thr Met Pro Ser Ile Thr Thr Pro His
1               5                   10                  15

His His Pro Lys Asp Gln Asp Gln Cys Lys Asp Asp Gly Lys Ser Phe
            20                  25                  30

Val Phe Asp Ala Gln Val Leu Arg His Gln Thr Asn Ile Pro Gln Gln
        35                  40                  45

Phe Ile Trp Pro Asp Asn Glu Lys Pro Asn Ile Asn Ala Pro Glu Leu
    50                  55                  60

Gln Val Pro Leu Val Asp Leu Gly Asp Phe Leu Ser Gly Asn Pro Val
65                  70                  75                  80

Ala Ala Val Glu Ala Ser Arg Leu Val Gly Glu Ala Cys Lys Lys His
                85                  90                  95

Gly Phe Phe Leu Val Val Asn His Gly Val Asp Lys Thr Leu Ile Ala
            100                 105                 110

His Ala His Asn Tyr Val Asp Thr Phe Phe Lys Leu Pro Leu Ser Glu
        115                 120                 125
```

```
Lys Gln Lys Ala Gln Arg Lys Ile Gly Glu Ser Cys Gly Tyr Ala Ser
        130                 135                 140

Ser Phe Thr Gly Arg Phe Ser Ser Lys Leu Pro Trp Lys Glu Thr Leu
145                 150                 155                 160

Ser Phe Arg Tyr Lys Ala Glu Glu Asn Ser Ser Lys His Ile Glu Glu
                165                 170                 175

Tyr Phe His Asn Arg Met Gly Glu Asp Phe Ala Glu Phe Gly Thr Val
            180                 185                 190

Tyr Gln Asp Tyr Cys Glu Ala Met Ser Thr Leu Ser Leu Gly Ile Met
        195                 200                 205

Glu Leu Leu Gly Met Ser Leu Gly Val Ser Arg Glu His Phe Arg Glu
210                 215                 220

Phe Phe Asn Glu Asn Asp Ser Ile Met Arg Leu Asn Tyr Tyr Pro Pro
225                 230                 235                 240

Cys Gln Lys Pro Asp Leu Thr Leu Gly Thr Gly Pro His Cys Asp Pro
                245                 250                 255

Thr Ser Leu Thr Ile Leu His Gln Asp Gln Val Gly Gly Leu Gln Val
            260                 265                 270

Phe Val Asp Asn Glu Trp Arg Ser Ile Asn Pro Asn Phe Asp Ala Phe
        275                 280                 285

Val Val Asn Ile Gly Asp Thr Phe Met Ala Leu Ser Asn Gly Ile Tyr
290                 295                 300

Lys Ser Cys Leu His Arg Ala Val Val Asn Ser Gln Thr Pro Arg Lys
305                 310                 315                 320

Ser Leu Ala Phe Phe Leu Cys Pro Lys Asn Asp Lys Met Val Thr Pro
                325                 330                 335

Pro His Glu Leu Val Asp Thr Cys Asn Pro Arg Ile Tyr Pro Asp Phe
            340                 345                 350

Thr Trp Pro Met Leu Leu Glu Phe Thr Gln Lys His Tyr Arg Ala Asp
        355                 360                 365

Met Lys Thr Leu Glu Val Phe Thr Asn Trp Leu His Gln Arg Ser Phe
    370                 375                 380

Ser
385

<210> SEQ ID NO 40
<211> LENGTH: 385
<212> TYPE: PRT
<213> ORGANISM: Populus tomentosa

<400> SEQUENCE: 40

Met Ala Ile Asp Cys Ile Lys Thr Met Pro Ser Ile Thr Thr Pro Gln
1               5                   10                  15

His His Pro Lys Asp Gln Asp Gln Cys Lys Asp Asp Gly Lys Ser Phe
                20                  25                  30

Val Phe Asp Ala Gln Ile Leu Arg His Gln Thr Asn Ile Pro Gln Gln
            35                  40                  45

Phe Val Trp Pro Asp His Glu Lys Pro Asn Ile Asn Ala Pro Glu Leu
        50                  55                  60

Gln Val Pro Leu Val Asp Leu Gly Asp Phe Leu Ser Gly Asn Pro Val
65                  70                  75                  80

Ala Ala Val Glu Ala Ser Arg Leu Val Gly Glu Ala Cys Lys Lys His
                85                  90                  95

Gly Phe Phe Leu Val Val Asn His Gly Val Asp Lys Thr Leu Ile Ala
```

```
                100                 105                 110
His Ala His Asn Tyr Val Asp Thr Phe Phe Lys Leu Pro Leu Ser Glu
        115                 120                 125

Lys Gln Lys Ala Gln Arg Lys Ile Gly Glu Ser Cys Gly Tyr Ala Ser
    130                 135                 140

Ser Phe Thr Gly Arg Phe Ser Ser Lys Leu Pro Trp Lys Glu Thr Leu
145                 150                 155                 160

Ser Phe Arg Tyr Thr Ala Glu Glu Asn Ser Ser Lys His Ile Glu Glu
                165                 170                 175

Tyr Phe His Asn Arg Met Gly Glu Asp Phe Ala Glu Phe Gly Thr Val
            180                 185                 190

Tyr Gln Asp Tyr Cys Glu Ala Met Ser Thr Leu Ser Leu Gly Ile Met
        195                 200                 205

Glu Leu Leu Gly Met Ser Leu Gly Val Ser Arg Glu His Phe Arg Glu
    210                 215                 220

Phe Phe Asn Glu Asn Asp Ser Ile Met Arg Leu Asn Tyr Tyr Pro Pro
225                 230                 235                 240

Cys Gln Lys Pro Asp Leu Thr Leu Gly Thr Gly Pro His Cys Asp Pro
                245                 250                 255

Thr Ser Leu Thr Ile Leu His Gln Asp Gln Val Gly Gly Leu Gln Val
            260                 265                 270

Phe Val Asp Asn Glu Trp Arg Ser Ile Asn Pro Asn Phe Asp Ala Phe
        275                 280                 285

Val Val Asn Ile Gly Asp Thr Phe Met Ala Leu Ser Asn Gly Ile Tyr
    290                 295                 300

Lys Ser Cys Leu His Arg Ala Val Val Asn Gly Gln Thr Pro Arg Lys
305                 310                 315                 320

Ser Leu Ala Phe Phe Leu Cys Pro Lys Asn Asp Lys Met Val Thr Pro
                325                 330                 335

Pro His Glu Leu Val Asp Thr Cys Asn Pro Arg Ile Tyr Pro Asp Phe
            340                 345                 350

Thr Trp Pro Met Leu Leu Glu Phe Thr Gln Lys His Tyr Arg Ala Asp
        355                 360                 365

Met Lys Thr Leu Glu Val Phe Thr Asn Trp Leu His Gln Arg Ser Phe
    370                 375                 380

Thr
385

<210> SEQ ID NO 41
<211> LENGTH: 385
<212> TYPE: PRT
<213> ORGANISM: Populus nigra

<400> SEQUENCE: 41

Met Ala Ile Asp Cys Ile Lys Thr Met Pro Ser Ile Thr Thr Pro His
  1               5                  10                  15

His His Pro Lys Asp Gln Asp Gln Cys Lys Asp Asp Gly Lys Ser Phe
                 20                  25                  30

Val Phe Asp Ala Gln Val Leu Arg His Gln Thr Asn Ile Pro Gln Gln
             35                  40                  45

Phe Ile Trp Pro Asp His Glu Lys Pro Asn Ile Asn Ala Pro Glu Leu
         50                  55                  60

Gln Val Pro Leu Val Asp Leu Gly Asp Phe Leu Ser Gly Asn Pro Val
65                  70                  75                  80
```

Ala Ala Val Glu Ala Ser Arg Leu Val Gly Glu Ala Cys Gln Lys His
            85                  90                  95

Gly Phe Phe Leu Val Val Asn His Gly Val Asp Lys Thr Leu Ile Ala
            100                 105                 110

His Ala His Asn Tyr Met Asp Thr Phe Phe Glu Leu Pro Leu Ser Glu
            115                 120                 125

Lys Gln Lys Ala Gln Arg Lys Ile Gly Glu Ser Cys Gly Tyr Ala Ser
130                 135                 140

Ser Phe Thr Gly Arg Phe Ser Ser Lys Leu Pro Trp Lys Glu Thr Leu
145                 150                 155                 160

Ser Phe Arg Tyr Thr Ala Glu Lys Asn Ser Lys His Ile Glu Glu
                    165                 170                 175

Tyr Phe His Asn Arg Met Gly Glu Asp Phe Ala Glu Phe Gly Arg Val
                180                 185                 190

Tyr Gln Asp Tyr Cys Glu Ala Met Ser Thr Leu Ser Leu Gly Ile Met
                195                 200                 205

Glu Leu Leu Gly Met Ser Leu Gly Val Ser Arg Glu His Phe Arg Glu
            210                 215                 220

Phe Phe Asn Glu Asn Asp Ser Ile Met Arg Leu Asn Tyr Tyr Pro Pro
225                 230                 235                 240

Cys Gln Lys Pro Asp Leu Thr Leu Gly Thr Gly Pro His Cys Asp Pro
                245                 250                 255

Thr Ser Leu Thr Ile Leu His Gln Asp Gln Val Gly Gly Leu Gln Val
                260                 265                 270

Phe Val Asp Asn Glu Trp Arg Ser Ile Ser Pro Asn Phe Asp Ala Phe
            275                 280                 285

Val Val Asn Ile Gly Asp Thr Phe Met Ala Leu Ser Asn Gly Ile Tyr
            290                 295                 300

Lys Ser Cys Leu His Arg Ala Val Val Asn Ser Gln Thr Pro Arg Lys
305                 310                 315                 320

Ser Leu Ala Phe Phe Leu Cys Pro Lys Asn Asp Lys Met Val Thr Pro
                325                 330                 335

Pro His Glu Leu Val Asp Thr Cys Asn Pro Arg Ile Tyr Pro Asp Phe
                340                 345                 350

Thr Trp Pro Met Leu Leu Glu Phe Thr Gln Lys His Tyr Arg Ala Asp
                355                 360                 365

Met Lys Thr Leu Glu Val Phe Thr Asn Trp Leu His Gln Gln Ser Phe
370                 375                 380

Ser
385

<210> SEQ ID NO 42
<211> LENGTH: 385
<212> TYPE: PRT
<213> ORGANISM: Populus tremula

<400> SEQUENCE: 42

Met Ala Ile Asp Cys Ile Lys Thr Met Pro Ser Ile Thr Thr Pro His
 1               5                  10                  15

His His Pro Lys Asp Gln Asp Gln Cys Lys Asp Asp Gly Lys Ser Phe
            20                  25                  30

Val Phe Asp Ala Gln Val Leu Arg His Gln Thr Asn Ile Pro Gln Gln
            35                  40                  45

Phe Ile Trp Pro Asp Asn Glu Lys Pro Asn Ile Asn Ala Pro Glu Leu
50                  55                  60

Gln Val Pro Leu Val Asp Leu Gly Asp Phe Leu Ser Gly Asn Pro Val
65                  70                  75                  80

Ala Ala Val Glu Ala Ser Arg Leu Val Gly Glu Ala Cys Lys Lys His
            85                  90                  95

Gly Phe Phe Leu Val Asn His Gly Val Asp Lys Thr Leu Ile Ala
            100                 105                 110

His Ala His Asn Tyr Val Asp Thr Phe Phe Lys Leu Pro Leu Ser Glu
        115                 120                 125

Lys Gln Lys Ala Gln Arg Lys Ile Gly Glu Ser Cys Gly Tyr Ala Ser
130                 135                 140

Ser Phe Thr Gly Arg Phe Ser Ser Lys Leu Pro Trp Lys Glu Thr Leu
145                 150                 155                 160

Ser Phe Arg Tyr Lys Ala Glu Glu Asn Ser Pro Lys His Ile Glu Glu
                165                 170                 175

Tyr Phe Arg Asn Arg Met Gly Glu Asp Phe Ala Glu Phe Gly Thr Val
            180                 185                 190

Tyr Gln Asp Tyr Cys Glu Ala Met Ser Thr Leu Ser Leu Gly Ile Met
        195                 200                 205

Glu Leu Leu Gly Met Ser Leu Gly Val Ser Arg Glu His Phe Arg Glu
210                 215                 220

Phe Phe Asn Glu Asn Asp Ser Ile Met Arg Leu Asn Tyr Tyr Pro Pro
225                 230                 235                 240

Cys Gln Lys Pro Asp Leu Thr Leu Gly Thr Gly Pro His Cys Asp Pro
                245                 250                 255

Thr Ser Leu Thr Ile Leu His Gln Asp Gln Val Gly Gly Leu Gln Val
            260                 265                 270

Phe Val Asp Asn Glu Trp Arg Ser Ile Asn Pro Asn Phe Asp Ala Phe
        275                 280                 285

Val Val Asn Ile Gly Asp Thr Phe Met Ala Leu Ser Asn Gly Ile Tyr
290                 295                 300

Lys Ser Cys Leu His Arg Ala Val Val Asn Ser Gln Thr Pro Arg Lys
305                 310                 315                 320

Ser Leu Ala Phe Phe Leu Cys Pro Lys Asn Asp Lys Met Val Thr Pro
                325                 330                 335

Pro His Glu Leu Val Asp Thr Cys Asn Pro Arg Ile Tyr Pro Asp Phe
            340                 345                 350

Thr Trp Pro Met Leu Leu Glu Phe Thr Gln Lys His Tyr Arg Ala Asp
        355                 360                 365

Met Lys Thr Leu Glu Val Phe Thr Asn Trp Leu His Gln Arg Ser Phe
370                 375                 380

Ser
385

<210> SEQ ID NO 43
<211> LENGTH: 385
<212> TYPE: PRT
<213> ORGANISM: Populus tremula

<400> SEQUENCE: 43

Met Ala Ile Asp Cys Ile Lys Thr Met Pro Ser Ile Thr Thr Pro His
1               5                   10                  15

His His Pro Lys Asp Gln Asp Gln Cys Lys Asp Asp Gly Lys Ser Phe
            20                  25                  30

Val Phe Asp Ala Gln Val Leu Arg His Gln Thr Asn Ile Pro Gln Gln

```
            35                  40                  45
Phe Ile Trp Pro Asp Asn Glu Lys Pro Asn Ile Asn Ala Pro Glu Leu
 50                  55                  60

Gln Val Pro Leu Val Asp Leu Gly Asp Phe Leu Ser Gly Asn Pro Val
 65                  70                  75                  80

Ala Ala Val Glu Ala Ser Arg Leu Val Gly Glu Ala Cys Lys Lys His
                 85                  90                  95

Gly Phe Phe Leu Val Val Asn His Gly Val Asp Lys Thr Leu Ile Ala
                100                 105                 110

His Ala His Asn Tyr Val Asp Thr Phe Phe Lys Leu Pro Leu Ser Glu
            115                 120                 125

Lys Gln Lys Ala Gln Arg Lys Ile Gly Glu Ser Cys Gly Tyr Ala Ser
130                 135                 140

Ser Phe Thr Gly Arg Phe Ser Ser Lys Leu Pro Trp Lys Glu Thr Leu
145                 150                 155                 160

Ser Phe Arg Tyr Lys Ala Glu Glu Asn Ser Ser Lys His Ile Glu Glu
                165                 170                 175

Tyr Phe His Asn Arg Met Gly Glu Asp Phe Ala Glu Phe Gly Thr Val
                180                 185                 190

Tyr Gln Asp Tyr Cys Glu Ala Met Ser Thr Leu Ser Leu Gly Ile Met
            195                 200                 205

Glu Leu Leu Gly Met Ser Leu Gly Val Ser Arg Glu His Phe Arg Glu
210                 215                 220

Phe Phe Asn Glu Asn Asp Ser Ile Met Arg Leu Asn Tyr Tyr Pro Pro
225                 230                 235                 240

Cys Gln Lys Pro Asp Leu Thr Leu Gly Thr Gly Pro His Cys Asp Pro
                245                 250                 255

Thr Ser Leu Thr Ile Leu His Gln Asp Gln Val Gly Gly Leu Gln Val
            260                 265                 270

Phe Val Asp Asn Glu Trp Arg Ser Ile Asn Pro Asn Phe Asp Ala Phe
            275                 280                 285

Val Val Asn Ile Gly Asp Thr Phe Met Ala Leu Ser Asn Gly Val Tyr
290                 295                 300

Lys Ser Cys Leu His Arg Ala Val Val Asn Ser Gln Thr Pro Arg Lys
305                 310                 315                 320

Ser Leu Ala Phe Phe Leu Cys Pro Lys Asn Asp Lys Met Val Thr Pro
                325                 330                 335

Pro His Glu Leu Val Asp Thr Cys Asn Pro Arg Ile Tyr Pro Asp Phe
            340                 345                 350

Thr Trp Pro Met Leu Leu Glu Phe Thr Gln Lys His Tyr Arg Ala Asp
            355                 360                 365

Met Lys Thr Leu Glu Val Phe Thr Asn Trp Leu His Gln Arg Ser Phe
370                 375                 380

Ser
385

<210> SEQ ID NO 44
<211> LENGTH: 385
<212> TYPE: PRT
<213> ORGANISM: Populus tremula

<400> SEQUENCE: 44

Met Ala Ile Asp Cys Ile Lys Thr Met Pro Ser Ile Thr Thr Pro His
 1               5                  10                  15
```

His His Pro Lys Asp Gln Asp Gln Cys Lys Asp Asp Gly Lys Ser Phe
            20                  25                  30

Val Phe Asp Ala Gln Val Leu Arg His Gln Thr Asn Ile Pro Gln Gln
        35                  40                  45

Phe Ile Trp Pro Asp Asn Glu Lys Pro Asn Ile Asn Ala Pro Glu Leu
50                  55                  60

Gln Val Pro Leu Val Asp Leu Gly Asp Phe Leu Ser Gly Asn Pro Val
65                  70                  75                  80

Ala Ala Val Glu Ala Ser Arg Leu Val Gly Glu Ala Cys Lys Lys His
                85                  90                  95

Gly Phe Phe Leu Val Val Asn His Gly Val Asp Lys Thr Leu Ile Ala
            100                 105                 110

His Ala His Asn Tyr Val Asp Thr Phe Phe Lys Leu Pro Leu Ser Glu
            115                 120                 125

Lys Gln Lys Ala Gln Arg Lys Ile Gly Glu Ser Cys Gly Tyr Ala Ser
130                 135                 140

Ser Phe Thr Gly Arg Phe Ser Ser Lys Leu Pro Trp Lys Glu Thr Leu
145                 150                 155                 160

Ser Phe Arg Tyr Lys Ala Glu Glu Asn Ser Ser Lys His Ile Glu Glu
                165                 170                 175

Tyr Phe His Asn Arg Met Gly Glu Asp Phe Ala Glu Phe Gly Thr Val
            180                 185                 190

Tyr Gln Asp Tyr Cys Glu Ala Met Ser Thr Leu Ser Leu Gly Ile Met
            195                 200                 205

Glu Leu Leu Gly Met Ser Leu Gly Val Ser Arg Glu His Phe Arg Glu
210                 215                 220

Phe Phe Asn Glu Asn Asp Ser Ile Met Arg Leu Asn Tyr Tyr Pro Pro
225                 230                 235                 240

Cys Gln Lys Pro Asp Leu Thr Leu Gly Thr Gly Pro His Cys Asp Pro
                245                 250                 255

Thr Ser Leu Thr Ile Leu His Gln Asp Gln Val Gly Gly Leu Gln Val
            260                 265                 270

Phe Val Asp Asn Glu Trp Arg Ser Ile Asn Pro Asn Phe Asp Ala Phe
            275                 280                 285

Val Val Asn Ile Gly Asp Thr Phe Met Ala Leu Ser Asn Gly Ile Tyr
290                 295                 300

Lys Ser Cys Leu His Arg Ala Val Val Asn Ser Gln Thr Pro Arg Lys
305                 310                 315                 320

Ser Leu Ala Phe Phe Leu Cys Pro Lys Asn Asp Lys Met Val Thr Pro
                325                 330                 335

Pro His Glu Leu Val Asp Thr Cys Asn Pro Arg Ile Tyr Pro Asp Phe
            340                 345                 350

Thr Trp Pro Met Leu Leu Glu Phe Thr Gln Lys His Tyr Arg Ala Asp
            355                 360                 365

Met Lys Thr Leu Glu Val Phe Thr Asn Trp Leu His Gln Arg Ser Phe
370                 375                 380

Ser
385

<210> SEQ ID NO 45
<211> LENGTH: 385
<212> TYPE: PRT
<213> ORGANISM: Populus tremula

<400> SEQUENCE: 45

```
Met Ala Ile Asp Cys Ile Lys Thr Met Pro Ser Ile Thr Thr Pro His
 1               5                  10                  15

His His Pro Lys Asp Gln Asp Gln Cys Lys Asp Asp Gly Lys Ser Phe
             20                  25                  30

Val Phe Asp Ala Gln Val Leu Arg His Gln Thr Asn Ile Pro Gln Gln
         35                  40                  45

Phe Ile Trp Pro Asp Asn Glu Lys Pro Asn Ile Asn Ala Pro Glu Leu
     50                  55                  60

Gln Val Pro Leu Val Asp Leu Gly Asp Phe Leu Ser Gly Asn Pro Val
 65                  70                  75                  80

Ala Ala Val Glu Ala Ser Arg Leu Val Gly Glu Ala Cys Lys Lys His
                 85                  90                  95

Gly Phe Phe Leu Val Val Asn His Gly Val Asp Lys Thr Leu Ile Ala
                100                 105                 110

His Ala His Asn Tyr Val Asp Thr Phe Phe Lys Leu Pro Leu Ser Glu
            115                 120                 125

Lys Gln Lys Ala Gln Arg Lys Ile Gly Glu Ser Cys Gly Tyr Ala Ser
130                 135                 140

Ser Phe Thr Gly Arg Phe Ser Ser Lys Leu Pro Trp Lys Glu Thr Leu
145                 150                 155                 160

Ser Phe Arg Tyr Lys Ala Glu Glu Asn Ser Pro Lys His Ile Glu Glu
                165                 170                 175

Tyr Phe His Asn Arg Met Gly Glu Asp Phe Ala Glu Phe Gly Thr Val
            180                 185                 190

Tyr Gln Asp Tyr Cys Glu Ala Met Ser Thr Leu Ser Leu Gly Ile Met
        195                 200                 205

Glu Leu Leu Gly Met Ser Leu Gly Val Ser Arg Glu His Phe Arg Glu
210                 215                 220

Phe Phe Asn Glu Asn Asp Ser Ile Met Arg Leu Asn Tyr Tyr Pro Pro
225                 230                 235                 240

Cys Gln Lys Pro Asp Leu Pro Leu Gly Thr Gly Pro His Cys Asp Pro
                245                 250                 255

Thr Ser Leu Thr Ile Leu His Gln Asp Gln Val Gly Gly Leu Gln Val
            260                 265                 270

Phe Val Asp Asn Glu Trp Arg Ser Ile Asn Pro Asn Phe Asp Ala Phe
        275                 280                 285

Val Val Asn Ile Gly Asp Thr Phe Met Ala Leu Ser Asn Gly Ile Tyr
290                 295                 300

Lys Ser Cys Leu His Arg Ala Val Val Asn Ser Gln Thr Pro Arg Lys
305                 310                 315                 320

Ser Leu Ala Phe Phe Leu Cys Pro Lys Asn Asp Lys Met Val Thr Pro
                325                 330                 335

Pro His Glu Leu Val Asp Thr Cys Asp Pro Arg Ile Tyr Pro Asp Phe
            340                 345                 350

Thr Trp Pro Met Leu Leu Glu Phe Thr Gln Lys His Tyr Arg Ala Asp
        355                 360                 365

Met Lys Thr Leu Glu Val Phe Thr Asn Trp Leu His Gln Arg Ser Phe
370                 375                 380

Ser
385

<210> SEQ ID NO 46
<211> LENGTH: 385
```

<212> TYPE: PRT
<213> ORGANISM: Populus tremula

<400> SEQUENCE: 46

```
Met Ala Ile Asp Cys Ile Lys Thr Met Pro Ser Ile Thr Thr Pro His
1               5                   10                  15

His His Pro Lys Asp Gln Asp Gln Cys Lys Asp Gly Lys Ser Phe
            20                  25                  30

Val Phe Asp Ala Gln Val Leu Arg His Gln Thr Asn Ile Pro Gln Gln
                35                  40                  45

Phe Ile Trp Pro Asp Asn Glu Lys Pro Asn Ile Asn Ala Pro Glu Leu
        50                  55                  60

Gln Val Pro Leu Val Asp Leu Gly Asp Phe Leu Ser Gly Asn Pro Val
65                  70                  75                  80

Ala Ala Val Glu Ala Ser Arg Leu Val Gly Glu Ala Cys Lys Lys His
                85                  90                  95

Gly Phe Phe Leu Val Val Asn His Gly Val Asp Lys Thr Leu Ile Ala
                    100                 105                 110

His Ala His Asn Tyr Val Asp Thr Phe Phe Lys Leu Pro Leu Ser Glu
            115                 120                 125

Lys Gln Lys Ala Gln Arg Lys Ile Gly Glu Ser Cys Gly Tyr Ala Ser
        130                 135                 140

Ser Phe Thr Gly Arg Phe Ser Ser Lys Leu Pro Trp Lys Glu Thr Leu
145                 150                 155                 160

Ser Phe Arg Tyr Lys Ala Glu Glu Asn Ser Pro Lys His Ile Glu Glu
                165                 170                 175

Tyr Phe His Asn Arg Met Gly Glu Asp Phe Ala Glu Phe Gly Thr Val
            180                 185                 190

Tyr Gln Asp Tyr Cys Glu Ala Met Ser Thr Leu Ser Leu Gly Ile Met
        195                 200                 205

Glu Leu Leu Gly Met Ser Leu Gly Val Ser Arg Glu His Phe Arg Glu
210                 215                 220

Phe Phe Asn Glu Asn Asp Ser Ile Met Arg Leu Asn Tyr Tyr Pro Pro
225                 230                 235                 240

Cys Gln Lys Pro Asp Leu Thr Leu Gly Thr Gly Pro His Cys Asp Pro
                245                 250                 255

Thr Ser Leu Thr Ile Leu His Gln Asp Gln Val Gly Gly Leu Gln Val
            260                 265                 270

Phe Val Asp Asn Glu Trp Arg Ser Ile Asn Pro Asn Phe Asp Ala Phe
        275                 280                 285

Val Val Asn Ile Gly Asp Thr Phe Met Ala Leu Ser Asn Gly Ile Tyr
                295                 300
290

Lys Ser Cys Leu His Arg Ala Val Val Asn Ser Gln Thr Pro Arg Lys
305                 310                 315                 320

Ser Leu Ala Phe Phe Leu Cys Pro Lys Asn Asp Lys Met Val Thr Pro
                325                 330                 335

Pro His Glu Leu Val Asp Thr Cys Asn Pro Arg Ile Tyr Pro Asp Phe
            340                 345                 350

Thr Trp Pro Met Leu Leu Glu Phe Thr Gln Lys His Tyr Arg Ala Asp
        355                 360                 365

Met Lys Thr Leu Glu Val Phe Thr Asn Trp Leu His Gln Arg Ser Phe
370                 375                 380

Ser
385
```

<210> SEQ ID NO 47
<211> LENGTH: 385
<212> TYPE: PRT
<213> ORGANISM: Populus tremula

<400> SEQUENCE: 47

Met Ala Ile Asp Cys Ile Lys Thr Met Pro Ser Ile Thr Thr Pro His
1               5                   10                  15

His His Pro Lys Asp Gln Asp Gln Cys Lys Asp Asp Gly Lys Ser Phe
            20                  25                  30

Val Phe Asp Ala Gln Val Leu Arg His Gln Thr Asn Ile Pro Gln Gln
        35                  40                  45

Phe Ile Trp Pro Asp His Glu Lys Pro Asn Ile Asn Ala Pro Glu Leu
    50                  55                  60

Gln Val Pro Leu Val Asp Leu Gly Asp Phe Leu Ser Gly Asn Pro Val
65                  70                  75                  80

Ala Ala Val Glu Ala Ser Arg Leu Val Gly Glu Ala Cys Lys Lys His
                85                  90                  95

Gly Phe Phe Leu Val Val Asn His Gly Val Asp Lys Thr Leu Ile Ala
            100                 105                 110

His Ala His Asn Tyr Val Asp Thr Phe Phe Lys Leu Pro Leu Ser Glu
        115                 120                 125

Lys Gln Lys Ala Gln Arg Lys Ile Gly Glu Ser Cys Gly Tyr Ala Ser
    130                 135                 140

Ser Phe Thr Gly Arg Phe Ser Ser Lys Leu Pro Trp Lys Glu Thr Leu
145                 150                 155                 160

Ser Phe Arg Tyr Lys Ala Glu Glu Asn Ser Pro Lys His Ile Glu Glu
                165                 170                 175

Tyr Phe His Asn Arg Met Gly Glu Asp Phe Ala Glu Phe Gly Thr Val
            180                 185                 190

Tyr Gln Asp Tyr Cys Glu Ala Met Ser Thr Leu Ser Leu Gly Ile Met
        195                 200                 205

Glu Leu Leu Gly Met Ser Leu Gly Val Ser Arg Glu His Phe Arg Glu
    210                 215                 220

Phe Phe Asn Glu Asn Asp Ser Ile Met Arg Leu Asn Tyr Tyr Pro Pro
225                 230                 235                 240

Cys Gln Lys Pro Asp Leu Thr Leu Gly Thr Gly Pro His Cys Asp Pro
                245                 250                 255

Thr Ser Leu Thr Ile Leu His Gln Asp Gln Val Gly Gly Leu Gln Val
            260                 265                 270

Phe Val Asp Asn Glu Trp Arg Ser Ile Asn Pro Asn Phe Asp Ala Phe
        275                 280                 285

Val Val Asn Ile Gly Asp Thr Phe Met Ala Leu Ser Asn Gly Ile Tyr
    290                 295                 300

Lys Ser Cys Leu His Arg Ala Val Val Asn Ser Gln Thr Pro Arg Lys
305                 310                 315                 320

Ser Leu Ala Phe Phe Leu Cys Pro Lys Asn Asp Lys Met Val Thr Pro
                325                 330                 335

Pro His Glu Leu Val Asp Thr Cys Asn Pro Arg Ile Tyr Pro Asp Phe
            340                 345                 350

Thr Trp Pro Met Leu Leu Glu Phe Thr Gln Lys His Tyr Arg Ala Asp
        355                 360                 365

Met Lys Thr Leu Glu Val Phe Thr Asn Trp Leu His Gln Arg Ser Phe

-continued

```
              370                 375                 380
Ser
385

<210> SEQ ID NO 48
<211> LENGTH: 385
<212> TYPE: PRT
<213> ORGANISM: Populus tremula

<400> SEQUENCE: 48

Met Ala Ile Asp Cys Ile Lys Thr Met Pro Ser Ile Thr Thr Pro His
  1               5                  10                  15

His His Pro Lys Asp Gln Asp Gln Cys Lys Asp Asp Gly Lys Ser Phe
             20                  25                  30

Val Phe Asp Ala Gln Val Leu Arg His Gln Thr Asn Ile Pro Gln Gln
         35                  40                  45

Phe Ile Trp Pro Asp His Glu Lys Pro Asn Ile Asn Ala Pro Glu Leu
     50                  55                  60

Gln Val Pro Leu Val Asp Leu Gly Asp Phe Leu Ser Gly Asn Pro Val
 65                  70                  75                  80

Ala Ala Val Glu Ala Ser Arg Leu Val Gly Glu Ala Cys Lys Lys His
                 85                  90                  95

Gly Phe Phe Leu Val Val Asn His Gly Val Asp Lys Thr Leu Ile Ala
            100                 105                 110

His Ala His Asn Tyr Val Asp Thr Phe Phe Lys Leu Pro Leu Ser Glu
        115                 120                 125

Lys Gln Lys Ala Gln Arg Lys Ile Gly Glu Pro Cys Gly Tyr Ala Ser
    130                 135                 140

Ser Phe Thr Gly Arg Phe Ser Ser Lys Leu Pro Trp Lys Glu Thr Leu
145                 150                 155                 160

Ser Phe Arg Tyr Lys Ala Glu Glu Asn Ser Pro Lys His Ile Glu Glu
                165                 170                 175

Tyr Phe His Asn Arg Met Gly Glu Asp Phe Ala Glu Phe Gly Thr Val
            180                 185                 190

Tyr Gln Asp Tyr Cys Glu Ala Met Ser Thr Leu Ser Leu Gly Ile Met
        195                 200                 205

Glu Leu Leu Gly Met Ser Leu Gly Val Ser Arg Glu His Phe Arg Glu
    210                 215                 220

Phe Phe Asn Glu Asn Asp Ser Ile Met Arg Leu Asn Tyr Tyr Pro Pro
225                 230                 235                 240

Cys Gln Lys Pro Asp Leu Thr Leu Gly Thr Gly Pro His Cys Asp Pro
                245                 250                 255

Thr Ser Leu Thr Ile Leu His Gln Asp Gln Val Gly Gly Leu Gln Val
            260                 265                 270

Phe Val Asp Asn Glu Trp Arg Ser Ile Asn Pro Asn Phe Asp Ala Phe
        275                 280                 285

Val Val Asn Ile Gly Asp Thr Phe Met Ala Leu Ser Asn Gly Ile Tyr
    290                 295                 300

Lys Ser Cys Leu His Arg Ala Val Val Asn Ser Gln Thr Pro Arg Lys
305                 310                 315                 320

Ser Leu Ala Phe Phe Leu Cys Pro Lys Asn Asp Lys Met Val Thr Pro
                325                 330                 335

Pro His Glu Leu Val Asp Thr Cys Asn Pro Arg Ile Tyr Pro Asp Phe
            340                 345                 350
```

```
Thr Trp Pro Met Leu Leu Glu Phe Thr Gln Lys His Tyr Arg Ala Asp
            355                 360                 365

Met Lys Thr Leu Glu Val Phe Thr Asn Trp Leu His Gln Arg Ser Phe
        370                 375                 380

Ser
385

<210> SEQ ID NO 49
<211> LENGTH: 385
<212> TYPE: PRT
<213> ORGANISM: Populus tremula

<400> SEQUENCE: 49

Met Ala Ile Asp Cys Ile Lys Thr Met Pro Ser Ile Thr Thr Pro His
1               5                   10                  15

His His Pro Lys Asp Gln Asp Gln Cys Lys Asp Asp Gly Lys Ser Phe
            20                  25                  30

Val Phe Asp Ala Gln Val Leu Arg His Gln Thr Asn Ile Pro Gln Gln
        35                  40                  45

Phe Ile Trp Pro Asp Asn Glu Lys Pro Asn Ile Asn Ala Pro Glu Leu
    50                  55                  60

Gln Val Pro Leu Val Asp Leu Gly Asp Phe Leu Ser Gly Asn Pro Val
65                  70                  75                  80

Ala Ala Val Glu Ala Ser Arg Leu Val Gly Glu Ala Cys Lys Lys His
                85                  90                  95

Gly Phe Phe Leu Val Val Asn His Gly Val Asp Lys Thr Leu Ile Ala
            100                 105                 110

His Ala His Asn Tyr Val Asp Thr Phe Phe Lys Leu Pro Leu Ser Glu
        115                 120                 125

Lys Gln Lys Ala Gln Arg Lys Ile Gly Glu Ser Cys Gly Tyr Ala Ser
    130                 135                 140

Ser Phe Thr Gly Arg Phe Ser Ser Lys Leu Pro Trp Lys Glu Thr Leu
145                 150                 155                 160

Ser Phe Arg Tyr Lys Ala Glu Glu Asn Ser Ser Lys His Ile Glu Glu
                165                 170                 175

Tyr Phe His Asn Arg Met Gly Glu Asp Phe Ala Glu Phe Gly Thr Val
            180                 185                 190

Tyr Gln Asp Tyr Cys Glu Ala Met Ser Thr Leu Ser Leu Gly Ile Met
        195                 200                 205

Glu Leu Leu Gly Met Ser Leu Gly Val Ser Arg Glu His Phe Arg Glu
    210                 215                 220

Phe Phe Asn Glu Asn Asp Ser Ile Met Arg Leu Asn Tyr Tyr Pro Pro
225                 230                 235                 240

Cys Gln Lys Pro Asp Leu Thr Leu Gly Thr Gly Pro His Cys Asp Pro
                245                 250                 255

Thr Ser Leu Thr Ile Leu His Gln Asp Gln Val Gly Gly Leu Gln Val
            260                 265                 270

Phe Val Asp Asn Glu Trp Arg Ser Ile Asn Pro Asn Phe Asp Ala Phe
        275                 280                 285

Val Val Asn Ile Gly Asp Thr Phe Met Ala Leu Ser Asn Gly Ile Tyr
    290                 295                 300

Lys Ser Cys Leu His Arg Ala Val Val Asn Ser Gln Thr Pro Arg Lys
305                 310                 315                 320

Ser Leu Ala Phe Phe Leu Cys Pro Lys Asn Asp Lys Met Val Thr Pro
                325                 330                 335
```

```
Pro His Glu Leu Val Asp Thr Cys Asn Pro Arg Ile Tyr Pro Asp Phe
            340                 345                 350

Thr Trp Pro Met Leu Leu Glu Phe Thr Gln Lys His Tyr Arg Ala Asp
        355                 360                 365

Met Lys Thr Leu Glu Val Phe Thr Asn Trp Leu His Gln Arg Ser Phe
    370                 375                 380

Ser
385

<210> SEQ ID NO 50
<211> LENGTH: 385
<212> TYPE: PRT
<213> ORGANISM: Populus tremula

<400> SEQUENCE: 50

Met Ala Ile Asp Cys Ile Lys Thr Met Pro Ser Ile Thr Thr Pro His
 1               5                  10                  15

His His Pro Lys Asp Gln Asp Gln Cys Lys Asp Asp Gly Lys Ser Phe
            20                  25                  30

Val Phe Asp Ala Gln Val Leu Arg His Gln Thr Asn Ile Pro Gln Gln
        35                  40                  45

Phe Ile Trp Pro Asp His Glu Lys Pro Asn Ile Asn Ala Pro Glu Leu
    50                  55                  60

Gln Val Pro Leu Val Asp Leu Gly Asp Phe Leu Ser Gly Asn Pro Val
65                  70                  75                  80

Ala Ala Val Glu Ala Ser Arg Leu Val Gly Glu Ala Cys Lys Lys His
                85                  90                  95

Gly Phe Phe Leu Val Val Asn His Gly Val Asp Lys Thr Leu Ile Ala
            100                 105                 110

His Ala His Asn Tyr Val Asp Thr Phe Phe Lys Leu Pro Leu Ser Glu
        115                 120                 125

Lys Gln Lys Ala Gln Arg Lys Ile Gly Glu Ser Cys Gly Tyr Ala Ser
    130                 135                 140

Ser Phe Thr Gly Arg Phe Ser Ser Lys Leu Pro Trp Lys Glu Thr Leu
145                 150                 155                 160

Ser Phe Arg Tyr Gln Ala Glu Glu Asn Ser Pro Lys His Ile Glu Glu
                165                 170                 175

Tyr Phe His Asn Arg Met Gly Glu Asp Phe Ala Glu Phe Gly Thr Val
            180                 185                 190

Tyr Gln Asp Tyr Cys Glu Ala Met Ser Thr Leu Ser Leu Gly Ile Met
        195                 200                 205

Glu Leu Leu Gly Met Ser Leu Gly Val Ser Arg Glu His Phe Arg Glu
    210                 215                 220

Phe Phe Asn Glu Asn Asp Ser Ile Met Arg Leu Asn Tyr Tyr Pro Pro
225                 230                 235                 240

Cys Gln Lys Pro Asp Leu Thr Leu Gly Thr Gly Pro His Cys Asp Pro
                245                 250                 255

Thr Ser Leu Thr Ile Leu His Gln Asp Gln Val Gly Gly Leu Gln Val
            260                 265                 270

Phe Val Asp Asn Glu Trp Arg Ser Ile Asn Pro Asn Phe Asp Ala Phe
        275                 280                 285

Val Val Asn Ile Gly Asp Thr Phe Met Ala Leu Ser Asn Gly Ile Tyr
    290                 295                 300

Lys Ser Cys Leu His Arg Ala Val Val Asn Ser Gln Thr Pro Arg Lys
```

```
305                 310                 315                 320
Ser Leu Ala Phe Phe Leu Cys Pro Lys Asn Asp Lys Met Val Thr Pro
                325                 330                 335

Pro His Glu Leu Val Asp Thr Cys Asn Pro Arg Ile Tyr Pro Asp Phe
                340                 345                 350

Thr Trp Pro Met Leu Leu Glu Phe Thr Gln Lys His Tyr Arg Ala Asp
                355                 360                 365

Met Lys Thr Leu Glu Val Phe Thr Asn Trp Leu His Gln Arg Ser Leu
                370                 375                 380

Ser
385

<210> SEQ ID NO 51
<211> LENGTH: 385
<212> TYPE: PRT
<213> ORGANISM: Populus tremula

<400> SEQUENCE: 51

Met Ala Ile Asp Cys Ile Lys Thr Met Pro Ser Ile Thr Thr Pro His
1               5                   10                  15

His His Pro Lys Asp Gln Asp Gln Cys Lys Asp Asp Gly Lys Ser Phe
                20                  25                  30

Val Phe Asp Ala Gln Val Leu Arg His Gln Thr Asn Ile Pro Gln Gln
                35                  40                  45

Phe Ile Trp Pro Asp Asn Glu Lys Pro Asn Ile Asn Ala Pro Glu Leu
            50                  55                  60

Gln Val Pro Leu Val Asp Leu Gly Asp Phe Leu Ser Gly Asn Pro Val
65              70                  75                  80

Ala Ala Val Glu Ala Ser Arg Leu Val Gly Glu Ala Cys Lys Lys His
                85                  90                  95

Gly Phe Phe Leu Val Val Asn His Gly Val Asp Lys Thr Leu Ile Ala
                100                 105                 110

His Ala His Asn Tyr Val Asp Thr Phe Phe Lys Leu Pro Leu Ser Glu
                115                 120                 125

Lys Gln Lys Ala Gln Arg Lys Ile Gly Glu Ser Cys Gly Tyr Ala Ser
                130                 135                 140

Ser Phe Thr Gly Arg Phe Ser Ser Lys Leu Pro Trp Lys Glu Thr Leu
145                 150                 155                 160

Ser Phe Arg Tyr Gln Ala Glu Glu Asn Ser Pro Lys His Ile Glu Glu
                165                 170                 175

Tyr Phe His Asn Arg Met Gly Glu Asp Phe Ala Glu Phe Gly Thr Val
                180                 185                 190

Tyr Gln Asp Tyr Cys Glu Ala Met Ser Thr Leu Ser Leu Gly Ile Met
                195                 200                 205

Glu Leu Leu Gly Met Ser Leu Gly Val Ser Arg Glu His Phe Arg Glu
                210                 215                 220

Phe Phe Asn Glu Asn Asp Ser Ile Met Arg Leu Asn Tyr Tyr Pro Pro
225                 230                 235                 240

Cys Gln Lys Pro Asp Leu Thr Leu Gly Thr Gly Pro His Cys Asp Pro
                245                 250                 255

Thr Ser Leu Thr Ile Leu His Gln Asp Gln Val Gly Gly Leu Gln Val
                260                 265                 270

Phe Val Asp Asn Glu Trp Arg Ser Ile Asn Pro Asn Phe Asp Ala Phe
                275                 280                 285
```

```
Val Val Asn Ile Gly Asp Thr Phe Met Ala Leu Ser Asn Gly Ile Tyr
    290                 295                 300

Lys Ser Cys Leu His Arg Ala Val Val Asn Ser Gln Thr Pro Arg Lys
305                 310                 315                 320

Ser Leu Ala Phe Phe Leu Cys Pro Lys Asn Asp Lys Met Val Thr Pro
                325                 330                 335

Pro His Glu Leu Val Asp Thr Cys Asn Pro Arg Ile Tyr Pro Asp Phe
                340                 345                 350

Thr Trp Pro Met Leu Leu Glu Phe Thr Gln Lys His Tyr Arg Ala Asp
            355                 360                 365

Met Lys Thr Leu Glu Val Phe Thr Asn Trp Leu His Gln Arg Ser Phe
    370                 375                 380

Ser
385

<210> SEQ ID NO 52
<211> LENGTH: 385
<212> TYPE: PRT
<213> ORGANISM: Populus tremula

<400> SEQUENCE: 52

Met Ala Ile Asp Cys Ile Lys Thr Met Pro Ser Ile Thr Thr Pro His
1               5                   10                  15

His His Pro Lys Asp Gln Asp Gln Cys Lys Asp Asp Gly Lys Ser Phe
                20                  25                  30

Val Phe Asp Ala Gln Val Leu Arg His Gln Thr Asn Ile Pro Gln Gln
            35                  40                  45

Phe Ile Trp Pro Asp Asn Glu Lys Pro Asn Ile Asn Ala Pro Glu Leu
    50                  55                  60

Gln Val Pro Leu Val Asp Leu Gly Asp Phe Leu Ser Gly Asn Pro Val
65                  70                  75                  80

Ala Ala Val Glu Ala Ser Arg Leu Val Gly Glu Ala Cys Lys Lys His
                85                  90                  95

Gly Phe Phe Leu Val Val Asn His Gly Val Asp Lys Thr Leu Ile Ala
                100                 105                 110

His Ala His Asn Tyr Val Asp Thr Phe Phe Lys Leu Pro Leu Ser Glu
            115                 120                 125

Lys Gln Lys Ala Gln Arg Lys Ile Gly Glu Ser Cys Gly Tyr Ala Ser
    130                 135                 140

Ser Phe Thr Gly Arg Phe Ser Ser Lys Leu Pro Trp Lys Glu Thr Leu
145                 150                 155                 160

Ser Phe Arg Tyr Lys Ala Glu Glu Asn Ser Pro Lys His Ile Glu Glu
                165                 170                 175

Tyr Phe His Asn Arg Met Gly Glu Asp Phe Ala Glu Phe Gly Thr Val
                180                 185                 190

Tyr Gln Asp Tyr Cys Glu Ala Met Ser Thr Leu Ser Leu Gly Ile Met
            195                 200                 205

Glu Leu Leu Gly Met Ser Leu Gly Val Ser Arg Glu His Phe Arg Glu
    210                 215                 220

Phe Phe Asn Glu Asn Asp Ser Ile Met Arg Leu Asn Tyr Tyr Pro Pro
225                 230                 235                 240

Cys Gln Lys Pro Asp Leu Thr Leu Gly Thr Gly Pro His Cys Asp Pro
                245                 250                 255

Thr Ser Leu Thr Ile Leu His Gln Asp Gln Val Gly Gly Leu Gln Val
            260                 265                 270
```

Phe Val Asp Asn Glu Trp Arg Ser Ile Asn Pro Asn Phe Asp Ala Phe
            275                 280                 285

Val Val Asn Ile Gly Asp Thr Phe Met Ala Leu Ser Asn Gly Ile Tyr
            290                 295                 300

Lys Ser Cys Leu His Arg Ala Val Val Asn Ser Gln Thr Pro Arg Lys
305                 310                 315                 320

Ser Leu Ala Phe Phe Leu Cys Pro Lys Asn Asp Lys Met Val Thr Pro
            325                 330                 335

Pro His Glu Leu Val Asp Thr Cys Asn Pro Arg Ile Tyr Pro Asp Phe
            340                 345                 350

Thr Trp Pro Met Leu Leu Glu Phe Thr Gln Lys His Tyr Arg Ala Asp
            355                 360                 365

Met Lys Thr Leu Glu Val Phe Thr Asn Trp Leu His Gln Arg Ser Leu
            370                 375                 380

Ser
385

<210> SEQ ID NO 53
<211> LENGTH: 385
<212> TYPE: PRT
<213> ORGANISM: Populus tremula

<400> SEQUENCE: 53

Met Ala Ile Asp Cys Ile Lys Thr Met Pro Ser Ile Thr Thr Pro His
1               5                   10                  15

His His Pro Lys Asp Gln Asp Gln Cys Lys Asp Asp Gly Lys Ser Phe
                20                  25                  30

Val Phe Asp Ala Gln Val Leu Arg His Gln Thr Asn Ile Pro Gln Gln
            35                  40                  45

Phe Ile Trp Pro Asp Asn Glu Lys Pro Asn Ile Asn Ala Pro Glu Leu
        50                  55                  60

Gln Val Pro Leu Val Asp Leu Gly Asp Phe Leu Ser Gly Asn Pro Val
65                  70                  75                  80

Ala Ala Val Glu Ala Ser Arg Leu Val Gly Glu Ala Cys Lys Lys His
                85                  90                  95

Gly Phe Phe Leu Val Val Asn His Gly Val Asp Lys Thr Leu Ile Ala
            100                 105                 110

His Ala His Asn Tyr Val Asp Thr Phe Phe Lys Leu Pro Leu Ser Glu
        115                 120                 125

Lys Gln Lys Ala Gln Arg Lys Ile Gly Glu Ser Cys Gly Tyr Ala Ser
130                 135                 140

Ser Phe Thr Gly Arg Phe Ser Ser Lys Leu Pro Trp Lys Glu Thr Leu
145                 150                 155                 160

Ser Phe Arg Tyr Lys Ala Glu Glu Asn Ser Pro Lys His Ile Glu Glu
                165                 170                 175

Tyr Phe His Asn Arg Met Gly Glu Asp Phe Ala Glu Phe Gly Thr Val
            180                 185                 190

Tyr Gln Asp Tyr Cys Glu Ala Met Ser Thr Leu Ser Leu Gly Ile Met
        195                 200                 205

Glu Leu Leu Gly Met Ser Leu Gly Val Ser Arg Glu His Phe Arg Glu
210                 215                 220

Phe Phe Asn Glu Asp Asp Ser Ile Met Arg Leu Asn Tyr Tyr Pro Pro
225                 230                 235                 240

Cys Gln Lys Pro Asp Leu Thr Leu Gly Thr Gly Pro His Cys Asp Pro

-continued

```
             245                 250                 255
Thr Ser Leu Thr Ile Leu His Gln Asp Gln Val Gly Gly Leu Gln Val
            260                 265                 270

Phe Val Asp Asn Glu Trp Arg Ser Ile Asn Pro Asn Phe Asp Ala Phe
            275                 280                 285

Val Val Asn Ile Gly Asp Thr Phe Met Ala Leu Ser Asn Gly Ile Tyr
            290                 295                 300

Lys Ser Cys Leu His Arg Ala Val Val Asn Ser Gln Thr Pro Arg Lys
305                 310                 315                 320

Ser Leu Ala Phe Phe Leu Cys Pro Lys Asn Asp Lys Met Val Thr Pro
            325                 330                 335

Pro His Glu Leu Val Asp Thr Cys Asn Pro Arg Ile Tyr Pro Asp Phe
            340                 345                 350

Thr Trp Pro Met Leu Leu Glu Phe Thr Gln Lys His Tyr Arg Ala Asp
            355                 360                 365

Met Lys Thr Leu Glu Val Phe Thr Asn Trp Leu His Gln Arg Ser Leu
            370                 375                 380

Ser
385

<210> SEQ ID NO 54
<211> LENGTH: 385
<212> TYPE: PRT
<213> ORGANISM: Populus alba

<400> SEQUENCE: 54

Met Ala Ile Asp Cys Ile Lys Thr Met Pro Ser Ile Thr Thr Pro His
  1               5                  10                  15

His His Pro Lys Asp Gln Asp Gln Cys Lys Asp Asp Gly Lys Ser Phe
                 20                  25                  30

Val Phe Asp Ala Gln Val Leu Arg His Gln Thr Asn Ile Pro Gln Gln
             35                  40                  45

Phe Ile Trp Pro Asp His Glu Lys Pro Asn Thr Asn Ala Pro Glu Leu
         50                  55                  60

Gln Val Pro Leu Val Asp Leu Gly Asp Phe Leu Ser Gly Asn Pro Val
 65                  70                  75                  80

Ala Ala Val Glu Ala Ser Arg Leu Val Gly Glu Ala Cys Lys Lys His
                 85                  90                  95

Gly Phe Phe Leu Val Val Asn His Gly Val Asp Lys Thr Leu Ile Ala
                100                 105                 110

His Ala His Asn Tyr Val Asp Thr Phe Phe Lys Leu Pro Leu Ser Glu
            115                 120                 125

Lys Gln Lys Ala Gln Arg Lys Ile Gly Glu Ser Cys Gly Tyr Ala Ser
130                 135                 140

Ser Phe Thr Gly Arg Phe Ser Ser Lys Leu Pro Trp Lys Glu Thr Leu
145                 150                 155                 160

Ser Phe Arg Tyr Lys Ala Glu Glu Ser Ser Lys His Ile Glu Glu
                165                 170                 175

Tyr Phe His Asn Arg Met Gly Glu Asp Phe Ala Glu Phe Gly Thr Val
            180                 185                 190

Tyr Gln Asp Tyr Cys Glu Ala Met Ser Thr Leu Ser Leu Gly Ile Met
            195                 200                 205

Glu Leu Leu Gly Met Ser Leu Gly Val Ser Arg Glu His Phe Arg Glu
210                 215                 220
```

```
Phe Phe Asn Glu Asn Asp Ser Ile Met Arg Leu Asn Tyr Tyr Pro Pro
225                 230                 235                 240

Cys Gln Lys Pro Asp Leu Thr Leu Gly Thr Gly Pro His Cys Asp Pro
            245                 250                 255

Thr Ser Leu Thr Ile Leu His Gln Asp Gln Val Gly Gly Leu Gln Val
                260                 265                 270

Phe Val Asp Asn Glu Trp Arg Ser Ile Asn Pro Asn Phe Asp Ala Phe
        275                 280                 285

Val Val Asn Ile Gly Asp Thr Phe Met Ala Leu Ser Asn Gly Ile Tyr
    290                 295                 300

Arg Ser Cys Leu His Arg Ala Val Val Asn Ser Gln Thr Pro Arg Lys
305                 310                 315                 320

Ser Leu Ala Phe Phe Leu Cys Pro Lys Asn Asp Lys Met Val Thr Pro
                325                 330                 335

Pro His Glu Leu Val Asp Thr Cys Asn Pro Arg Ile Tyr Pro Asp Phe
            340                 345                 350

Thr Trp Pro Met Leu Leu Glu Phe Thr Gln Lys His Tyr Arg Ala Asp
        355                 360                 365

Met Lys Thr Leu Glu Val Phe Thr Asn Trp Leu His Gln Arg Ser Leu
    370                 375                 380

Ser
385

<210> SEQ ID NO 55
<211> LENGTH: 385
<212> TYPE: PRT
<213> ORGANISM: Populus alba

<400> SEQUENCE: 55

Met Ala Ile Asp Cys Ile Lys Thr Met Pro Ser Ile Thr Thr Pro His
1               5                   10                  15

His His Pro Lys Asp Gln Asp Gln Cys Lys Asp Asp Gly Lys Ser Phe
            20                  25                  30

Val Phe Asp Ala Gln Val Leu Arg His Gln Thr Asn Ile Pro Gln Gln
        35                  40                  45

Phe Ile Trp Pro Asp His Glu Lys Pro Asn Ile Asn Ala Pro Glu Leu
    50                  55                  60

Gln Val Pro Leu Val Asp Leu Gly Asp Phe Leu Ser Gly Asn Pro Val
65                  70                  75                  80

Ala Ala Val Glu Ala Ser Arg Leu Val Gly Glu Ala Cys Lys Lys His
                85                  90                  95

Gly Phe Phe Leu Val Val Asn His Gly Val Asp Lys Thr Leu Ile Ala
            100                 105                 110

His Ala His Asn Tyr Val Asp Thr Phe Phe Lys Leu Pro Leu Ser Glu
        115                 120                 125

Lys Gln Lys Ala Gln Arg Lys Ile Gly Glu Ser Cys Gly Tyr Ala Ser
    130                 135                 140

Ser Phe Thr Gly Arg Phe Ser Ser Lys Leu Pro Trp Lys Glu Thr Leu
145                 150                 155                 160

Ser Phe Arg Tyr Lys Ala Glu Glu Asn Ser Ser Lys His Ile Glu Glu
                165                 170                 175

Tyr Phe His Asn Arg Met Gly Glu Asp Phe Ala Glu Phe Gly Thr Val
            180                 185                 190

Tyr Gln Asp Tyr Cys Glu Ala Met Ser Thr Leu Ser Leu Gly Ile Met
        195                 200                 205
```

```
Glu Leu Leu Gly Met Ser Leu Gly Val Ser Arg Glu His Phe Arg Glu
    210                 215                 220

Phe Phe Asn Glu Asn Asp Ser Ile Met Arg Leu Asn Tyr Tyr Pro Pro
225                 230                 235                 240

Cys Gln Lys Pro Asp Leu Thr Leu Gly Thr Gly Pro His Cys Asp Pro
                245                 250                 255

Thr Ser Leu Thr Ile Leu His Gln Asp Gln Val Gly Gly Leu Gln Val
                260                 265                 270

Phe Val Asp Asn Glu Trp Arg Ser Ile Asn Pro Asn Phe Asp Ala Phe
                275                 280                 285

Val Val Asn Ile Gly Asp Thr Phe Met Ala Leu Ser Asn Gly Ile Tyr
            290                 295                 300

Lys Ser Cys Leu His Arg Ala Val Val Asn Ser Gln Thr Pro Arg Lys
305                 310                 315                 320

Ser Leu Ala Phe Phe Leu Cys Pro Lys Asn Asp Lys Met Val Thr Pro
                325                 330                 335

Pro His Glu Leu Val Asp Thr Cys Asn Pro Arg Ile Tyr Pro Asp Phe
                340                 345                 350

Thr Trp Pro Met Leu Leu Glu Phe Thr Gln Lys His Tyr Arg Ala Asp
                355                 360                 365

Met Lys Thr Leu Glu Val Phe Thr Asn Trp Leu His Gln Arg Ser Leu
    370                 375                 380

Ser
385

<210> SEQ ID NO 56
<211> LENGTH: 369
<212> TYPE: PRT
<213> ORGANISM: Lactuca sativa

<400> SEQUENCE: 56

Met Pro Ser Leu His Lys Glu His Ile Asn Ala Gln Pro Lys Pro Leu
1               5                   10                  15

Val Phe Asp Ser Leu Ile Leu Gln His Glu Thr Asn Ile Pro Glu Gln
                20                  25                  30

Phe Ile Trp Pro Asp His Glu Lys Pro Asn Ser Gln Lys Ala Lys Glu
            35                  40                  45

Leu Ala Val Pro Leu Val Asp Leu Arg Gly Phe Leu Ser Gly Arg Ala
    50                  55                  60

Ser Ser Ala Lys Glu Ala Ser Val Val Gly Glu Ala Cys Lys Lys
65                  70                  75                  80

His Gly Phe Phe Leu Val Thr Asn His Gly Val Asp Ala Ser Leu Ile
                85                  90                  95

Val Asp Ala His Arg Tyr Met Asp Leu Phe Phe Glu Leu Pro Phe Leu
                100                 105                 110

Asp Lys Gln Arg Val Gln Arg Lys Ile Gly Glu Ser Cys Gly Tyr Ala
            115                 120                 125

Ser Ser Phe Thr Gly Arg Phe Ser Ser Lys Leu Pro Trp Lys Glu Thr
    130                 135                 140

Leu Ser Phe Gln Phe Ser Gly Glu Lys Lys Ser Ser Lys Ile Val Glu
145                 150                 155                 160

Glu Tyr Phe Glu Lys Thr Met Gly Lys Glu Phe Ala Arg Leu Gly Lys
                165                 170                 175

Val Tyr Gln Glu Tyr Cys Asn Ala Met Ser Arg Leu Ser Leu Gly Ile
```

-continued

```
                180                 185                 190
Met Glu Leu Leu Gly Met Ser Leu Gly Val Glu Gln Ser His Phe Lys
        195                 200                 205

Glu Phe Phe Lys Glu Asn Asp Ser Ile Met Arg Leu Asn Tyr Tyr Pro
    210                 215                 220

Pro Cys Gln Lys Pro Asp Leu Thr Leu Gly Thr Gly Pro His Cys Asp
225                 230                 235                 240

Pro Thr Ser Leu Thr Ile Leu His Gln Asp Thr Val Gly Gly Leu Glu
                245                 250                 255

Val Phe Ile Asp Asn Glu Trp Arg Ser Ile Ala Pro Asn Leu Asn Thr
            260                 265                 270

Phe Val Val Asn Ile Gly Asp Thr Phe Met Ala Leu Ser Asn Gly Gln
        275                 280                 285

Tyr Arg Ser Cys Leu His Arg Ala Val Val Asn Asn Lys Ile His Arg
    290                 295                 300

Lys Ser Leu Ala Phe Phe Leu Cys Pro Lys Lys Asp Lys Val Val Ser
305                 310                 315                 320

Pro Pro Asp Glu Leu Val Asp Glu Lys Asn Pro Arg Ile Tyr Pro Asp
                325                 330                 335

Phe Thr Trp Ser Thr Phe Leu Glu Phe Thr Gln Lys His Tyr Arg Ala
            340                 345                 350

Asp Met Asn Thr Leu Gln Ala Phe Thr Asn Trp Ile Gln Gln Lys Asn
        355                 360                 365

Ser
```

<210> SEQ ID NO 57
<211> LENGTH: 365
<212> TYPE: PRT
<213> ORGANISM: Triticum aestivum

<400> SEQUENCE: 57

```
Met Val Arg Pro Val Phe Asp Ala Ala Val Leu Ser Gly Arg Ser Asp
  1               5                  10                  15

Ile Pro Ser Gln Phe Ile Trp Pro Glu Gly Glu Ser Pro Thr Pro Asp
            20                  25                  30

Ala Ala Glu Glu Leu His Val Pro Leu Ile Asn Ile Gly Gly Met Leu
        35                  40                  45

Ser Gly Asp Ala Ala Ala Ala Glu Val Thr Arg Leu Val Gly Glu
    50                  55                  60

Ala Cys Glu Arg His Gly Phe Phe Gln Val Val Asn His Gly Ile Asp
65                  70                  75                  80

Ala Glu Leu Leu Ala Asp Ala His Arg Cys Val Asp Asn Phe Phe Thr
                85                  90                  95

Met Pro Leu Pro Glu Lys Gln Arg Ala Leu Arg Arg Pro Gly Glu Ser
            100                 105                 110

Cys Gly Tyr Ala Ser Ser Phe Thr Gly Arg Phe Ala Ser Lys Leu Pro
        115                 120                 125

Trp Lys Glu Thr Leu Ser Phe Arg Ser Cys Pro Ser Asp Pro Ala Leu
    130                 135                 140

Val Val Asp Tyr Ile Val Ala Thr Leu Gly Glu Asp His Arg Arg Leu
145                 150                 155                 160

Gly Glu Val Tyr Ala Arg Tyr Cys Ser Glu Met Ser Arg Leu Ser Leu
                165                 170                 175

Glu Ile Met Glu Val Leu Gly Glu Ser Leu Gly Val Gly Arg Ala His
```

-continued

```
                180                 185                 190
Tyr Arg Arg Phe Phe Glu Gly Asn Asp Ser Ile Met Arg Leu Asn Tyr
            195                 200                 205

Tyr Pro Pro Cys Gln Arg Pro Leu Glu Thr Leu Gly Thr Gly Pro His
        210                 215                 220

Cys Asp Pro Thr Ser Leu Thr Ile Leu His Gln Asp Asn Val Gly Gly
225                 230                 235                 240

Leu Gln Val His Thr Glu Gly Arg Trp Arg Ser Ile Arg Pro Arg Ala
                245                 250                 255

Asp Ala Phe Val Val Asn Ile Gly Asp Thr Phe Met Ala Leu Ser Asn
            260                 265                 270

Gly Arg Tyr Lys Ser Cys Leu His Arg Ala Val Val Asn Ser Arg Val
                275                 280                 285

Pro Arg Lys Ser Leu Ala Phe Phe Leu Cys Pro Glu Met Asp Lys Val
        290                 295                 300

Val Ala Pro Pro Gly Thr Leu Val Asp Ala Ser Asn Pro Arg Ala Tyr
305                 310                 315                 320

Pro Asp Phe Thr Trp Arg Ser Leu Leu Asp Phe Thr Gln Lys His Tyr
                325                 330                 335

Arg Ala Asp Met Lys Thr Leu Glu Val Phe Ser Ser Trp Ile Val Gln
            340                 345                 350

Gln Gln Gln Gly Gln Leu Ala Leu Gln Pro Ala Met Thr
                355                 360                 365

<210> SEQ ID NO 58
<211> LENGTH: 365
<212> TYPE: PRT
<213> ORGANISM: Triticum aestivum

<400> SEQUENCE: 58

Met Val Gln Pro Val Phe Asp Ala Ala Val Leu Ser Gly Arg Ala Asp
 1               5                  10                  15

Ile Pro Ser Gln Phe Ile Trp Pro Glu Gly Glu Ser Pro Thr Pro Asp
                20                  25                  30

Ala Ala Glu Glu Leu His Val Pro Leu Ile Asp Ile Gly Gly Met Leu
            35                  40                  45

Ser Gly Asp Pro Arg Ala Thr Ala Glu Val Thr Arg Leu Val Gly Glu
        50                  55                  60

Ala Cys Glu Arg His Gly Phe Phe Gln Val Val Asn His Gly Ile Asp
65                  70                  75                  80

Ala Glu Leu Leu Ala Asp Ala His Arg Cys Val Asp Ala Phe Phe Thr
                85                  90                  95

Met Pro Leu Pro Glu Lys Gln Arg Ala Leu Arg Arg Pro Gly Glu Ser
            100                 105                 110

Cys Gly Tyr Ala Ser Ser Phe Thr Gly Arg Phe Ala Ser Lys Leu Pro
        115                 120                 125

Trp Lys Glu Thr Leu Ser Phe Arg Ser Cys Pro Ser Asp Pro Ala Leu
    130                 135                 140

Val Val Asp Tyr Ile Val Ala Thr Leu Gly Glu Asp His Arg Arg Leu
145                 150                 155                 160

Gly Glu Val Tyr Ala Arg Tyr Cys Ser Glu Met Ser Arg Leu Ser Leu
                165                 170                 175

Glu Ile Met Glu Val Leu Gly Glu Ser Leu Gly Val Gly Arg Ala His
            180                 185                 190
```

```
Tyr Arg Arg Phe Phe Glu Gly Asn Asp Ser Ile Met Arg Leu Asn Tyr
        195                 200                 205

Tyr Pro Pro Cys Gln Arg Pro Met Glu Thr Leu Gly Thr Gly Pro His
    210                 215                 220

Cys Asp Pro Thr Ser Leu Thr Ile Leu His Gln Asp Asn Val Gly Gly
225                 230                 235                 240

Leu Gln Val His Thr Glu Gly Arg Trp Arg Ser Ile Arg Pro Arg Ala
                245                 250                 255

Asp Ala Phe Val Val Asn Ile Gly Asp Thr Phe Met Ala Leu Ser Asn
            260                 265                 270

Gly Arg Tyr Lys Ser Cys Leu His Arg Ala Val Val Asn Ser Lys Val
        275                 280                 285

Pro Arg Lys Ser Leu Ala Phe Phe Leu Cys Pro Glu Met Asp Lys Val
    290                 295                 300

Val Ala Pro Pro Gly Thr Leu Val Asp Ala Ala Asn Pro Arg Ala Tyr
305                 310                 315                 320

Pro Asp Phe Thr Trp Arg Ser Leu Leu Asp Phe Thr Gln Lys His Tyr
                325                 330                 335

Arg Ala Asp Met Lys Thr Leu Glu Val Phe Ser Ser Trp Ile Val Gln
            340                 345                 350

Gln Gln Gln Gly Gln Leu Leu Pro Pro Leu Ala Ser His
        355                 360                 365

<210> SEQ ID NO 59
<211> LENGTH: 361
<212> TYPE: PRT
<213> ORGANISM: Triticum aestivum

<400> SEQUENCE: 59

Met Val Gln Pro Val Phe Asp Ala Ala Val Leu Ser Gly Arg Ala Asp
  1               5                  10                  15

Ile Pro Ser Gln Phe Ile Trp Pro Glu Gly Ser Pro Thr Pro Asp
            20                  25                  30

Ala Ala Glu Glu Leu His Val Pro Leu Ile Asp Ile Gly Gly Met Leu
        35                  40                  45

Ser Gly Asp Pro Ala Ala Ala Glu Val Thr Arg Leu Val Gly Glu
    50                  55                  60

Ala Cys Glu Arg His Gly Phe Phe Gln Val Val Asn His Gly Ile Asp
65                  70                  75                  80

Ala Glu Leu Leu Ala Asp Ala His Arg Cys Val Asp Asn Phe Phe Thr
                85                  90                  95

Met Pro Leu Pro Glu Lys Gln Arg Ala Leu Arg His Pro Gly Glu Ser
            100                 105                 110

Cys Gly Tyr Ala Ser Ser Phe Thr Gly Arg Phe Ala Ser Lys Leu Pro
        115                 120                 125

Trp Lys Glu Thr Leu Ser Phe Arg Ser Cys Pro Ser Asp Pro Ala Leu
    130                 135                 140

Val Val Asp Tyr Ile Val Ala Thr Leu Gly Glu Asp His Arg Arg Leu
145                 150                 155                 160

Gly Glu Val Tyr Ala Arg Tyr Cys Ser Glu Met Ser Arg Leu Ser Leu
                165                 170                 175

Glu Ile Met Glu Val Leu Gly Glu Ser Leu Gly Val Gly Arg Ala His
            180                 185                 190

Tyr Arg Arg Phe Phe Glu Gly Asn Asp Ser Ile Met Arg Leu Asn Tyr
        195                 200                 205
```

```
Tyr Pro Pro Cys Gln Arg Pro Leu Glu Thr Leu Gly Thr Gly Pro His
    210                 215                 220

Cys Asp Pro Thr Ser Leu Thr Ile Leu His Gln Asp Asn Val Gly Gly
225                 230                 235                 240

Leu Gln Val His Thr Glu Gly Arg Trp Arg Ser Ile Arg Pro Arg Ala
                245                 250                 255

Asp Ala Phe Val Val Asn Ile Gly Asp Thr Phe Met Ala Leu Ser Asn
            260                 265                 270

Gly Arg Tyr Lys Ser Cys Leu His Arg Ala Val Val Asn Ser Arg Val
        275                 280                 285

Pro Arg Lys Ser Leu Ala Phe Phe Leu Cys Pro Glu Met Asp Lys Val
    290                 295                 300

Val Ala Pro Pro Gly Thr Leu Val Asp Ala Ala Asn Pro Arg Ala Tyr
305                 310                 315                 320

Pro Asp Phe Thr Trp Arg Ser Leu Leu Asp Phe Thr Gln Lys His Tyr
                325                 330                 335

Arg Ala Asp Met Lys Thr Leu Glu Val Phe Ser Ser Trp Ile Val Gln
            340                 345                 350

Gln Gln Gln Pro Gln Pro Ala Arg Thr
        355                 360

<210> SEQ ID NO 60
<211> LENGTH: 372
<212> TYPE: PRT
<213> ORGANISM: Oryza sativa

<400> SEQUENCE: 60

Met Ser Met Val Val Gln Gln Glu Gln Glu Val Val Phe Asp Ala Ala
1               5                   10                  15

Val Leu Ser Gly Gln Thr Glu Ile Pro Ser Gln Phe Ile Trp Pro Ala
            20                  25                  30

Glu Glu Ser Pro Gly Ser Val Ala Val Glu Glu Leu Glu Val Ala Leu
        35                  40                  45

Ile Asp Val Gly Ala Gly Ala Glu Arg Ser Ser Val Val Arg Gln Val
    50                  55                  60

Gly Glu Ala Cys Glu Arg His Gly Phe Phe Leu Val Val Asn His Gly
65                  70                  75                  80

Ile Glu Ala Ala Leu Leu Glu Glu Ala His Arg Cys Met Asp Ala Phe
                85                  90                  95

Phe Thr Leu Pro Leu Gly Glu Lys Gln Arg Ala Gln Arg Arg Ala Gly
            100                 105                 110

Glu Ser Cys Gly Tyr Ala Ser Ser Phe Thr Gly Arg Phe Ala Ser Lys
        115                 120                 125

Leu Pro Trp Lys Glu Thr Leu Ser Phe Arg Tyr Ser Ser Ala Gly Asp
    130                 135                 140

Glu Glu Gly Glu Glu Gly Val Gly Glu Tyr Leu Val Arg Lys Leu Gly
145                 150                 155                 160

Ala Glu His Gly Arg Arg Leu Gly Glu Val Tyr Ser Arg Tyr Cys His
                165                 170                 175

Glu Met Ser Arg Leu Ser Leu Glu Leu Met Glu Val Leu Gly Glu Ser
            180                 185                 190

Leu Gly Ile Val Gly Asp Arg Arg His Tyr Phe Arg Arg Phe Phe Gln
        195                 200                 205

Arg Asn Asp Ser Ile Met Arg Leu Asn Tyr Tyr Pro Ala Cys Gln Arg
```

```
              210                 215                 220
Pro Leu Asp Thr Leu Gly Thr Gly Pro His Cys Asp Pro Thr Ser Leu
225                 230                 235                 240

Thr Ile Leu His Gln Asp His Val Gly Gly Leu Glu Val Trp Ala Glu
                245                 250                 255

Gly Arg Trp Arg Ala Ile Arg Pro Arg Pro Gly Ala Leu Val Val Asn
            260                 265                 270

Val Gly Asp Thr Phe Met Ala Leu Ser Asn Ala Arg Tyr Arg Ser Cys
        275                 280                 285

Leu His Arg Ala Val Val Asn Ser Thr Ala Pro Arg Arg Ser Leu Ala
290                 295                 300

Phe Phe Leu Cys Pro Glu Met Asp Thr Val Val Arg Pro Pro Glu Glu
305                 310                 315                 320

Leu Val Asp Asp His His Pro Arg Val Tyr Pro Asp Phe Thr Trp Arg
                325                 330                 335

Ala Leu Leu Asp Phe Thr Gln Arg His Tyr Arg Ala Asp Met Arg Leu
            340                 345                 350

Phe Gln Ala Phe Ser Asp Trp Leu Asn His His Arg His Leu Gln Pro
        355                 360                 365

Thr Ile Tyr Ser
    370

<210> SEQ ID NO 61
<211> LENGTH: 389
<212> TYPE: PRT
<213> ORGANISM: Oryza sativa

<400> SEQUENCE: 61

Met Val Ala Glu His Pro Thr Pro Gln Pro His Gln Pro Pro Pro
 1               5                  10                  15

Met Asp Ser Thr Ala Gly Ser Gly Ile Ala Ala Pro Ala Ala Ala
                20                  25                  30

Val Cys Asp Leu Arg Met Glu Pro Lys Ile Pro Glu Pro Phe Val Trp
            35                  40                  45

Pro Asn Gly Asp Ala Arg Pro Ala Ser Ala Ala Glu Leu Asp Met Pro
50                  55                  60

Val Val Asp Val Gly Val Leu Arg Asp Gly Asp Ala Glu Gly Leu Arg
65                  70                  75                  80

Arg Ala Ala Ala Gln Val Ala Ala Ala Cys Ala Thr His Gly Phe Phe
                85                  90                  95

Gln Val Ser Glu His Gly Val Asp Ala Ala Leu Ala Arg Ala Ala Leu
            100                 105                 110

Asp Gly Ala Ser Asp Phe Phe Arg Leu Pro Leu Ala Glu Lys Arg Arg
        115                 120                 125

Ala Arg Arg Val Pro Gly Thr Val Ser Gly Tyr Thr Ser Ala His Ala
130                 135                 140

Asp Arg Phe Ala Ser Lys Leu Pro Trp Lys Glu Thr Leu Ser Phe Gly
145                 150                 155                 160

Phe His Asp Arg Ala Ala Ala Pro Val Val Ala Asp Tyr Phe Ser Ser
                165                 170                 175

Thr Leu Gly Pro Asp Phe Ala Pro Met Gly Arg Val Tyr Gln Lys Tyr
            180                 185                 190

Cys Glu Glu Met Lys Glu Leu Ser Leu Thr Ile Met Glu Leu Leu Glu
        195                 200                 205
```

-continued

```
Leu Ser Leu Gly Val Glu Arg Gly Tyr Tyr Arg Glu Phe Phe Ala Asp
210                 215                 220

Ser Ser Ser Ile Met Arg Cys Asn Tyr Tyr Pro Cys Pro Glu Pro
225                 230                 235                 240

Glu Arg Thr Leu Gly Thr Gly Pro His Cys Asp Pro Thr Ala Leu Thr
                245                 250                 255

Ile Leu Leu Gln Asp Asp Val Gly Gly Leu Glu Val Leu Val Asp Gly
            260                 265                 270

Glu Trp Arg Pro Val Ser Pro Val Pro Gly Ala Met Val Ile Asn Ile
        275                 280                 285

Gly Asp Thr Phe Met Ala Leu Ser Asn Gly Arg Tyr Lys Ser Cys Leu
290                 295                 300

His Arg Ala Val Val Asn Gln Arg Arg Glu Arg Ser Leu Ala Phe
305                 310                 315                 320

Phe Leu Cys Pro Arg Glu Asp Arg Val Val Arg Pro Pro Ser Ala
                325                 330                 335

Ala Thr Pro Gln His Tyr Pro Asp Phe Thr Trp Ala Asp Leu Met Arg
            340                 345                 350

Phe Thr Gln Arg His Tyr Arg Ala Asp Thr Arg Thr Leu Asp Ala Phe
        355                 360                 365

Thr Arg Trp Leu Ala Pro Pro Ala Ala Asp Ala Ala Thr Ala Gln
370                 375                 380

Val Glu Ala Ala Ser
385

<210> SEQ ID NO 62
<211> LENGTH: 389
<212> TYPE: PRT
<213> ORGANISM: Oryza rufipogon

<400> SEQUENCE: 62

Met Val Ala Glu His Pro Thr Pro Pro Gln Pro His Gln Pro Pro Pro
1               5                   10                  15

Met Asp Ser Thr Ala Gly Ser Gly Ile Ala Ala Pro Ala Ala Ala
            20                  25                  30

Val Cys Asp Leu Arg Met Glu Pro Lys Ile Pro Glu Pro Phe Val Trp
        35                  40                  45

Pro Asn Gly Asp Ala Arg Pro Ala Ser Ala Ala Glu Leu Asp Met Pro
    50                  55                  60

Val Val Asp Val Gly Val Leu Arg Asp Gly Asp Ala Glu Gly Leu Arg
65                  70                  75                  80

Arg Ala Ala Ala Gln Val Ala Ala Ala Cys Ala Thr His Gly Phe Phe
                85                  90                  95

Gln Val Ser Gly His Gly Val Asp Ala Ala Leu Ala Arg Ala Ala Leu
            100                 105                 110

Asp Gly Ala Ser Asp Phe Phe Arg Leu Pro Leu Ala Glu Lys Arg Arg
        115                 120                 125

Ala Arg Arg Val Pro Gly Thr Val Ser Gly Tyr Thr Ser Ala His Ala
    130                 135                 140

Asp Arg Phe Ala Ser Lys Leu Pro Trp Lys Glu Thr Leu Ser Phe Gly
145                 150                 155                 160

Phe His Asp Arg Ala Ala Ala Pro Val Val Ala Asp Tyr Phe Ser Ser
                165                 170                 175

Thr Leu Gly Pro Asp Phe Ala Pro Met Gly Arg Val Tyr Gln Lys Tyr
            180                 185                 190
```

```
Cys Glu Glu Met Lys Glu Leu Ser Leu Thr Ile Met Glu Leu Leu Glu
            195                 200                 205

Leu Ser Leu Gly Val Glu Arg Gly Tyr Tyr Arg Glu Phe Phe Ala Asp
        210                 215                 220

Ser Ser Ser Ile Met Arg Cys Asn Tyr Tyr Pro Pro Cys Pro Glu Pro
225                 230                 235                 240

Glu Arg Thr Leu Gly Thr Gly Pro His Cys Asp Pro Thr Ala Leu Thr
                245                 250                 255

Ile Leu Leu Gln Asp Asp Val Gly Gly Leu Glu Val Leu Val Asp Gly
            260                 265                 270

Glu Trp Arg Pro Val Ser Pro Val Pro Gly Ala Met Val Ile Asn Ile
        275                 280                 285

Gly Asp Thr Phe Met Ala Leu Ser Asn Gly Arg Tyr Lys Ser Cys Leu
            290                 295                 300

His Arg Ala Val Val Asn Gln Arg Arg Glu Arg Ser Leu Ala Phe
305                 310                 315                 320

Phe Leu Cys Pro Arg Glu Asp Arg Val Val Arg Pro Pro Ser Ala
                325                 330                 335

Ala Thr Pro Arg His Tyr Pro Asp Phe Thr Trp Ala Asp Leu Met Arg
                340                 345                 350

Phe Thr Gln Arg His Tyr Arg Ala Asp Thr Arg Thr Leu Asp Ala Phe
            355                 360                 365

Thr Arg Trp Leu Ala Pro Pro Ala Ala Asp Ala Ala Thr Ala Gln
370                 375                 380

Val Glu Ala Ala Ser
385

<210> SEQ ID NO 63
<211> LENGTH: 155
<212> TYPE: PRT
<213> ORGANISM: Sorghum bicolor

<400> SEQUENCE: 63

Phe Ala Ser Lys Leu Pro Trp Lys Glu Thr Leu Ser Phe Arg Tyr Ser
 1               5                  10                  15

Asp Asp Gln Gly Asp Gly Asp Val Val Val Asp Tyr Phe Val Asp Lys
            20                  25                  30

Leu Gly Asp Ala Tyr Arg His His Gly Glu Val Tyr Gly Arg Tyr Cys
        35                  40                  45

Ser Glu Met Ser Arg Leu Ser Leu Glu Leu Met Glu Val Leu Gly Glu
    50                  55                  60

Ser Leu Gly Val Gly Arg Arg His Phe Arg Arg Phe Gln Gly Asn
65                  70                  75              80

Gly Ser Ile Met Arg Leu Asn Tyr Tyr Pro Cys Gln Arg Pro Tyr
                85                  90                  95

Asp Thr Leu Gly Thr Gly Pro His Cys Asp Pro Thr Ser Leu Thr Ile
            100                 105                 110

Leu His Gln Asp Asp Val Gly Gly Leu Gln Val Phe Asp Gly Thr Gly
        115                 120                 125

Pro Gly Thr Gly Arg Trp Arg Ser Ile Arg Pro His Pro Gly Ala Phe
    130                 135                 140

Val Val Asn Ile Gly Asp Thr Phe Met Ala Leu
145                 150                 155
```

<210> SEQ ID NO 64
<211> LENGTH: 363
<212> TYPE: PRT
<213> ORGANISM: Lolium perenne

<400> SEQUENCE: 64

| Met | Val | Gln | Pro | Val | Phe | Asp | Ala | Ala | Leu | Leu | Ser | Gly | Gln | Ser | Asp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ile Pro Ser Gln Phe Ile Trp Pro Ala Asp Glu Ser Pro Ser Pro Asp
         20                  25                  30

Ala Thr Glu Glu Leu His Val Pro Leu Ile Asp Ile Gly Gly Leu Leu
         35                  40                  45

Ser Gly Asp Arg Val Ala Ala Glu Val Thr Arg Leu Val Gly Asp
 50                  55                  60

Ala Cys Glu Arg His Gly Phe Phe Gln Val Val Asn His Gly Ile Asp
 65                  70                  75                  80

Ala Glu Leu Leu Ala Asp Ala His Arg Cys Val Asp Ala Phe Phe Thr
                 85                  90                  95

Met Ser Leu Gln Gly Lys Gln Arg Ala Leu Arg Arg Pro Gly Glu Ser
                 100                 105                 110

Cys Gly Tyr Ala Ser Ser Phe Thr Gly Arg Phe Ala Ser Lys Leu Pro
                 115                 120                 125

Trp Lys Glu Thr Leu Ser Phe Arg Ser Cys Pro Ser Glu Pro Asp Leu
130                 135                 140

Val Val Glu Tyr Ile Val Ala Thr Leu Gly Glu Asp His Arg Arg Leu
145                 150                 155                 160

Gly Glu Val Tyr Ala Arg Tyr Cys Ser Glu Met Ser Arg Leu Ser Leu
                 165                 170                 175

Glu Ile Met Glu Val Leu Gly Glu Ser Leu Gly Val Gly Arg Ala His
                 180                 185                 190

Tyr Arg Arg Phe Phe Glu Gly Asn Glu Ser Ile Met Arg Leu Asn Tyr
                 195                 200                 205

Tyr Pro Pro Cys Gln Arg Pro Asn Glu Thr Leu Gly Thr Gly Pro His
         210                 215                 220

Cys Asp Pro Thr Ser Leu Thr Ile Leu His Gln Asp Asp Val Gly Gly
225                 230                 235                 240

Leu Gln Val His Ala Asp Gly Arg Trp Leu Ser Ile Arg Pro Arg Ala
                 245                 250                 255

Asp Ala Phe Val Val Asn Ile Gly Asp Thr Phe Met Ala Leu Ser Asn
                 260                 265                 270

Gly Arg Tyr Lys Ser Cys Leu His Arg Ala Val Val Asn Ser Arg Val
         275                 280                 285

Pro Arg Lys Ser Leu Ala Phe Phe Leu Cys Pro Glu Met Asp Lys Val
         290                 295                 300

Val Ala Pro Pro Gly Thr Leu Val Asp Glu Ala Asn Pro Arg Ala Tyr
305                 310                 315                 320

Pro Asp Phe Thr Trp Arg Ala Leu Leu Asp Phe Thr Gln Lys His Tyr
                 325                 330                 335

Arg Ala Asp Met Lys Thr Leu Glu Val Phe Ser Asp Trp Ile Gln Gln
                 340                 345                 350

Gly His Gln Pro Ala Ala Thr Thr Thr Thr
         355                 360

<210> SEQ ID NO 65
<211> LENGTH: 362

```
<212> TYPE: PRT
<213> ORGANISM: Lolium perenne

<400> SEQUENCE: 65

Met Val Gln Pro Val Phe Asp Ala Ala Leu Leu Ser Ala Gln Ser Asp
1               5                   10                  15

Ile Pro Ser Gln Phe Ile Trp Pro Ala Asp Glu Ser Pro Thr Pro Asp
            20                  25                  30

Ala Thr Glu Glu Leu His Val Pro Leu Ile Asp Ile Gly Gly Leu Leu
        35                  40                  45

Ser Gly Asp Arg Glu Ala Ala Glu Val Thr Arg Leu Val Gly Asp
50                  55                  60

Ala Cys Glu Arg His Gly Phe Phe Gln Val Val Asn His Gly Ile Asp
65                  70                  75                  80

Ala Glu Leu Leu Gly His Ala Arg Cys Val Asp Ala Phe Phe Thr Met
                85                  90                  95

Ser Leu Gln Asp Lys Gln Arg Ala Leu Arg Arg Pro Gly Glu Ser Cys
            100                 105                 110

Gly Tyr Ala Ser Ser Phe Thr Gly Arg Phe Ala Ser Lys Leu Pro Trp
        115                 120                 125

Lys Glu Thr Leu Ser Phe Arg Ser Cys Pro Ser Glu Pro Asp Leu Val
    130                 135                 140

Val Asp Tyr Ile Val Ala Thr Leu Gly Glu Asp His Arg Arg Leu Gly
145                 150                 155                 160

Glu Val Tyr Ala Arg Tyr Cys Ser Glu Met Ser Arg Leu Ser Leu Glu
                165                 170                 175

Ile Met Glu Val Leu Gly Glu Ser Leu Gly Val Gly Arg Ala His Tyr
            180                 185                 190

Arg Arg Phe Phe Glu Gly Asn Glu Ser Ile Met Arg Leu Asn Tyr Tyr
        195                 200                 205

Pro Pro Cys Gln Arg Pro Asn Glu Thr Leu Gly Thr Gly Pro His Cys
    210                 215                 220

Asp Pro Thr Ser Leu Thr Ile Leu His Gln Asp Asp Val Gly Gly Leu
225                 230                 235                 240

Gln Val His Ala Asp Gly Arg Trp Leu Ser Ile Arg Pro Arg Ala Asp
                245                 250                 255

Ala Phe Val Val Asn Ile Gly Asp Thr Phe Met Ala Leu Ser Asn Gly
            260                 265                 270

Arg Tyr Lys Ser Cys Leu His Arg Ala Val Val Asn Ser Arg Val Pro
        275                 280                 285

Arg Lys Ser Leu Ala Phe Phe Leu Cys Pro Glu Met Asp Lys Val Val
    290                 295                 300

Ala Pro Pro Gly Thr Leu Val Asp Glu Ala Asn Pro Arg Ala Tyr Pro
305                 310                 315                 320

Asp Phe Thr Trp Arg Ala Leu Leu Asp Phe Thr Gln Lys His Tyr Arg
                325                 330                 335

Ala Asp Met Lys Thr Leu Glu Val Phe Ser Asp Trp Ile Gln Gln Gly
            340                 345                 350

His Gln Pro Ala Ala Thr Thr Thr Thr
        355                 360

<210> SEQ ID NO 66
<211> LENGTH: 363
<212> TYPE: PRT
<213> ORGANISM: Lolium perenne
```

<400> SEQUENCE: 66

```
Met Val Gln Pro Val Phe Asp Ala Ala Leu Leu Ser Gly Gln Ser Asp
1               5                   10                  15

Ile Pro Ser Gln Phe Ile Trp Pro Ala Asp Glu Ser Pro Ser Pro Asp
            20                  25                  30

Ala Thr Glu Glu Leu His Val Pro Leu Ile Asp Ile Gly Gly Leu Leu
        35                  40                  45

Ser Gly Asp Arg Ala Ala Ala Glu Val Thr Arg Leu Val Gly Asp
    50                  55                  60

Ala Cys Glu Arg His Gly Phe Phe Gln Val Val Asn His Gly Ile Asp
65                  70                  75                  80

Ala Glu Leu Leu Ala Asp Ala His Arg Cys Val Asp Ala Phe Phe Thr
                85                  90                  95

Met Ser Leu Gln Gly Lys Gln Arg Ala Leu Arg Arg Pro Gly Glu Ser
            100                 105                 110

Cys Gly Tyr Ala Ser Ser Phe Thr Gly Arg Phe Ala Ser Lys Leu Pro
        115                 120                 125

Trp Lys Glu Thr Leu Ser Phe Arg Ser Cys Pro Ser Glu Pro Asp Leu
    130                 135                 140

Val Val Glu Tyr Ile Val Ala Thr Leu Gly Glu Asp His Arg Arg Leu
145                 150                 155                 160

Gly Glu Ala Tyr Ala Arg Tyr Cys Ser Glu Met Ser Arg Leu Ser Leu
                165                 170                 175

Glu Ile Met Glu Val Leu Gly Glu Ser Leu Gly Val Gly Arg Ala His
            180                 185                 190

Tyr Arg Arg Phe Phe Glu Gly Asn Glu Ser Ile Met Arg Leu Asn Tyr
        195                 200                 205

Tyr Pro Pro Cys Gln Arg Pro Asn Glu Thr Leu Gly Thr Gly Pro His
    210                 215                 220

Cys Asp Pro Thr Ser Leu Thr Ile Leu His Gln Asp Asp Val Gly Gly
225                 230                 235                 240

Leu Gln Val His Ala Asp Gly Arg Trp Leu Ser Ile Arg Pro Arg Ala
                245                 250                 255

Asp Ala Phe Val Val Asn Ile Gly Asp Thr Phe Met Ala Leu Ser Asn
            260                 265                 270

Gly Arg Tyr Lys Ser Cys Leu His Arg Ala Val Val Asn Ser Arg Val
        275                 280                 285

Pro Arg Lys Ser Leu Ala Phe Phe Leu Cys Pro Glu Met Asp Lys Val
    290                 295                 300

Val Ala Pro Pro Glu Thr Leu Val Asp Glu Ala Asn Pro Arg Ala Tyr
305                 310                 315                 320

Pro Asp Phe Thr Trp Arg Ala Leu Leu Asp Phe Thr Gln Lys His Tyr
                325                 330                 335

Arg Ala Asp Met Lys Thr Leu Glu Val Phe Ser Asp Trp Ile Gln Gln
            340                 345                 350

Gly His Gln Pro Ala Ala Thr Thr Thr Thr
        355                 360
```

<210> SEQ ID NO 67
<211> LENGTH: 382
<212> TYPE: PRT
<213> ORGANISM: Lolium perenne

<400> SEQUENCE: 67

```
Met Val Gln Pro Val Phe Asp Ala Ala Leu Leu Ser Gly Gln Ser Asp
 1               5                  10                  15

Ile Pro Ser Gln Phe Ile Trp Pro Ala Asp Glu Ser Pro Ser Pro Asp
             20                  25                  30

Ala Thr Glu Glu Leu His Val Pro Leu Ile Asp Ile Gly Gly Leu Leu
             35                  40                  45

Ser Gly Asp Arg Glu Ala Ala Glu Val Thr Arg Leu Val Gly Asp
 50                  55                  60

Ala Cys Glu Arg His Gly Phe Phe Gln Val Val Asn His Gly Ile Asp
 65                  70                  75                  80

Ala Glu Leu Leu Ala Asp Ala His Arg Cys Val Asp Ala Phe Phe Thr
             85                  90                  95

Met Ser Leu Gln Asp Lys Gln Arg Ala Leu Arg Arg Pro Gly Glu Ser
             100                 105                 110

Cys Gly Tyr Ala Ser Ser Phe Thr Gly Arg Phe Ala Ser Lys Leu Pro
             115                 120                 125

Trp Lys Glu Thr Leu Ser Phe Arg Ser Cys Pro Ser Glu Pro Asp Leu
 130                 135                 140

Val Val Asp Tyr Ile Val Ala Thr Leu Gly Glu Asp His Arg Arg Leu
145                 150                 155                 160

Gly Glu Val Tyr Ala Arg Tyr Cys Ser Glu Met Ser Arg Leu Ser Leu
             165                 170                 175

Glu Ile Met Glu Val Leu Gly Glu Ser Leu Gly Val Gly Arg Ala His
             180                 185                 190

Tyr Arg Arg Phe Phe Glu Gly Asn Glu Ser Ile Met Arg Leu Asn Tyr
             195                 200                 205

Tyr Pro Pro Cys Gln Arg Pro Asn Gly Thr Leu Gly Thr Gly Pro His
             210                 215                 220

Cys Asp Pro Thr Ser Leu Thr Ile Leu His Gln Asp Val Gly Gly
225                 230                 235                 240

Leu Gln Val His Ala Asp Gly Arg Trp Leu Ser Ile Arg Pro Arg Ala
             245                 250                 255

Asp Ala Phe Val Val Asn Ile Gly Asp Thr Phe Met Ala Leu Ser Asn
             260                 265                 270

Gly Arg Tyr Lys Ser Cys Leu His Arg Ala Val Val Asn Ser Arg Val
             275                 280                 285

Pro Arg Lys Ser Leu Ala Phe Phe Leu Cys Pro Glu Met Asp Lys Val
             290                 295                 300

Val Ala Pro Pro Gly Thr Ser Val Asp Glu Ala Asn Pro Arg Ala Tyr
305                 310                 315                 320

Pro Asp Phe Thr Trp Arg Ala Leu Leu Asp Phe Thr Gln Lys His Tyr
             325                 330                 335

Arg Ala Asp Met Lys Thr Leu Glu Val Phe Ser Asp Trp Ile Gln Gln
             340                 345                 350

Gly His Gln Pro Ala Ala Thr Thr Thr Thr Gln Asp Gln Arg Thr
             355                 360                 365

Tyr Thr Ala Ser Ala Ser Leu His Leu Leu Ala Cys Cys Thr
 370                 375                 380

<210> SEQ ID NO 68
<211> LENGTH: 370
<212> TYPE: PRT
<213> ORGANISM: Zea mays
```

<400> SEQUENCE: 68

```
Met Val Leu Ala Ala His Asp Pro Pro Leu Val Phe Asp Ala Ala
  1               5                  10                  15

Arg Leu Ser Gly Leu Ser Asp Ile Pro Gln Gln Phe Ile Trp Pro Ala
             20                  25                  30

Asp Glu Ser Pro Thr Pro Asp Ser Ala Glu Glu Leu Ala Val Pro Leu
             35                  40                  45

Ile Asp Leu Ser Gly Asp Ala Ala Glu Val Val Arg Gln Val Arg Arg
 50                  55                  60

Ala Cys Asp Leu His Gly Phe Phe Gln Val Val Gly His Gly Ile Asp
 65                  70                  75                  80

Ala Ala Leu Thr Ala Glu Ala His Arg Cys Met Asp Ala Phe Phe Thr
                 85                  90                  95

Leu Pro Leu Pro Asp Lys Gln Arg Ala Gln Arg Arg Gln Gly Asp Ser
            100                 105                 110

Cys Gly Tyr Ala Ser Ser Phe Thr Gly Arg Phe Ala Ser Lys Leu Pro
            115                 120                 125

Trp Lys Glu Thr Leu Ser Phe Arg Tyr Thr Asp Asp Asp Gly Asp
130                 135                 140

Lys Ser Lys Asp Val Val Ala Ser Tyr Phe Val Asp Lys Leu Gly Glu
145                 150                 155                 160

Gly Tyr Arg His His Gly Glu Val Tyr Gly Arg Tyr Cys Ser Glu Met
                165                 170                 175

Ser Arg Leu Ser Leu Glu Leu Met Glu Val Leu Gly Glu Ser Leu Gly
            180                 185                 190

Val Gly Arg Arg His Phe Arg Arg Phe Phe Gln Gly Asn Asp Ser Ile
            195                 200                 205

Met Arg Leu Asn Tyr Tyr Pro Pro Cys Gln Arg Pro Tyr Asp Thr Leu
210                 215                 220

Gly Thr Gly Pro His Cys Asp Pro Thr Ser Leu Thr Ile Leu His Gln
225                 230                 235                 240

Asp Asp Val Gly Gly Leu Gln Val Phe Asp Ala Ala Leu Ala Trp Arg
                245                 250                 255

Ser Val Arg Pro Arg Pro Gly Ala Phe Val Val Asn Ile Gly Asp Thr
            260                 265                 270

Phe Met Ala Leu Ser Asn Gly Arg Tyr Arg Ser Cys Leu His Arg Ala
275                 280                 285

Val Val Asn Ser Arg Val Ala Arg Arg Ser Leu Ala Phe Phe Leu Cys
            290                 295                 300

Pro Glu Met Asp Lys Val Val Arg Pro Lys Glu Leu Val Asp Asp
305                 310                 315                 320

Ala Asn Pro Arg Ala Tyr Pro Asp Phe Thr Trp Arg Thr Leu Leu Asp
                325                 330                 335

Phe Thr Met Arg His Tyr Arg Ser Asp Met Arg Thr Leu Glu Ala Phe
            340                 345                 350

Ser Asn Trp Leu Ser Thr Arg Ser Asn Gly Gly Gln His Leu Leu Glu
            355                 360                 365

Lys Lys
    370
```

<210> SEQ ID NO 69
<211> LENGTH: 369
<212> TYPE: PRT
<213> ORGANISM: Zoysia japonica

<400> SEQUENCE: 69

```
Met Ala Ala Ser Thr Pro Asn Gly Asp Pro Val Arg Ser Leu
1               5                   10                  15

Ala Thr Thr Val Pro Val Gln Ala Val Leu Phe Asp Ile Asp Gly Thr
            20                  25                  30

Leu Cys Asp Ser Asp Pro Leu His His Val Ala Phe Gln Glu Leu Leu
        35                  40                  45

Leu Glu Ile Gly Tyr Asn Asn Gly Val Pro Ile Gly His Gly Phe Phe
    50                  55                  60

Gln Val Val Asn His Gly Ile Asp Gln Glu Pro Leu Ala Glu Ala His
65                  70                  75                  80

Arg Cys Met Asp Asn Phe Phe Thr Leu Pro Leu Pro Glu Lys Gln Arg
                85                  90                  95

Ala Gln Arg Arg Gln Gly Glu Ser Cys Gly Tyr Ala Ser Ser Phe Thr
            100                 105                 110

Gly Arg Phe Ala Cys Lys Leu Pro Trp Lys Glu Thr Leu Ser Phe Arg
        115                 120                 125

Tyr Ser Ser Asn Pro Ser Ser Pro Asp Leu Val Val Asp Tyr Phe Val
    130                 135                 140

Glu Lys Leu Gly Glu Asp Tyr Arg His His Gly Ala Val Tyr Ala Arg
145                 150                 155                 160

Tyr Cys Ser Glu Met Ser Arg Leu Ser Leu Glu Met Met Gly Ile Leu
                165                 170                 175

Gly Glu Ser Leu Gly Val Gly Arg Asp His Phe Arg Arg Phe Phe Gln
            180                 185                 190

Pro Asn Glu Ser Ile Met Arg Leu Asn Tyr Tyr Pro Pro Cys Gln Arg
        195                 200                 205

Pro Leu Glu Thr Leu Gly Thr Gly Pro His Cys Asp Pro Thr Ser Leu
    210                 215                 220

Thr Ile Leu His Gln Asp His Val Gly Gly Leu Gln Val Phe Thr Asp
225                 230                 235                 240

Gly Arg Trp Arg Ser Ile Arg Pro His Ala Gly Ala Phe Val Val Asn
                245                 250                 255

Ile Gly Asp Thr Phe Thr Gly Ala Leu Gln Arg Pro Val Pro Lys Leu
            260                 265                 270

Leu His Arg Ala Val Asn Ser Leu Val Pro Arg Lys Ser Leu Ala
        275                 280                 285

Phe Phe Leu Cys Pro Glu Met Asp Lys Val Val Cys Pro Pro Glu Gly
    290                 295                 300

Leu Val Glu Ala Gly Met Pro Arg Ala Tyr Pro Asp Phe Thr Trp Arg
305                 310                 315                 320

Thr Leu Leu Asp Phe Thr Gln Arg Arg Tyr Arg Ala Asp Met Arg Thr
                325                 330                 335

Leu Glu Val Phe Ser Asn Trp Leu Arg His Gly Gln Asp Lys Thr Pro
            340                 345                 350

Pro Thr Ser Leu Ile His Arg Ser Lys Ile Val Thr Val His His Pro
        355                 360                 365

Ser
```

<210> SEQ ID NO 70
<211> LENGTH: 380
<212> TYPE: PRT
<213> ORGANISM: Musa balbisia

<400> SEQUENCE: 70

```
Met Asp Ser Val Ser Pro Val Thr Leu Asp Leu Asn Lys Glu Glu Gly
1               5                   10                  15

His Cys Ser Asn Ser Ala Val Val Phe Asp Thr Ser Phe Leu Arg Arg
            20                  25                  30

Gln Ala Lys Ile Pro Glu Ser Phe Val Trp Pro Arg Ser Glu Arg Pro
        35                  40                  45

His Pro Leu Glu Glu Leu Glu Val Pro Val Val Asp Leu Arg Gly Leu
    50                  55                  60

Phe Glu Gly Asp Glu Ala Ser Ile Ser Arg Ala Glu Ala Ser Arg
65                  70                  75                  80

Ala Ala Cys Val Arg His Gly Phe Phe Gln Val Ile Asn His Lys Val
                85                  90                  95

Asp Ala Lys Val Ser Gly Asp Ala Leu Asp Ala Ala Gly Asp Phe Phe
            100                 105                 110

Lys Leu Pro Leu Ser Thr Lys Leu Arg Ala Arg Gln Pro Gly Ser
        115                 120                 125

Ala Trp Gly Tyr Val Gly Ala His Ala Asp Arg Phe Ala Ser Lys Leu
    130                 135                 140

Pro Trp Lys Glu Thr Leu Thr Phe Gly Tyr Asp Tyr Gly Glu Arg Gly
145                 150                 155                 160

Asp Gly Val Val Asp Tyr Phe Thr Ser Lys Leu Gly Glu Gly Phe Glu
                165                 170                 175

Pro Met Gly Arg Val Tyr Arg Tyr Cys Glu Ala Met Lys Glu Leu
            180                 185                 190

Ser Leu Ser Ile Met Glu Leu Leu Gly Ile Ser Leu Gly Val Gly Arg
        195                 200                 205

Glu Tyr Tyr Arg Gln Phe Phe Glu Asp Gly Ser Ser Ile Met Arg Cys
    210                 215                 220

Asn Ser Tyr Pro Pro Cys Gln Glu Pro Glu Leu Ala Leu Gly Thr Gly
225                 230                 235                 240

Pro His Cys Asp Pro Thr Ala Leu Thr Ile Leu Leu Gln Asp Gln Val
                245                 250                 255

Gly Gly Leu Gln Val Phe Thr Glu Gly Lys Trp Gln Ala Val Arg Pro
            260                 265                 270

Val Arg Ser Ala Val Val Ile Asn Ile Gly Asp Thr Phe Met Ala Leu
        275                 280                 285

Ser Asn Gly Arg Tyr Lys Ser Cys Leu His Arg Ala Val Val Asn Ser
    290                 295                 300

Glu Arg Glu Arg Leu Ser Leu Ala Phe Phe Val Cys Pro Arg Gly Asp
305                 310                 315                 320

Arg Val Val Arg Pro Arg Glu Leu Leu Leu Leu Glu Glu Glu
                325                 330                 335

Glu Glu Ala Val Pro Arg Ala Phe Pro Asp Phe Thr Trp Thr Glu Leu
            340                 345                 350

Leu Glu Phe Thr Gln Thr His Tyr Arg Ala Asp Thr Thr Thr Leu Gln
        355                 360                 365

Ser Phe Ser Arg His Arg Phe Leu Ala Ser Ser Pro
    370                 375                 380
```

<210> SEQ ID NO 71
<211> LENGTH: 6
<212> TYPE: PRT

```
-continued

<213> ORGANISM: Artificial Sequence
<220> FEATURE:
<223> OTHER INFORMATION: Synthetic Construct

<400> SEQUENCE: 71

Leu Pro Trp Lys Glu Thr
1               5

<210> SEQ ID NO 72
<211> LENGTH: 4
<212> TYPE: PRT
<213> ORGANISM: Artificial Sequence
<220> FEATURE:
<223> OTHER INFORMATION: Synthetic Construct

<400> SEQUENCE: 72

Asn Tyr Tyr Pro
1

<210> SEQ ID NO 73
<211> LENGTH: 3
<212> TYPE: PRT
<213> ORGANISM: Artificial Sequence
<220> FEATURE:
<223> OTHER INFORMATION: Synthetic Construct
<221> NAME/KEY: VARIANT
<222> LOCATION: (1)...(3)
<223> OTHER INFORMATION: Xaa = Any Amino Acid

<400> SEQUENCE: 73

His Xaa Asp
1
```

US 7,807,878 B2

TRANSGENIC TREES EXHIBITING INCREASED GROWTH, BIOMASS PRODUCTION AND XYLEM FIBRE LENGTH, AND METHODS FOR THEIR PRODUCTION

RELATED APPLICATIONS

This application is a continuation-in-part of U.S. patent application Ser. No. 10/221,296 filed Sep. 6, 2002, which is the National Stage of International Application No. PCT/SE01/00451, filed Mar. 2, 2001, which claims the benefit of U.S. Provisional Application Ser. No. 60/240,319, filed Oct. 13, 2000 and Swedish Patent application 0000751-8, filed Mar. 7, 2000, each of the foregoing which is hereby incorporated by reference.

FIELD OF THE INVENTION

The present invention concerns transgenic trees exhibiting improved properties, and in particular properties of economic importance, such as increased growth rate, biomass production and xylem fibre length; transgenic plants, seeds, plant cells and other types of propagating material, as well as methods for their production.

BACKGROUND

A major disadvantage with traditional tree breeding, especially for forest tree species, is the slow progress due to their long generation periods. However, by taking advantage of recent developments in gene technology the time required to produce a new variety could be reduced significantly. In addition, a biotechnological approach would allow closer targeting of traits considered desirable by the forest and pulp industries, in specific tree species.

To date, most applications of genetic engineering of trees have focused on modifying lignin biosynthesis, resulting in trees with less lignin or a modified lignin composition, earlier flowering, pest or herbicide resistance. In order to change growth and development processes in trees, the manipulation of plant hormone levels, or the hormone sensitivity, would also be of interest. However, as yet there have only been few examples of the modification of plant hormone levels in trees. These have mainly been accomplished by directly altering endogenous IAA biosynthesis or cytokinin biosynthesis or indirectly by modifying various hormone pools using the *Agrobacterium* rolC gene. Although such modifications in all cases lead to trees with altered growth characteristics and wood properties, so far no improvements with a clear practical application have been obtained.

Gibberellins (GAs) are a group of more than 100 tetracyclic diterpenes, some of which are essential endogenous regulators that influence growth and development processes throughout the plant life cycle, e.g. shoot elongation, the expansion and shape of leaves, flowering and seed germination. The best examples illustrating the importance of GAs in control of shoot elongation are GA-deficient mutants of *Arabidopsis*, maize and pea. These have reduced levels of active GA(s) compared to wild type plants, resulting in a dwarfed phenotype due to a reduction in internode length. The phenotype of such GA-deficient mutants can be completely restored by the application of an active GA. At the cellular level, GAs have been found to promote both cell division and cell elongation.

Biosynthesis of GAs in planta occurs through the isoprenoid pathway from mevalonic acid. Gibberellin levels are mainly regulated by transcriptional control of gibberellin biosynthesis genes. In particular, the multifunctional enzyme gibberellin 20-oxidase (GA 20-ox) is a key-enzyme in controlling GA biosynthesis (FIG. 1). It catalyses the stepwise conversion of the C-20 gibberellins, $GA_{12}/GA_{53}$, by three successive oxidations to $GA_9/GA_{20}$, which are the immediate precursors of the active gibberellins, $GA_4$ and $GA_1$, respectively. The expression of the GA 20-oxidase gene is down regulated by the action of $GA_{1/4}$, suggesting that direct end-product repression is involved in regulation of the gene. In addition, some authors have suggested that GA 20-oxidase is photoperiodically regulated at the transcription level.

Application of chemicals that alter GA levels in the plant is a common practise in traditional agriculture and horticulture. Inhibitors of GA biosynthesis are especially commonly used as growth retardants in cereals and ornamental plants. In order to reduce the use of these chemicals, a biological approach like genetic modification of endogenous GA biosynthesis would have clear advantages. Using *Arabidopsis* as a model organism it has been shown that it is possible to change GA levels by modifying GA 20-oxidase enzyme levels and that this results in plants with altered growth and development patterns. Transgenic *Arabidopsis* expressing the GA 20-oxidase in a sense orientation shows earlier flowering and taller stems than wild type plants, whereas antisense plants have the reverse properties [Coles, J. P. et al. Modification of gibberellin production and plant development in *Arabidopsis* by sense and antisense expression of gibberellin 20-oxidase genes. *Plant J*. 17, 547-556 (1999)].

Modification of GA biosynthesis in a higher species, such as trees would be of additional interest since this would open up ways to modify wood. Previous hormone application studies have shown that GAs are required for the differentiation of xylem fibres, and that they have pronounced effects on the length of secondary xylem fibres and on both longitudinal and radial growth in hard wood species and conifers.

Obviously there remains a need for improved methods for modification of the growth properties of trees, in particular properties of technical and economical interest, such as growth rate, biomass increase and fibre length. Likewise, there remains a need of transgenic trees, exhibiting improved properties, such as increased growth rate, stem volume and xylem fibre length. Consequently, the objective of the present invention is to provide such improved methods and transgenic trees. Another objective is to reduce or eliminate the use of growth influencing chemicals in forestry.

PRIOR ART

It has been shown (Huang, S. et al., Overexpression of 20-Oxidase confers a gibberellin-overproduction phenotype in *Arabidopsis*, Plant Physiol., 1998, vol. 118, p 773-781) that the level of active GAs were raised following overexpression of GA 20-oxidase in *Arabidopsis thaliana*. This finding is however not directly transferable on the present invention.

Most dicotyledons and all gymnosperm undergo some degree of secondary thickening. The amount of thickening depends on whether the mature plant is a herbaceous or a woody (arborescent) plant. For example an *Arabidopsis* plant will only produce secondary thickening under special conditions whereas a woody species, for example *Populus*, will undergo a high degree of secondary growth. The low degree of secondary thickening in herbaceous species will also make it very difficult to predict how specific genetic changes in herbaceous species corresponds in woody species in regards to changes in wood formation.

As an example, by over expressing the GA 20-oxidase in *Arabidopsis thaliana* the level of active GAs in the plant can be raised, as shown by Huang et al. (Supra). The transgenic plant phenotype included a dramatic cell elongation in all tissues. The petioles, inflorescence stems and leaves all showed cell elongation. It is clear from these results that the enhanced gibberellin levels have an effect on cell elongation from germination. However, from these results it is impossible to predict what the effect of GA 20-oxidase over expression in a woody plant would be. Cell division in the cambial meristem in a woody plant is under the control of several different hormones and physical constraints not found in an annual plant such as *Arabidopsis thaliana*.

It was therefore surprising that there would be increased cell elongation of cells (fibres) originating from the cambium, and that it would be an increase in biomass caused by increased cambial cell division. It would not be obvious to one skilled in the art to over express GA 20-oxidase to increase wood biomass and fibre elongation.

Increase in the diameter of tree stems occurs primarily from meristematic activity in the vascular cambium, a cylindrical lateral meristem located between the xylem and phloem of the stem, branches, and woody roots. Two types of cell division occur in the cambium: additive and multiplicative. Additive division involves periclinal division of fusiform cambial initials to produce xylem and phloem mother cells that in turn divide to produce xylem and phloem cells. Multiplicative division involves anticlinal division of fusiform initials that provide for circumferential expansion of the cambium. After xylem and phloem cells are cut off by the cambial mother cells, they differentiate in an ordered sequence of events that includes cell enlargement, secondary wall formation, lignification and loss of protoplasts. These events do not occur stepwise, but rather as overlapping phases.

SUMMARY OF THE INVENTION

It is an object of the present invention to provide transgenic plants, seeds and plant cells, exhibiting improved growth parameters and in particular improved parameters of economical interest, such as increased growth rate, biomass increase and xylem fibre length. It is another object of the invention to provide a method for the production and proliferation of said transgenic plants. The above objects, and others not explicitly mentioned, are fulfilled through a transgenic woody plant having a DNA sequence coding for the expression of a polypeptide exhibiting GA 20-oxidase activity functionally inserted in the plant genome. Further embodiments are as defined in the attached dependent and independent claims, incorporated herein by reference.

Other features and advantages of the invention will be apparent form the following, non-limiting description and examples, and from the claims.

BRIEF DESCRIPTION OF THE DRAWINGS

The invention will be described in closer detail below, in the description and accompanying examples and drawings, in which.

DESCRIPTION OF THE INVENTION

The present inventors have surprisingly shown that ectopic over-expression of a GA 20-oxidase gene in trees, here exemplified by a temperate-zone deciduous tree, results in significant changes in growth rate, stem volume and xylem fibre length. A cDNA sequence (SEQ. ID. NO. 1) homologous to the *Arabidopsis thaliana* GA 20 oxidase sequence X83379 (EMBL accession number) encoding a polypeptide exhibiting GA 20 oxidase activity was used. Thus, the results obtained by the present inventors show that genetic modification of GA levels in trees can be used to modify traits that are extremely important for the forest, pulp and paper industries.

The results show that an endogenous elevation of the biologically active gibberellins $GA_1$ and $GA_4$ in trees will accelerate growth. This was demonstrated by expressing the AtGA20ox1 gene from *Arabidopsis* in hybrid aspen, *Populus tremula×tremuloides*, resulting in trees with faster height and diameter growth, larger leaves, longer xylem fibres and increased biomass. This phenotype is partly reminiscent of traits previously observed in transgenic *Arabidopsis* plants over-expressing the same GA 20-oxidase (Coles, J. P. et al., Modification of gibberellin production and plant development in *Arabidopsis* by sense and antisense expression of gibberellin 20-oxidase genes. *Plant J.* 17, 547-556 (1999). Such plants had longer hypocotyls, larger rosette leaves, longer petioles, and accelerated flowering compared to wild type plants.

However, studies regarding biomass increase and anatomical changes in transgenic *Arabidopsis* have not been reported. It is highly doubtful if an increased biomass would be achieved in transgenic *Arabidopsis*.

Figure 1:
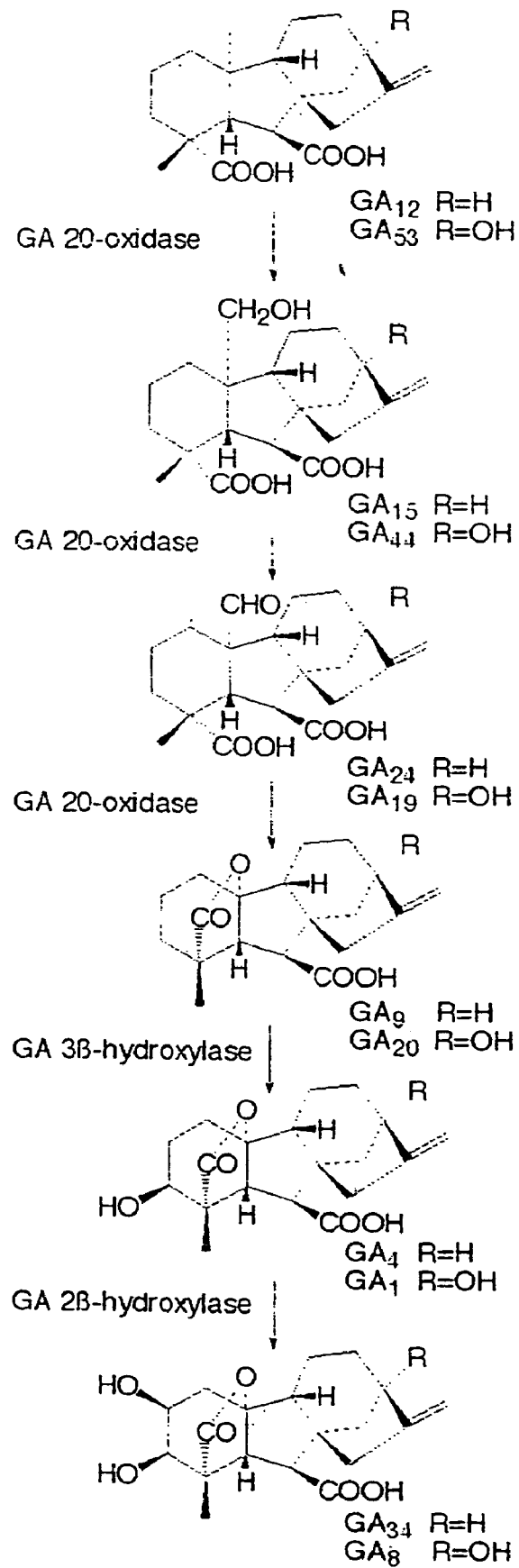
FIG. 1 shows the biosynthetic pathways converting $GA_{12}$ and $GA_{53}$ to the biologically active products $GA_4$ and $GA_1$, and their deactivated catabolites, $GA_{34}$ and $GA_8$. GA 20-oxidase catalyses the oxidation at the C-20 carbon.

There have been suggestions that the GA 20-oxidase is a key enzyme in the regulation of GA controlled growth [Hedden, P. & Kamiya, Y. Gibberellin biosynthesis: Enzymes, genes and their regulation. *Annu. Rev. Plant Physiol. Plant Mol. Biol.* 48, 431-460 (1997)]. The fact that transcription of the GA 20-oxidase gene is feedback regulated by the action of GAs, suggests that constitutive over-expression of the GA 20-oxidase gene will disturb the endogenous regulation of GA homeostasis. Here, over-expression of GA 20-oxidase in hybrid aspen resulted in an increase in $C_{19}$-GAs involved in both the early 13-hydroxylation pathway and the non-13-hydroxylation pathway (FIG. 1). Thus, there was no consistent difference in levels between $GA_1$ and $GA_4$, both of which are biologically active in *Populus*. The present results therefore are in agreement with previous GA measurements on transgenic GA 20-oxidase overproducing *Arabidopsis* plants. Furthermore, in both hybrid aspen and *Arabidopsis* there was a dramatic increase in the levels of the deactivated end-product, $GA_8$ (Table 1).

This has been suggested to be due to a slower turnover of $GA_8$ than $GA_1$. The relatively low levels of the other end-product, $GA_{34}$, formed by the non-13-hydroxylation pathway can be explained by a more rapid turnover of this compound than $GA_8$. In contrast to the $C_{19}$-GAs, a decrease in levels of $C_{20}$-GAs was observed in the transgenic plants. This is consistent with the fact that $C_{20}$-GAs are, by definition, substrates for the GA 20-oxidase (Table 1).

It is surprising that the elevated GA 20-oxidase expression has such marked effects in *Populus tremula×tremuloides*. This suggests that constitutive over-expression of the GA 20-oxidase gene disturb the endogenous regulation of GA homeostasis.

In the present study the inventors found differences in GA levels between leaf and stem tissues; increases in levels of the active $GA_1$ and $GA_4$ being highest in stem tissue. This could have been due to the AtGA20ox1 gene being expressed most strongly in the stem. In hybrid aspen, however, the CaMV 35S promoter is generally slightly more active in leaves than in the stem, although exceptions are known to occur. Therefore, the higher $GA_1$ and $GA_4$ levels in the stem are more likely due to differences in transport of GAs or in the biosynthesis of GA precursors. However, it can not be ruled out that there may be a difference in GA 3β-hydroxylase or GA 2β-hydroxylase activity in the leaves. In *Arabidopsis* it has been shown that 2β-hydroxylation is activated at the transcriptional level by active GAs.

Figure 3:
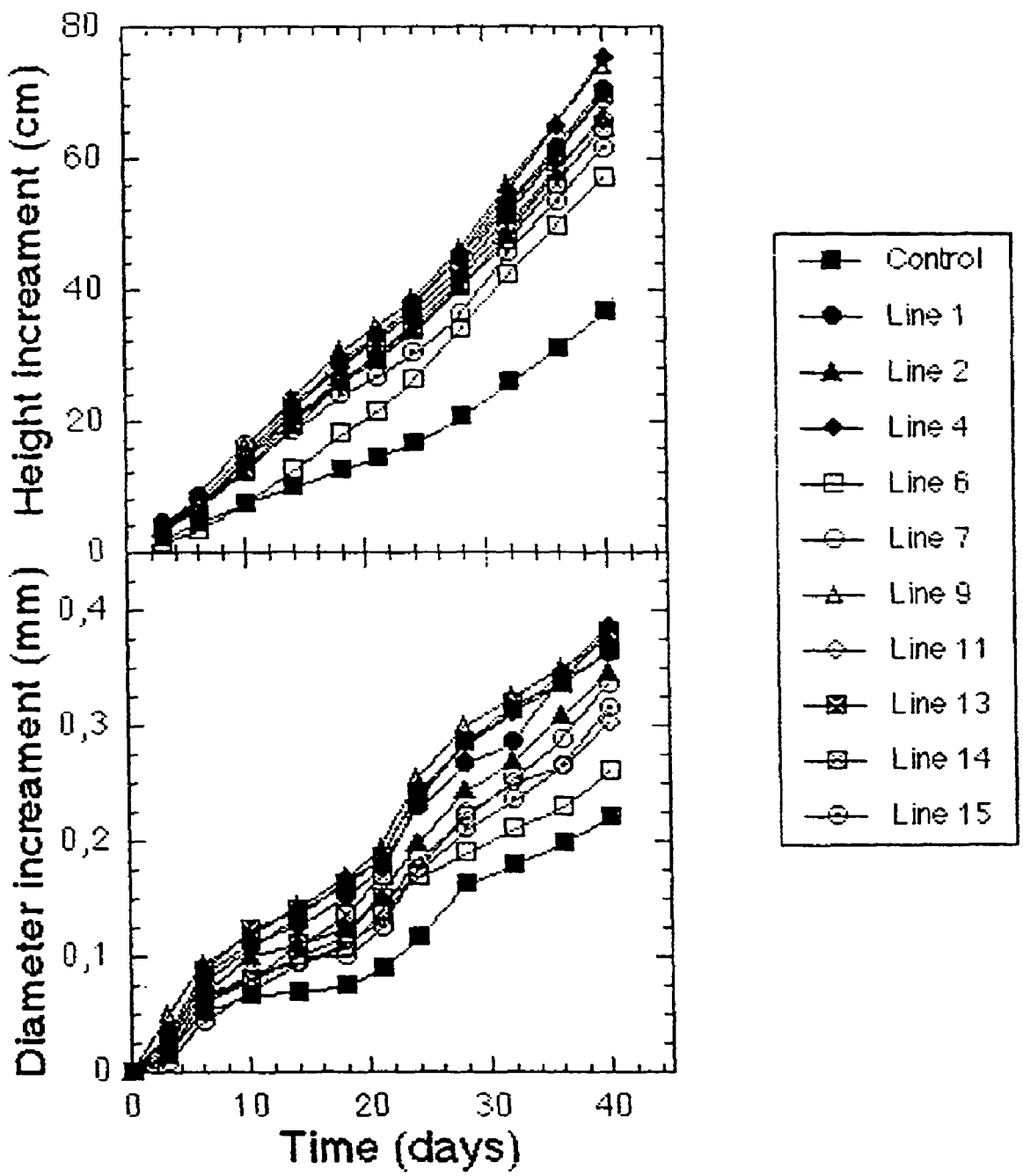
FIG. 3 shows the enhanced growth of transgenic hybrid aspen: the cumulative shoot elongation (upper diagram) and diameter growth (lower diagram) of various transgenic GA 20-oxidase over-expressing lines, after generation from tissue culture, potting and cultivation in a growth chamber for seven weeks (at time zero).
Figure 5:
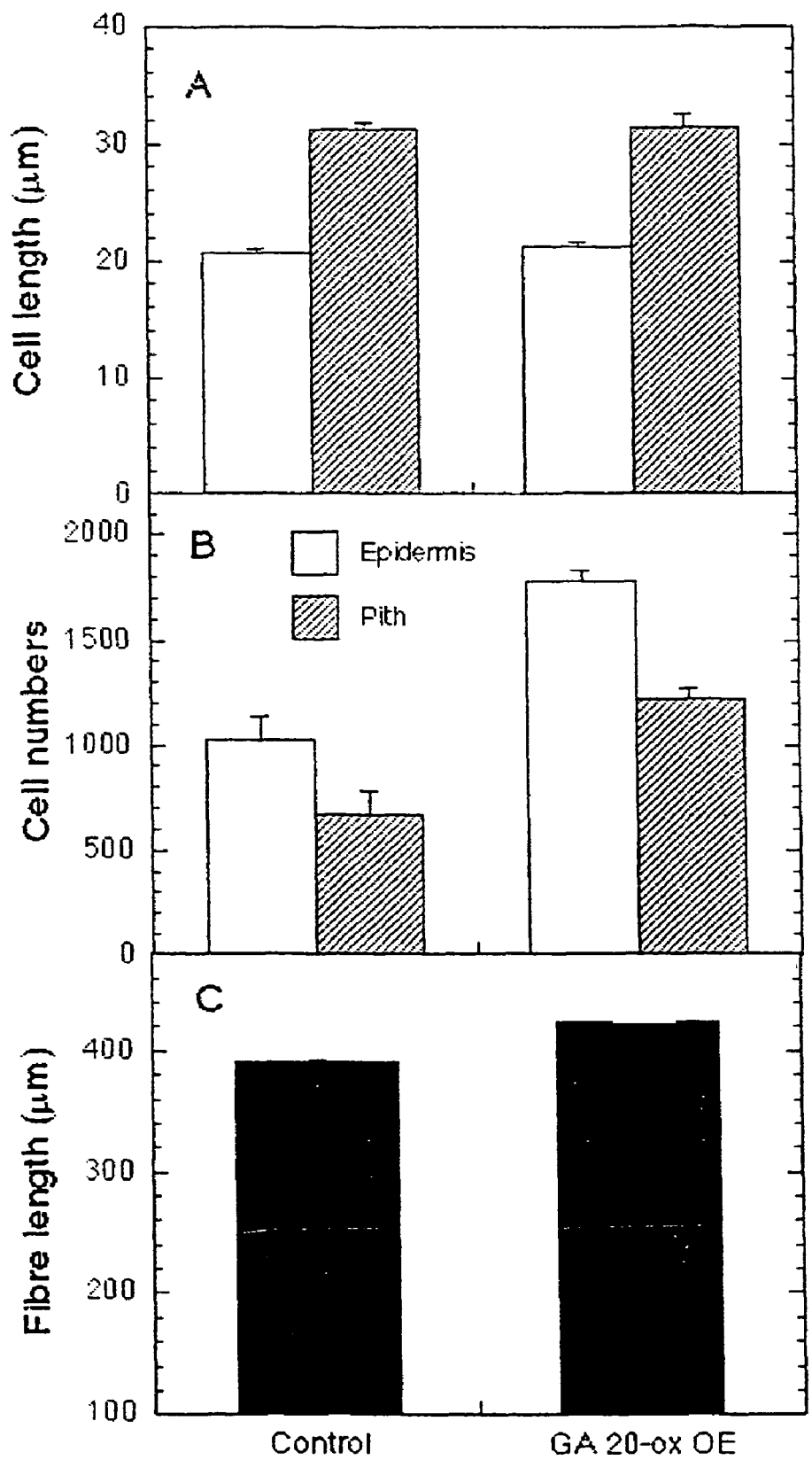
FIG. 5 illustrates the effects of GA 20-oxidase over-expression on (A) Cell lengths, (B) cell numbers per internode, (C) number of xylem fibres and (D) xylem fibre length. Cell lengths and cell numbers were measured in fully elongated internodes of actively growing plants as was number of xylem fibres. Data for the GA 20-oxidase over-expressing lines are means for nine independently generated lines, respectively. Fibre length values for non-elongating plants represent means for three independently generated lines. The vertical bars represent SE.
Figure 6:
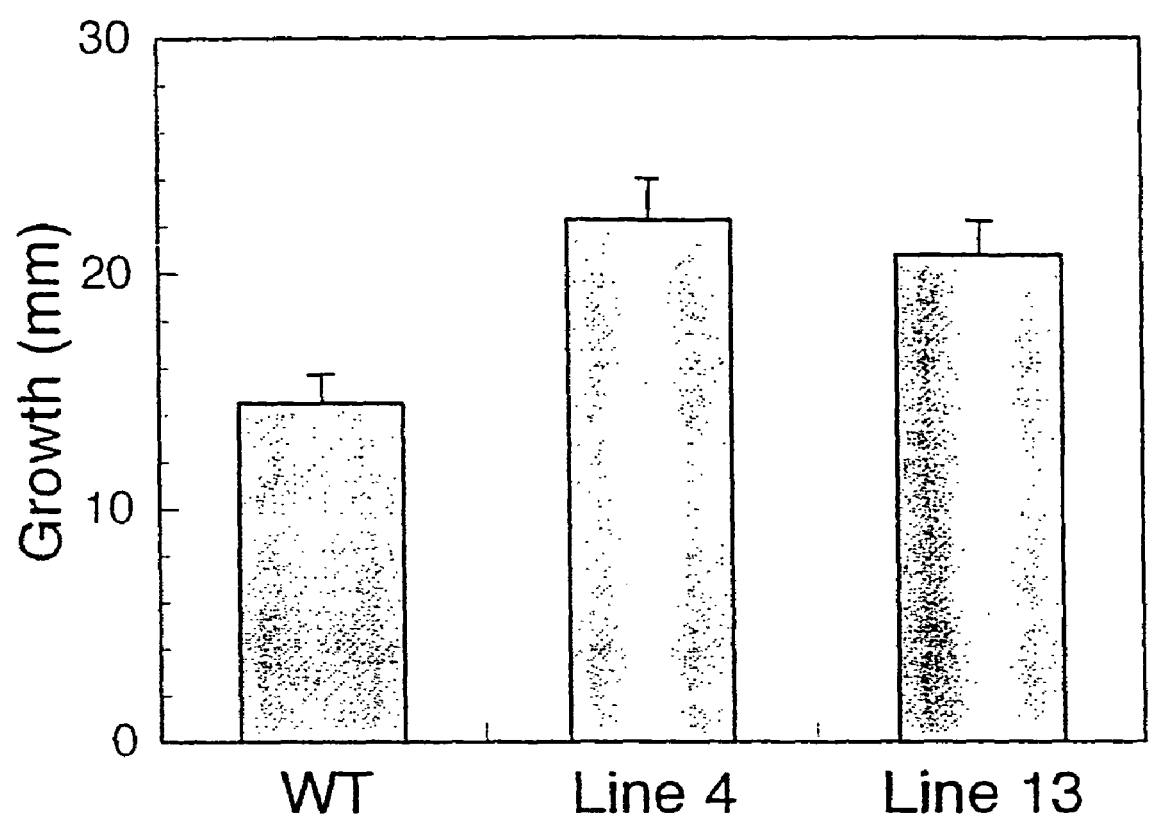
FIG. 6 shows that there is enhanced diameter growth of transgenic hybrid aspen also in the second growth season. The cumulative diameter growth of control (WT) and line 4 and 13 was determined under a period of 2.5 months, beginning after breaking of dormancy.

The observed increase in height growth (FIG. 3) in the transgenic GA 20-oxidase *Populus* trees was apparently not a consequence of increased cell elongation, as no significant changes in cell lengths were found (FIG. 5A). However, observed differences in numbers of cells per fully elongated internode clearly indicate that elevated GA levels affect cell divisions in stem tissue (FIG. 5). This is an interesting aspect of the present invention, which opens up many possibilities of influencing the production of fibrous raw material and biomass for different purposes.

Although GAs have been found to affect cell elongation, it is also known GAs can induce mitotic activity in the subapical region of the stem. It must be emphasised, however, that although samples were taken for cell length measurements from the same position for both control and transgenic plants (as defined by the number of internodes from the apex), it can not be ruled out that the cells in the transgenic plants could have been at an earlier developmental stage than in wild type plants, and they could still have been elongating. It has also been suggested that the action of GAs in meristematic tissues extends the elongation zone of the organ being formed.

TABLE 1

Concentration (ng g$^{-1}$ fresh weight) of GAs in stem/leaf tissue from internodes 7 and 8 (see text for details) of transgenic hybrid aspen expressing the AtGA20ox1 gene. Means of three independent measurements.

| Genotype | $GA_{12}$ | $GA_{53}$ | $GA_{19}$ | $GA_9$ | $GA_{20}$ | $GA_4$ | $GA_1$ | $GA_{34}$ | $GA_8$ |
|---|---|---|---|---|---|---|---|---|---|
| Control | 5.78/1.15 | 3.22/0.41 | 3.15/1.21 | n.d./n.d. | 0.45/0.43 | 0.84/0.88 | 0.63/0.63 | 1.63/1.23 | 15.0/9.4 |
| Line 1 | 1.16/0.79 | 0.29/0.28 | 0.85/0.55 | 3.20/0.64 | 5.36/1.44 | 9.71/4.03 | 20.2/1.29 | 5.00/3.78 | 58.6/40.7 |
| Line 2 | 3.02/0.90 | 1.04/1.25 | 3.55/0.59 | 4.34/1.24 | 3.69/2.84 | 9.04/6.60 | 10.2/2.47 | 8.37/5.94 | 77.4/43.8 |
| Line 4 | 1.06/0.71 | 0.27/0.24 | 0.81/0.63 | 5.23/0.86 | 5.03/2.84 | 11.3/4.76 | 11.7/1.58 | 7.84/4.78 | 53.2/52.9 |
| Line 7 | 1.00/0.73 | 0.29/0.28 | 1.21/0.60 | 5.38/0.78 | 4.74/2.36 | 20.7/6.29 | 14.0/1.35 | 6.03/4.69 | 68.4/32.7 |
| Line 9 | 2.49/0.73 | 0.62/0.26 | 1.19/0.56 | 5.67/0.73 | 6.00/2.16 | 9.70/5.13 | 5.42/2.35 | 10.46/4.85 | 70.0/49.6 |
| Line 11 | 1.67/0.62 | 0.57/0.28 | 2.04/0.60 | 4.31/1.42 | 5.77/3.31 | 10.7/5.30 | 14.2/1.81 | 9.43/4.28 | 72.6/42.6 |
| Line 13 | 0.91/0.78 | 0.26/0.25 | 0.90/0.64 | 6.58/0.64 | 16.4/3.45 | 19.8/6.46 | 29.3/3.22 | 7.98/3.85 | 75.9/55.1 |
| Line 14 | 1.26/0.64 | 0.27/0.25 | 0.62/0.55 | 3.2/0.41 | 4.01/1.48 | 6.99/2.36 | 11.6/1.38 | 5.52/4.69 | 78.6/37.5 |
| Line 15 | 1.82/0.60 | — | 5.57/0.74 | — | 2.53/2.57 | 3.14/2.58 | 2.58/1.62 | 7.53/5.02 | 57.6/48.2 | n.d. = not detectable.

Figure 4:
FIG. 4 is a photograph showing control and transgenic (line 11) plants after 12 weeks in the growth chamber.

Studies involving the application of plant hormones have shown that GAs can increase cambial activity in trees, especially in conjunction with IAA. Here, the engineered increase in GA levels resulted in faster stem diameter growth (FIG. 4). An effect of elevated GA levels on secondary growth was also observed with the increase in number of xylem fibre cells and xylem fibre length (FIG. 5C, D). The length increase measured in the experiments is about 8% which must be held to be a significant increase, having consequences for the fibre properties and thus the potential uses for the fibrous raw material.

This is consistent with application studies with both GAs and inhibitors of GA biosynthesis. In *Populus*, fibre and vessel lengths increase in the transition zone between juvenile and mature wood. Therefore, the time it takes for a cell to mature within the cambial region, i.e. the time spent in the different differentiation zones, will ultimately determine its size and cell wall thickness. If the action of GAs like $GA_1$ and/or $GA_4$ extends this transition time, this would explain both the increased fibre length in the mature parts of the transgenic plant and the lack of differences in xylem fibre length between transgenic and control plants in young stem tissue.

The increase in leaf size in the transgenic plants was a result of an increase in both radial and longitudinal elongation (Table 2). At earlier stages the longitudinal growth was more pronounced, resulting in long, narrow leaves. However, at later stages the leaf morphology became similar to control plants with a similar leaf width to length ratio. It has been shown that GAs promote leaf elongation e.g. in garden pea. The very long and narrow leaves observed in constitutive GA signal mutants, like sln mutants of barley and spy mutants of *Arabidopsis*, also indicate that GAs promote leaf elongation. However, little is still known on the more specific regulatory roles of GAs in leaf development. In *Arabidopsis*, leaf blade expansion is regulated by at least two independent and polarised processes: length and width development, with ROTUNDIFOLIA and ANGUSTIFOLIA genes playing specific roles. It is not known whether GAs modulate the cellular responses to these genes. However, it is noteworthy that leaf phenotypes in the transgenic GA 20-oxidase aspen change during development, suggesting that the two developmentally separate processes of leaf length and width growth are both affected by GAs, but at different stages.

TABLE 2

Morphological characterisation of wild type and transgenic hybrid aspen expressing the AtGA20oxl gene. The numbers of plants used for the measurements were 10, 5 and 6 for the control, line 2, and line 11, respectively. In the biomass determination the numbers of plants sampled were 7, 2, 3 and 23 for the control, line 2, line 11, and all sampled transgenics, pooled, respectively.
For all statistical analyses ANOVA was used to compare the plants with respect to genotype.

| | Genotype | | |
|---|---|---|---|
| | Control | Line 2 | Line 11 |
| Internode length (cm ± SE) | 2.19 ± 0.05 | 3.06 ± 0.09* | 3.07 ± 0.09* |
| | Leaf length and width (cm ± SE) | | |
| Leaf length 10 | 8.34 ± 0.36 | 9.52 ± 0.38** | 9.17 ± 0.28 |
| Leaf width 10 | 7.25 ± 0.41 | 6.28 ± 0.20 | 5.85 ± 0.24** |
| Leaf length 14 | 9.52 ± 0.45 | 11.18 ± 0.60** | 10.78 ± 0.41 |
| Leaf width 14 | 8.00 ± 0.38 | 8.35 ± 0.39 | 8.52 ± 0.25 |
| Leaf length 18 | 9.90 ± 0.79 | 11.06 ± 1.00 | 11.68 ± 0.56 |
| Leaf width 18 | 7.48 ± 0.64 | 8.80 ± 0.47 | 8.88 ± 0.43 |
| Leaf length 20 | 7.75 ± 0.34 | 11.94 ± 0.44* | 11.25 ± 0.48* |
| Leaf width 20 | 6.07 ± 0.46 | 9.44 ± 0.41* | 8.85 ± 0.41* |
| Dry Weight Biomass (g) | Control | Line 2, 11 | Transgenes |
| Leaf | 5.45 ± 0.51 | 6.38 ± 0.58 | 6.14 ± 0.28 |
| Stem | 4.58 ± 0.43 | 10.42 ± 1.01* | 10.34 ± 0.49* |
| Root | 43.05 ± 4.71 | 38.36 ± 2.63 | 37.81 ± 2.06 |
| | Fresh Weight Biomass (g) | | |
| Leaf | 17.10 ± 1.63 | 23.10 ± 2.01** | 22.05 ± 0.91** |
| Stem | 12.04 ± 1.19 | 31.39 ± 2.88* | 30.58 ± 1.28* |

Statistically significant difference are indicated at the 1%* and 5%** probability levels (Fisher's PLSD).

Biomass measurements in transgenic and wild type plants revealed that an increase in GA 20-oxidase activity leads to a general increase in growth. This effect was especially pronounced in the stem, indicating that GAs have a strong effect on stem growth. Spraying experiments with various GAs have previously shown that these hormones tend to increase shoot biomass in *Populus* at the expense of root growth. Reductions in root formation due to increased GA levels in roots have earlier been shown in trees. In this study, poor root initiation was the major problem for survival of the transgenic GA 20-oxidase plants in tissue culture and when planting in soil. At later developmental stages, root development was still affected, but to a lesser degree (Table 2). It has also been shown that the effect of GAs on rooting varies with the stage of root development.

In conclusion, the present inventors have here demonstrated the important role of GA 20-oxidase activity in GA-controlled growth in *Populus*. It is surprising that the effects, hitherto only achieved, and in some cases only partially achieved, by external application, e.g. spraying, can be achieved by endogenous expression. It is also surprising that the inventive method can be applied to a higher species, here represented by hybrid aspen. *Populus tremula*×*P. tremuloides*. One important advantage of the present invention is thus that it may make it possible to reduce or eliminate the use of growth influencing chemicals in forestry.

The present invention opens up ways to genetically engineer trees to grow faster and produce more biomass simply by increasing endogenous GA levels. Interestingly, fibre lengths also increase as a result of the over-expression of the GAs. These results have both practical implications (assisting in the production of modified trees of interest to the pulp. paper and forest industries), and scientific importance, by allowing previously impossible studies on the mechanisms whereby GAs control growth and development in trees.

EXAMPLES

Example 1

Experimental Protocol:

Plant Vector Construction

The *Arabidopsis* GA 20-oxidase cDNA construct cloned in bluescript pAt2301 [Phillips. A. L. et al. Isolation and expression of three gibberellin 20-oxidase cDNA clones from *Arabidopsis*. *Plant Physiol.* 108. 1049-1057 (1995)], recently renamed AtGA20ox1 [Coles. J. P. et al. Modification of gibberellin production and plant development in *Arabidopsis* by sense and antisense expression of gibberellin 20-oxidase genes. *Plant J.* 17. 547-556 (1999)] was obtained as a gift from P. Hedden.

An upstream ATG sequence, preceding the translational start of the GA 20-oxidase enzyme, was removed by in vitro mutagenesis. A forward primer matching the 5'-end of the GA 20 oxidase gene, but lacking the extra ATG and carrying a Bam HI and Xba I site, and a reverse primer spanning an internal Hind III site in the GA 20 oxidase gene, were used in a PCR reaction. Using AtGA20ox1 as a template, a PCR product was obtained and subcloned into the pOK12 vector, generating plasmid pOK12.GA20ox5'. An entire GA 20-oxidase cDNA lacking the extra ATG was then re-constituted, by digesting AtGA20ox1, isolating a fragment containing the 3'-end of the GA 20-oxidase gene, and ligation of this fragment into pOK12.GA20ox5', giving plasmid pOK12/AtGA20ox1. The GA 20-oxidase cDNA was then isolated from pOK12/AtGA20ox1, by digestion with Bam HI, and ligated in sense orientation into the Bam HI site of the binary vector pPCV702.kana [Walden, R., Koncz, C. & Schell, J. Methods Mol. Cell. Biol. 1. 175-194 (1990). The use of gene vectors in plant molecular biology, *Methods Mol. Cell Biol.* 1, 175-194 (1990)], subjecting it to the control of the CaMV 35S promoter.

Plant Transformation and Growth Conditions

Hybrid aspen *Populus tremula* L.×*P. tremuloides* Michx. clone T89 was transformed and regenerated essentially as previously described [Nilsson, O. et al. Spatial pattern of cauliflower mosaic virus 35S promoter-luceferase expression in transgenic hybrid aspen trees monitored by enzymatic assay and non-destructive imaging. *Transgenic Research* 1. 209-220 (1992)]. Out of 14 independent lines. 10 were selected and multiplied by in vitro shoot culture on half-strength MS-medium containing minerals and vitamins [Murashige. T. & Skoog. F. A revised medium for rapid growth and bio-assay with tobacco tissue cultures. *Physiologia Plantarum* 15. 473-479 (1962)].

Following root initiation, the plants were dipped in Weibufix rooting powder (Svalof Weibull A B. Hammenhög. Sweden), and potted in a fertilised peat: perlite mixture (5:1) and kept in a growth chamber at 18° C. under a photoperiod of 18 h and a relative humidity of 90%. The photon flux density of the main light period (10 h) was 175 µmol m$^{-2}$ s$^{-1}$ at 400-750 nm (Osram Power Staw HQI-TS 400 W/D lamps. Osram. Germany) and daylength extensions were given using low-intensity light (20 µmol$^{-2}$ s$^{-1}$). Plants were watered daily, and repotted and fertilised with a complete nutrient solution (SuperbaS. Supra Hydro A B. Landskrona. Sweden) when needed. After 108 days some plants were transferred to short photoperiod conditions (10 h) to induce growth cessation. These plants were then cold acclimated and kept dormant at 8° C. for 4 weeks, at which point samples were taken for fibre length measurements.

Growth Measurements and Sampling

At seven weeks of age, the plants were marked at an actively growing internode at about the same position in all plants. This was used as a reference point for diameter growth measurements and for counting the internodes. The diameter, height and number of internodes of the plants were measured every 3$^{rd}$ to 4$^{th}$ day. The number of internodes was counted from the top to the reference point: the first internode being defined as the one below the uppermost leaf at least 1 cm long. Plants grown under long days were harvested after 100 days, using seven control plants and 25 plants representing nine transgenic individual lines (line 6 was excluded). Internodes 7 and 8, with the upper leaves included, were sampled for GA analysis and leaves from nodes 9 and 10 for northern analysis. All tissues were frozen in liquid N$_2$ immediately after sampling. For anatomical studies, the length of internodes 15 and 16 were measured, then excised and fixed immediately in FAA. All parts remaining after sampling were separated into leaf, stem and root fractions and used for fresh weight biomass determinations. Dry weight was determined after drying the samples at 55° C. for 5 days. Dormant plants consisting of three controls and five transgenes (representing lines 2. 11 and 14) were sampled at internodes 1, 10 and 20, counted from the reference point. These samples were used for maceration and subsequent fibre length measurements.

Anatomical Characterisation

Following conventional chemical fixation samples were embedded in L R White [Regan, S., Bourquin, V., Tuominen, H. & Sundberg, B. Accurate and high resolution in situ hybridization analysis of gene expression in secondary stem tissues, *Plant J.* 19, 363-369 (1999)]. Longitudinal sections for cell counts (internode 15 and 16) and transverse sections for fibre count (internode 30), 2 µm thick, were obtained and stained with toluidine blue. Numbers of epidermal and pith cells in 1 mm of the longitudinal sections were determined for 3 sections per internode. Cell length and number of cells per internode were calculated as the averages found in internodes 15 and 16. The number of xylem fibres was counted in three separate radial files (from pith to cambium) per individual and the average for each genotype (line 4, 11, 13 and control) was calculated.

Fibre Length Measurements

For fibre length determination, trimmed pieces of outer xylem from the selected internodes were prepared. The samples were macerated by boiling in a solution of 10% hydrogen peroxide and 50% glacial acetic acid for 4-6 h. When totally bleached, they were rinsed with distilled water three times, neutralised with sodium carbonate and washed again in water. Finally, the fibres were separated from each other by shaking in water and measured using a fibre analyser (KAJAANI FiberLab, Valmet Automation Kajaani Ltd. Kajaani, Finland). On average, the lengths of 30 800 fibres per sample were measured.

Northern Analysis

Total RNA was extracted from leaves using a chloroform and hexadecyltrimethylamonium bromide based method according to Chang et al. [Chang, S., Puryear, J. & Carney, J. A simple and efficient method for isolating RNA from pine trees. *Plant Mol. Biol. Rep.* 11. 113-116 (1993)]. About 18 µg of total RNA per sample was separated in a formaldehyde agarose gel according to Sambrook et al. [Sambrook, J., Fritsch, E. & Maniatis, T. *Molecular Cloning: A Laboratory Manual*, Cold Spring Harbor Laboratory Press, New York, 1989], and blotted on to a nylon Hybond-N membrane (Amersham, Little Chalfont, UK) according to the manufacturer's protocol. A Bam HI/Xho I fragment recovered from pOK12/AtGA20ox1 and an ubiquitin-like Expressed Sequence Tag (EST A046p57) obtained in the *Populus* sequencing project [Sterky, F. et al. Gene discovery in the wood-forming tissues of poplar: Analysis of 5.692 expressed sequence tags. *Proc. Natl. Acad. Sci. USA* 95. 13330-13335 (1998)] were used as probes for analysis of ectopic AtGA20ox1 and reference gene expression, respectively. Hybridisation was performed in Church buffer [Church, G. M. & Gilbert, W., Genomic sequencing, *Proc. Natl. Acad. Sci. USA* 81. 1991-1995 (1984)] at 65° C. overnight. The membrane was washed at 65° C. two times three minutes in each of solution: 2×SSPE. 0.1% SDS; 1×SSPE. 0.1% SDS; 0.5×SSPE. 0.1% SDS and 0.1× SSPE. 0.1% SDS. To visualise the expression patterns, the membrane was exposed to a phosphor imager (Molecular Imager GS-525, Bio-Rad Laboratories, Hercules, Calif., USA) overnight.

Quantification of Gibberellins

Samples of 200-300 mg were ground in liquid nitrogen to a homogenous powder, and GAs were analysed as earlier described by Peng et al. [Peng, J. R., Richards, D. E., Moritz, T., CanoDelgado, A. & Harberd, N. P., Extragenic suppressors of the *Arabidopsis* gai mutation alter the dose-response relationship of diverse gibberellin responses, *Plant Physiol.* 119, 1199-1207 (1999)] with a few modifications. Volumes of the solvents used for extraction and partitioning, and that of the anion-exchange column, were reduced. Furthermore, the samples were methylated prior to the HPLC step, and finally they were analysed by GC/MS-selected reaction monitoring (SRM) using a JEOL SX/SX102A four sector mass spectrometer (JEOL, Tokyo, Japan). [$^2$H$_2$]-GAs were used as internal standards.

Results

Generation of Transgenic GA 20-Oxidase Hybrid Aspen

Figure 2:
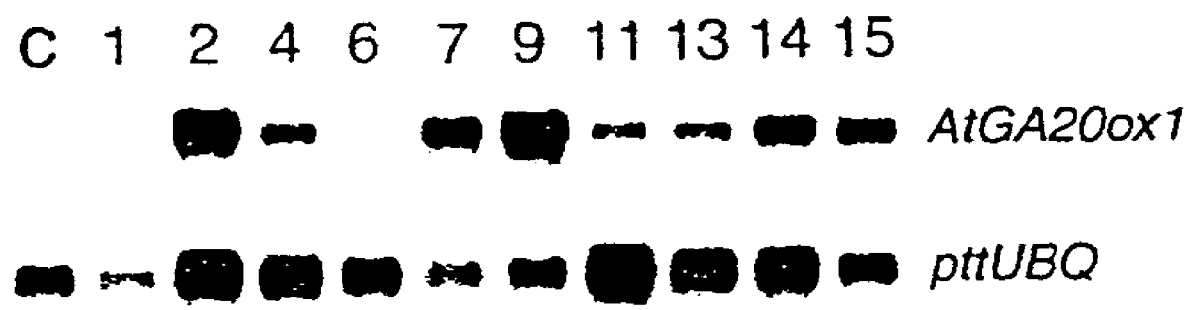
FIG. 2 shows a Northern analysis of ten GA 20-oxidase over-expressing lines (numbers 1 to 15) and the non-transformed control (C). 18 µg of total RNA was loaded from each sample, and probed with a labelled fragment isolated from *Arabidopsis* gibberellin 20-oxidase (AtGA20ox1) cDNA or from an endogenous ubiquitin (UBQ) EST sequence (pt-tUBQ).

Out of 14 independently transformed lines, 10 were regenerated and selected for further analysis. Southern analysis showed that all the selected transgenic lines have one to three copies of the AtGA20ox1 gene inserted into their genomes, except for line 6, which has at least 4 copies (data not shown). Northern analysis of RNA isolated from leaf tissue showed that the strongest expression of the AtGA20ox1 gene was in lines 2, 7, 9, 14 and 15. Expression was slightly lower in lines 1, 4, 11 and 13, while expression was almost undetectable in line 6 (FIG. 2). In general, the transgenic lines showed poorer rooting than the control plants, both under tissue culture conditions and when potted in soil. When potted, for example, 100% of the control plants survived, compared to only 32% of the transgenic plants.

GA Levels

GA content was determined both in leaves and internodes of actively growing tissue. Transgenic plants showed high levels of the 13-hydroxylated $C_{19}$-GAs ($GA_{20}$, $GA_1$ and $GA_8$) and the non 13-hydroxylated $C_{19}$-GAs ($GA_9$, $GA_4$ and $GA_{34}$) in both stem and leaves (Table 1). The increase over wild type levels was more pronounced in stem tissue than in leaf tissue. The levels of the biologically active $GA_1$ and $GA_4$ in stem tissues of lines 7 were 22- and 24-fold higher, respectively, than in the control. Furthermore, all transgenic lines showed lower levels of the substrates for the GA 20-oxidase. For example $GA_{12}$ and $GA_{53}$ levels in stem tissues of line 7 were 17% and 9% of the contents in the control, respectively.

Shoot Growth and Morphology

All transgenic lines showed faster than wild type height and diameter growth (FIG. 3), giving the trees a characteristic phenotype (FIG. 4). Although levels of GA 20-oxidase mRNA varied between the transgenic lines (FIG. 2) there were no strict correlation between expression levels and growth. A detailed study of two of the transgenic lines (Table 2) revealed that the difference in height growth was primarily due to differences in internode lengths. No statistically significant differences in the number of nodes (leaves) were observed (data not shown). However, leaf development was different in the transgenic lines. Young expanding leaves had a different morphology and a higher leaf length to width ratio than leaves of control plants (Table 2). After node 14, i.e. in the fully expanded leaves, there was no significant difference in this morphological ratio, but there was still a clear difference in leaf size between control and transgenic plants. The transgenics had longer and broader leaves and, consequently, higher mean leaf fresh weights (Table 2). Furthermore, the petioles were longer in the transgenic lines than in the control (data not shown).

There was a significant difference in shoot biomass between transgenic and control plants when measured either on a fresh or dry weight basis (Table 2). The transgenic plants had 64% higher shoot dry weight, on average, than the control plants. This difference was especially pronounced in the stem, where the transgenic plants had 126% higher dry weight than the control plants. Consequently, the transgenic plants also had an altered root:shoot weight ratio, of only about 2:1 compared to 4:1 for control plants. Although the initial rooting capacity was lower in the transgenic lines, there was no significant difference in root dry weight between transgenic and control plants (Table 2).

Cell Length and Cell Numbers in Transgenic Plants

Expression of the AtGA20ox1 gene did not affect the lengths of epidermal and pith cells in presumably fully elongated internodes (see Experimental Protocol for definition) in the actively growing transgenic lines (FIG. 5A). However, epidermal and pith cell numbers in these elongated internodes were approximately 55% higher than in the wild type control (FIG. 5B).

Cambial activity was also determined by counting numbers of xylem fibre cells in transverse sections (FIG. 5C). The transgenic lines show 71% increase in number of xylem fibre cells compared to the control plants. Xylem fibres were sampled at three different positions in dormant plants and their lengths were measured. No differences in fibre length from different heights in the trees were detected (data not shown), but the xylem fibres were approximately 8% longer in the transgenic lines than in the control plants (FIG. 5C). Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

Example 2

The technique of Example I may be applied to any available polypeptide that exhibits GA 20-oxidase activity. GA 20-oxidases have been expressed in non-woody plants and have been shown to result in increased gibberellin levels in such plants, which demonstrate that the GA 20-oxidases will be function regardless of the source of the enzyme and regardless of the woody plant in which the enzyme is expressed. By way of example, the *Arabidopsis* GA 20-oxidase gene was overexpressed in *Arabidopsis* (Coles et al. 1999; cited in the present patent application). In addition, GA 20-oxidases have also been overexpressed in other species and resulted in increased gibberellin levels, e.g. tobacco (*Arabidopsis* GA20ox: Biemelt et al 2004 Plant Phys: 135: 254-265; Citrus GA20ox: Vidal et al. 2001 Physiol. Plant. 112: 251-260) and potato (potato GA20ox: Carrera et al. Plant J. 22: 247-256).

As shown in the sequence alignment in Table 3 (containing SEQ ID NOs: 1-70), many polypeptides exhibiting GA 20-oxidase are available in the art. Additional GA 20-oxidase polypeptides may be readily identified by the three conserved motifs within the polypeptides as shown on Table 3. Furthermore, the large number of polypeptides provide abundant guidance for generation of derivative polypeptides that will have the desired GA 20-oxidase activity. Finally, polypeptides can readily be expressed and screened for GA 20-oxidase activity using routine methods of molecular biology and enzymology, so one of skill in the art will be able to generate and screen polypeptides having GA 20-oxidase activity. This Example 2 sets out a representative protocol for generating transgenic plants expressing a GA 20-oxidase.

Experimental Protocol:

Plant Vector Construction

The a GA 20-oxidase cDNA construct encoding any one of the polypeptides selected from Table 3 is cloned into an expression vector such as the binary vector pPCV702.kana such that the GA 20-oxidaes polypeptide is operably linked to a promoter such as the CaMV 35S promoter.

Plant Transformation and Growth Conditions

The expression vector is then transformed into the desired woody plant using standard techniques available in the art. By way of example, a hybrid aspen *Populus tremula L.×P. tremuloides* Michx. clone is transformed and regenerated essentially as previously described [Nilsson, O. et al. Spatial pattern of cauliflower mosaic virus 35S promoter-luceferase expression in transgenic hybrid aspen trees monitored by enzymatic assay and non-destructive imaging. *Transgenic Research* 1. 209-220 (1992)]. Out of the independent lines, a reasonable number are selected and multiplied by in vitro shoot culture on half-strength MS-medium containing minerals and vitamins [Murashige. T. & Skoog. F. A revised medium for rapid growth and bio-assay with tobacco tissue cultures. *Physiologia Plantarum* 15. 473-479 (1962)].

Following root initiation, the plants are dipped in Weibufix rooting powder (Svalöf Weibull A B. Hammenhög. Sweden), and potted in a fertilised peat: perlite mixture (5:1) and kept in a growth chamber at 18° C. under a photoperiod of 18 h and a relative humidity of 90%. The photon flux density of the main light period (10 h) is 175 µmol m$^{-2}$ s$^{-1}$ at 400-750 nm (Osram Power Staw HQI-TS 400 W/D lamps. Osram. Germany) and daylength extensions are given using low-intensity light (20 µmol$^{-2}$ s$^{-1}$). Plants were watered daily, and repotted and fertilised with a complete nutrient solution (SuperbaS. Supra Hydro A B. Landskrona. Sweden) when needed. After 108 days some plants are transferred to short photoperiod conditions (10 h) to induce growth cessation. These plants are then cold acclimated and kept dormant at 8° C. for 4 weeks, at which point samples are taken for fibre length measurements.

Growth Measurements and Sampling

At seven weeks of age, the plants are marked at an actively growing internode at about the same position in all plants. This is used as a reference point for diameter growth measurements and for counting the internodes. The diameter, height and number of internodes of the plants are measured every 3$^{rd}$ to 4$^{th}$ day. The number of internodes is counted from the top to the reference point: the first internode being defined as the one below the uppermost leaf at least 1 cm long. Plants grown under long days are harvested after 100 days, using seven control plants and 25 plants representing the reasonable number of transgenic individual lines. Internodes 7 and 8, with the upper leaves included, are sampled for GA analysis and leaves from nodes 9 and 10 for northern analysis. All tissues are frozen in liquid N$_2$ immediately after sampling. For anatomical studies, the length of internodes 15 and 16 were measured, then excised and fixed immediately in FAA. All parts remaining after sampling are separated into leaf, stem and root fractions and used for fresh weight biomass determinations. Dry weight is determined after drying the samples at 55° C. for 5 days. Dormant plants consisting of three controls and five transgenes are sampled at internodes 1, 10 and 20, counted from the reference point. These samples are used for maceration and subsequent fibre length measurements.

Anatomical Characterisation

Following conventional chemical fixation samples are embedded in L R White [Regan, S., Bourquin, V., Tuominen, H. & Sundberg, B. Accurate and high resolution in situ hybridization analysis of gene expression in secondary stem tissues, *Plant J.* 19, 363-369 (1999)]. Longitudinal sections for cell counts (internode 15 and 16) and transverse sections for fibre count (internode 30), 2 µm thick, are obtained and stained with toluidine blue. Numbers of epidermal and pith cells in 1 mm of the longitudinal sections are determined for 3 sections per internode. Cell length and number of cells per internode are calculated as the averages found in internodes 15 and 16. The number of xylem fibres are counted in three separate radial files (from pith to cambium) per individual and the average for each genotype are calculated.

Fibre Length Measurements

For fibre length determination, trimmed pieces of outer xylem from the selected internodes are prepared. The samples are macerated by boiling in a solution of 10% hydrogen peroxide and 50% glacial acetic acid for 4-6 h. When totally bleached, they are rinsed with distilled water three times, neutralised with sodium carbonate and washed again in water. Finally, the fibres are separated from each other by shaking in water and measured using a fibre analyser (KAJAANI FiberLab, Valmet Automation Kajaani Ltd. Kajaani, Finland). On average, the lengths of 30-800 fibres per sample are measured.

Northern Analysis

Total RNA is extracted from leaves using a chloroform and hexadecyltrimethylamonium bromide based method according to Chang et al. [Chang, S., Puryear, J. & Cairney, J. A simple and efficient method for isolating RNA from pine trees. *Plant Mol. Biol. Rep.* 11. 113-116 (1993)]. About 18 µg of total RNA per sample is separated in a formaldehyde agarose gel according to Sambrook et al. [Sambrook, J., Fritsch, E. & Maniatis, T. *Molecular Cloning: A Laboratory Manual*, Cold Spring Harbor Laboratory Press, New York, 1989], and blotted on to a nylon Hybond-N membrane (Amersham, Little Chalfont, UK) according to the manufacturer's protocol. An appropriate fragment recovered from expression vector and an ubiquitin-like Expressed Sequence Tag (EST A046p57) obtained in the *Populus* sequencing project [Sterky, F. et al. Gene discovery in the wood-forming tissues of poplar: Analysis of 5.692 expressed sequence tags. *Proc. Natl. Acad. Sci. USA* 95. 13330-13335 (1998)] are used as probes for analysis of ectopic GA 20-oxidase polypeptide and reference gene expression, respectively. Hybridisation is performed in Church buffer [Church, G. M. & Gilbert, W., Genomic sequencing, *Proc. Natl. Acad. Sci. USA* 81. 1991-1995 (1984)] at 65° C. overnight. The membrane is washed at 65° C., two times three minutes in each of solution: 2×SSPE. 0.1% SDS; 1×SSPE. 0.1% SDS; 0.5×SSPE. 0.1% SDS and 0.1×SSPE. 0.1% SDS. To visualise the expression patterns, the membrane is exposed to a phosphor imager (Molecular Imager GS-525, Bio-Rad Laboratories, Hercules, Calif., USA) overnight.

Quantification of Gibberellins

Samples of 200-300 mg are ground in liquid nitrogen to a homogenous powder, and GAs are analysed as earlier described by Peng et al. [Peng, J. R., Richards, D. E., Moritz, T., CanoDelgado, A. & Harberd, N. P., Extragenic suppressors of the *Arabidopsis* gai mutation alter the dose-response relationship of diverse gibberellin responses, *Plant Physiol.* 119, 1199-1207 (1999)] with a few modifications. Volumes of the solvents used for extraction and partitioning, and that of the anion-exchange column, are reduced. Furthermore, the samples are methylated prior to the HPLC step, and finally they are analysed by GC/MS-selected reaction monitoring (SRM) using a JEOL SX/SX102A four sector mass spectrometer (JEOL, Tokyo, Japan). [$^2$H$_2$]-GAs are used as internal standards.

Results

The results obtained for introduction of any of the polypeptides selected from Table 3 into the desired woody plant will be similar the results of Example 1.

TABLE 3

Alignment of all protein sequences identified as plant GA20oxidases in one database. ▓▓▓▓▓▓▓▓▓▓ conserved sequences believed to be involved in substrate binding (binding to GA). Marked in light grey: conserved sequences believed to be involved in 2-oxoglutarate binding (co-substrate). Sequence fairly conserved within enzyme family 2-oxoglutarate dependent dixoygenases. ▓▓▓▓▓▓▓▓▓▓ $Fe^{2+}$-binding motif, conserved in enzyme family 2-oxoglutarate dependent dioxygenases.

```
                                      10        20        30        40        50        60        70
                                ....|....|....|....|....|....|....|....|....|....|....|....|....|....|
ABB00359.1   Fragaria x an      MAVGCMKTLS--------------------HHKEDDQKPLVFDASLLRYETD-IPKQFIWPDDEKPCPN--TRE
BAB20975.1   Malus x domes      MAVECMIKPSSLQTM----TQPPSPKTQQTQQHKEDDQKPLVFDASVFRYQTE-IPSQFIWPDHEKPCKN--TRE
AAB64345.1   Cucurbita max      MALNGKVATESAPSN-------------------LNEEMKGEYRPPFGGSDESKVPEDFIWSEKFEASEL--LPV
CAA51744.1   Cucurbita max      MALNGKVATESAPSN-------------------LNEEMKGEYRPPFGGSDESKVPEDFIWSEKFEASEL--LPV
CAC83626.1   Cucurbita max      ------------MHV----VTSTP-------EAR-HDGAPLVFDASVLRHQHN-IPKQFIWPDEEKPAAT--CPE
CAA70329.1   Marah macroca      MAITCMMATESSP--------------------AEEVKREHQVAFGGAGESSVPENFIWPDEFKATAD--APE
AAD42693.1   Citrullus lan      MAMKCMMSTGES---------------------KEMKSKLHRVEFGCSEESMVPENFVWPDEFKAKDG--APE
CAA17539.1   Arabidopsis t      ---------------------------------MDPPFNEIYNNLLYNQITKKDNDVSEIPFSFSVTAVVEE NP_176294.1  Arabidopsis       --MECIIKLPQRF------NKNKSK-----------KNPLRIFDSTVLNHQPDHIPQEFVWPDHEKPSKN--VPI
NP_175509.1  Arabidopsis       ---------------------------------MASQPPPFKTNFCSIFGSSFP---NSTSES-NTNTSTIQTSG
Q39110|GAOX1 Arabidopsis       MAVSFVTTSPEE-------EDKPKLG------LGNIQT-PLIFNPSMLNLQAN-IPNQFIWPDDEKPSIN--VLE
Q39112|GAOX3 Arabidopsis       MATECIATVPQIF------SENKTK-----------EDSS-IFDAKLLNQHSHHIPQQFVWPDHEKPSTD--VQP
Q39111|GAOX2 Arabidopsis       MAILCTTTSPEAK------EHEPKQD------LEKDQTSPLIFNPSLLNLQSQ-IPNQFIWPDEEKPSID--IPE
AAY98356.1   Sesbania rost      --MDSGLCLVSG-------LNHKD-------------VQTRFFGPSWLQMQSH-VPMNFIWPK-ECLVNA--HEE
AAC49721.1   Pisum sativum      MAIECITSSAKLMT-----QKSDK-------NEN-EESSKLVFDASFLKNQLN-LPKQFIWPDDEKPCMN--VPE
CAA62846.1   Pisum sativum      MAIECITSSAKLMT-----QKSDK-------NEN-EESSKLVFDASFLKNQLN-LPKRFIWPDDEKPCMN--VPE
AAB67838.1   Pisum sativum      -MKVLCSSMLFAP------PNANES--------FMNEQKQCLDNTSSLPLQITN-IPSEFIWPDHEKPCLT--PPK
CAD21845.1   Fagus sylvati      ----------------------------------------------------------------------------

CAD21846.1   Fagus sylvati      MAIDCITNITSMP-------HPPK-----EEH-KDHQKQLVFDASVLRHQTN-IPQQFIWPDEEKPRAN--APE
AAC49756.1   Phaseolus vul      MAIDCMTNIQTMSQP----QKHHH-------QDNKEDEAPLVFDASLLRHQLN-LPKQFIWPDDEKPCMN--VPE
AAC49758.1   Phaseolus vul      -MLIPHPSMLLAS------QNT------------NMEPQQINLQAPTPNQ-SN-IPSEFVWPDNEKPCLE--PPK
AAC49757.1   Phaseolus vul      MAIDMHP--IPIMP-----QPSNQ-------EIKEQDQHPLVFDASLLRHQLH-IPSQFVWPDEEKACLN--EPE
AAW80969.1   Gossypium hir      -MVHCLPKVSVIQDKPMLPPTAAV--------AKNKHR-PLAFDASILG--SE-ISSQFIWPDDDKPCLD--APE
AAT28326.1   Gossypium hir      -MVHCLPKVFVIQDKMLPSTAAV--------AKDEHR-PLAFDASILGSESN-IPSQFIWPDDEKPCLD--APA
ABA01489.1   Gossypium hir      -MVHCLPKVFVIQDKPLSTAAV---------AKDEYWPPLAFDASILGSESN-IPSQFIWPDDEKPCLD--TPE
BAD90753.1   Ipomoea nil        MAIECMIPTPTPN-------HERQE-------IENKPAAAVVFDSPVLRHESN-IPTEFLWPDHEKPGPY--AARE
BAD90752.1   Ipomoea nil        MAIECVTTTPTRS-------DDPK-----------AAAVVFDSSVLRHETN-IPTEFVWPEHEKPGSY--AAPE
BAA32156.1   Nicotiana tab      MAIDCMITNVNSPMLRILEDDKKP--------------LIFDASQMKREYN-IPTQFIWPDDEKPRAV--ARE AAT39975.1   Solanum demis      MAIDCMITRNNNMTS----KEGQEY-------DIIKTNKSLSFDASLMKNESN-IPSQFIWPDHEKPNCASVTRE
CAB82616.1   Solanum dulca      MAIDCMITNGKSPML----DEKKT---------------LIFDASHMKRESN-IPTQFIWPDHEKPCAV--AQQ
CAB82617.1   Solanum dulca      ----------------------------------------------------------------------------
CAC13038.1   Solanum tuber      ----------------------------------------------------------------------------
CAC13037.1   Solanum tuber      MAIDCMVMPMIQTSS----DEKNP--------------LIFDSSVLKHESN-IPRQFIWPDHEKPSGG--VPE
CAC13036.1   Solanum tuber      MAIDCMITNAKSPMI----DETKQ---------------FIFDASHMKRESN-IPTQFIWPDHEKPCAV--VQE
BAB32733.1   Eustoma grand      ----------------------------------------------------------------------------
CAB96202.1   Citrus sinens      MAIDCIKNIPTML-------HQPK-----EEY--KDEQKPLVFDASVLKHQTQ-IPKQFIWPDDEKPCVN--APE
AAC49211.1   Spinacia ole       MMQPLLTIPPPLPTT-----------------------SLFDTSFLKHEDN-IPSQFIWPDDEKPCSET--PPE
ABF61826.1   Vitis vinifer      MSIVCVEGNPPSMFN----PPTDD-------HKN---QEPLVFDASVLRHQSN-IPKQFIWPDAEKPGDK--ATE CAC00709.1   Populus tremu      MAIDCIKTMPSITTP----HHHPK-----DQDQCKDDGKSFVFDAQVLRHQTN-IPQQFIWPDNEKPNIN--APE
AAT02537.1   Populus tomen      MAIDCIKTMPSITTP---QHHPK-----DQDQCKDDGKSFVFDAQILRHQTN-IPQQFVWPDHEKPNIN--APE
BAC56963.1   Populus nigra      MAIDCIKTMPSITTP----HHHPK-----DQDQCKDDGKSFVFDAQVLRHQTN-IPQQFIWPDHEKPNIN--APE
CAH59142.1   Populus tremu      MAIDCIKTMPSITTP----HHHPK-----DQDQCKDDGKSFVFDAQVLRHQTN-IPQQFIWPDNEKPNIN--APE
CAH59140.1   Populus tremu      MAIDCIKTMPSITTP----HHHPK-----DQDQCKDDGKSFVFDAQVLRHQTN-IPQQFIWPDNEKPNIN--APE
CAH59139.1   Populus tremu      MAIDCIKTMPSITTP----HHHPK-----DQDQCKDDGKSFVFDAQVLRHQTN-IPQQFIWPDNEKPNIN--APE
CAH59138.1   Populus tremu      MAIDCIKTMPSITTP----HHHPK-----DQDQCKDDGKSFVFDAQVLRHQTN-IPQQFIWPDNEKPNIN--APE
CAH59136.1   Populus tremu      MAIDCIKTMPSITTP----HHHPK-----DQDQCKDDGKSFVFDAQVLRHQTN-IPQQFIWPDNEKPNIN--APE
CAH59135.1   Populus tremu      MAIDCIKTMPSITTP----HHHPK-----DQDQCKDDGKSFVFDAQVLRHQTN-IPQQFIWPDNEKPNIN--APE
CAH59134.1   Populus tremu      MAIDCIKTMPSITTP----HHHPK-----DQDQCKDDGKSFVFDAQVLRHQTN-IPQQFIWPDNEKPNIN--APE CAH59133.1   Populus tremu      MAIDCIKTMPSITTP----HHHPK-----DQDQCKDDGKSFVFDAQVLRHQTN-IPQQFIWPDNEKPNIN--APE
CAH59132.1   Populus tremu      MAIDCIKTMPSITTP----HHHPK-----DQDQCKDDGKSFVFDAQVLRHQTN-IPQQFIWPDNEKPNIN--APE
CAH59131.1   Populus tremu      MAIDCIKTMPSITTP----HHHPK-----DQDQCKDDGKSFVFDAQVLRHQTN-IPQQFIWPDNEKPNIN--APE
CAH59130.1   Populus tremu      MAIDCIKTMPSITTP----HHHPK-----DQDQCKDDGKSFVFDAQVLRHQTN-IPQQFIWPDNEKPNIN--APE
CAH59128.1   Populus tremu      MAIDCIKTMPSITTP----HHHPK-----DQDQCKDDGKSFVFDAQVLRHQTN-IPQQFIWPDNEKPNIN--APE
BAC82104.1   Populus alba       MAIDCIKTMPSITTP----HHHPK-----DQDQCKDDGKSFVFDAQVLRHQTN-IPQQFIWPDNEKPNTN--APE
BAC82102.1   Populus alba       MAIDCIKTMPSITTP----HHHPK-----DQDQCKDDGKSFVFDAQVLRHQTN-IPQQFIWPDNEKPNIN--APE
BAA37128.1   Lactuca sativ      -----MPSLHKEHIN-----AQPKP----------------LVFDSLILQHETN-IPEQFIWPDHKEPNSQK-AKE
O04707|GAO1A Triticum aes      ----MVRP------------------------------VFDAAVLSGRSD-IPSFIWPEGESPTPD-AAEE
O04706|GAO1B Triticum aes      ----MVQP------------------------------VFDAAVLSGRAD-IPSFIWPEGESPTPD-AAEE O04705|GAO1D Triticum aes      ----MVQP------------------------------VFDAAVLSGRAD-IPSFIWPEGESPTPD-AAEE
P93771|GAOX1 Oryza sativa      --MSMVVQQEQEV-------------------------VFDAAVLSGQTE-IPSQFIWPAEESPGSV-AVEE
Q8RVF5|GAOX2 Oryza sativa      --MVAEHPTPPQPHQPPPMDSTAG----------SGIAAPAAAAVCDLRMEPK-IPEPFVWPNGDARPAS--AAE
AAN73384.1   Oryza rufipog      --MVAEHPTPPQPHQPPPMDSTAG----------SGIAAPAAAAVCDLRMEPK-IPEPFVWPNGDARPAS--AAE
AAF70814.1   Sorghum bicol      ----------------------------------------------------------------------------
AAG43043.1   Lolium perenn      ----MVQP------------------------------VFDAALLSGQSD-IPSQFIWPADESPSPD-ATEE
AAG43045.1   Lolium perenn      ----MVQP------------------------------VFDAALLSAQSD-IPSQFIWPADESPSPD-ATEE
AAG43044.1   Lolium perenn      ----MVQP------------------------------VFDAALLSGQSD-IPSQFIWPADESPSPD-ATEE
AAG43042.1   Lolium perenn      ----MVQP------------------------------VFDAALLSGQSD-IPSQFIWPADESPSPD-ATEE
ABG67710.1   Zea mays           --MVLAAHDPPPL-------------------------VFDAARLSGLSD-IPQQFIWPADSTPSD-SAEE
ABG33927.1   Zoysia japoni      ----MAAASTPNG-------------------------DPPVRSLATT-VPVQAVLFDIDGTLCD-SDPL
ABF70102.1   Musa balbisia      --MDSVSPVTLD------LNKEEG-----------HCSNSAVVFDTSFLRRQAK-IPESFVWPR-SERPHP--LEE
```

TABLE 3-continued

Alignment of all protein sequences identified as plant GA20oxidases in one database. ▓▓▓▓▓▓▓ conserved sequences believed to be involved in substrate binding (binding to GA). Marked in light grey: conserved sequences believed to be involved in 2-oxoglutarate binding (co-substrate). Sequence fairly conserved within enzyme family 2-oxoglutarate dependent dixoygenases. ▓▓▓▓▓▓▓ $Fe^{2+}$-binding motif, conserved in enzyme family 2-oxoglutarate dependent dioxygenases.

```
                                    80        90        100       110       120       130       140       150
                                ....|....|....|....|....|....|....|....|....|....|....|....|....|....|....|
ABB00359.1|  Fragaria x an      LQVPLIDLGDFLSGNPEAAMKASRLVGEACEKHGFFLVVNHRVKESLIADAHQYMDEFFGLPLSEKQRTQRKAGE
BAB20975.1|  Malus x domes      LQVALIDLGGFLSGDKEAVAKASQLVGEACQKHGFFLIVNHGVDNKLIADAHCYMDDFFGMPLSEKQREARKAGE
AAB64345.1|  Cucurbita max      LDVPTIDLEKFMSGDKSYVEEATRLVDEACRQHGIFFVVNHGVDIEMMGRVHDCMNEFFTMPLDVKQRAKRKVGE
CAA51744.1|  Cucurbita max      LDVPTIDLEKFMSGDKSYVEEATRLVDEACRQHGIFFVVNHGVDIEMMGRVHDCMNEFFTMPLDVKQRAKRKVGE
CAC83626.1|  Cucurbita max      LEVPLIDLSGFLSGEKDAAAEAVRLVGEACEKHGFFLVVNHGVDRKLIGEAHKYMDEFFELPLSQKQSAQRKAGE
CAA70329.1|  Marah macroca      LHVPHIDLKKVLSGDEKDVEEATRLVDEACRKHGFFVVVNHGVDKELMNKVHECMNEFFTLPLDVKQKAHRKVGE
AAD42693.1|  Citrullus lan      LHVPHIDLHKFLNGNESDIEEATRLVDEACRKHGFFVLVNHGVDMELIKGVHECMDEFFTLPFDVKQKSQRKFGE
CAA17539.1|  Arabidopsis t      VELPVIDVSRLIDGAEEEREKCKEAIARASREWGFFQVINHGISMDVLEKMRQEQIRVFREPFDKKS--------

NP_176294.1| Arabidopsis        LQVPVIDLAGFLSNDPLLVSEAERLVSEAAKKHGFFLVTNHGVDERLLSTAHKLMDTFFKSPNYEKLKAQRKVGE
NP_175509.1| Arabidopsis        IKLPVIDLSHLTSGEEVKRKRCVKQMVAAAKEWGFFQIVNHGIPKDVFEMMLLEEKKLFDQPFSVKVRERFSDLS
Q39110|GAOX1_Arabidopsis        LDVPLIDLQNLLS-DPSSTLDASRLISEACKKHGFFLVVNHGISEELISDAHEYTSRFFDMPLSEKQRVLRKSGE
Q39112|GAOX3_Arabidopsis        LQVPLIDLAGFLSGDSCLASEATRLVSKAATKHGFFLITNHGVDESLLSRAYLHMDSFFKAPACEKQKAQRKWGE
Q39111|GAOX2_Arabidopsis        LNVPFIDLS-----SQDSTLEAPRVIAEACTKHGFFLVVNHGVSESLIADAHRLMESFFDMPLAGKQKAQRKPGE
AAY98356.1|  Sesbania rost      LQAPLVDLDGFLRGDEEEATHRAAELISKACLTHGFFQVINHGVDQRLIGEAYNQMDGFFKLPIDRKLSVRKIPGS
AAC49721.1|  Pisum sativum      LDVPLIDFKNFLSGDPFAAMEASKTIGAECEKHGFFLVVNHGIDTKLIEHAHSYMNDFFEVPLSQKQRCQRKTGE
CAA62846.1|  Pisum sativum      LDVPLIDFKNFLSGDPFAAMEASKTIGAECEKHGFFLVVNHGIDTKLIEHAHSYMNDFFEVPLSQKQRCQRKTGE
AAB67838.1|  Pisum sativum      LEVPPIDLKAFLSDDPKSISNACSKVNHACKKHGFFLVVNHGVDNKLIAQAHKLVDEFFCMQLSEKQRAQRKIGE
CAD21845.1|  Fagus sylvati      --------------------------------------------------------------------------

CAD21846.1|  Fagus sylvati      LQVPLIDLRGFLSGDPTAANEASSLVGKACQKHGFFLVVNHGVDDKLIAHAHQYIDYFFELPMSAKQRAQRKVGE
AAC49756.1|  Phaseolus vul      LVVPLIDLRGFLSGDPVATMEAARMVGEACQKHGFFLVVNHGIDANLISHAHSYMDDFFEVPLTQKQRAQRKTGE
AAC49758.1|  Phaseolus vul      LKIPPIDMKGFLSGDPETVSAICAEVNAACRKHGFFLVVNHGVDKKLVEKAHKLIDTFFCMELPEKQKLQRKLGE
AAC49757.1|  Phaseolus vul      LPVPFIDLGGFLSGDPLAATEASRLVGEACQKHGFFLVVNHGIQQQLISDAHLYMDHFFALPLSHKQRAQRMPGE
AAW80969.1|  Gossypium hir      LVIPTIKLGAFLLGDSLAVSKAAEAVNEACKKHGFFLVVNHGVDSGLIDKAHQYMDRFFSLQLSEKQKAKRKVGE
AAT28326.1|  Gossypium hir      LVIPTIDLGAFLLGDSLAVSKAAEVVNEACKKHGFFLVVNHGVDSGLIDKAHQYMDRFFSLQLSEKQKAKRKVGE
ABA01489.1|  Gossypium hir      LVIPTIDLGAFLLRYSLAVSKAAEVVNEACKKHGFFLVVNHGIDLDKAHQYMDRFFSLQLSEKQKAKRKVGE
BAD90753.1|  Ipomoea nil        FQVPVIDMAAFRSGDPVAVEATCKLVDEACKKHGFFLVVNHGVDTELLSDGVREMDRYFELPLSFKEKALRKLGE
BAD90752.1|  Ipomoea nil        CPVPVIDLAAFRSGDPAAVAETLKLVNEACKKHGFFLVVNHGVDPDRISDAIRHMDRFFKLPLSSKEKALRKVGE
BAA32156.1|  Nicotiana tab      LPVPLIDLGGFLSGDPVAAQQASRLVGEACRNHGFFLVVNHGVNANLISNAHRYMDMFFDLPLSEKQKAKRKLEE AAT39975.1|  Solanum demis      LQVPLIDLSGVLSNDPIEIKKATRLVNEACTKHGFFLVTNHGVDTNLIKKAHVYIDKFFELPLCEKQKAQRRVGE
CAB82616.1|  Solanum dulca      LAVPLIDLRGFLSGDSDAAQQASKLVGEACRSHGFFLVVNHGVEANLISNAHRYMDTFFDLPLSEKQKAQRKIGE
CAB82617.1|  Solanum dulca      --------------------------------------------------------------------------
CAC13038.1|  Solanum tuber      ---------------------------------------------AQVYIDKFFELPLCEKQKAQRRVGE
CAC13037.1|  Solanum tuber      LDVPLIDLGAFLSGDPIAAKRESRLVDEACKNHGFFLVGNHGVDTNLISLAHRYMNMFFELPLSNKQMIQRKRGD
CAC13036.1|  Solanum tuber      LHVPLIDLRGFLSGDSDAAQQASKLVGEACRSHGFFLVVNHGVDANLISNAHRYMDTFFDLPLLEKQKAQRKIGE
BAB32733.1|  Eustoma grand      --------------------------------------------------------------------------
CAB96202.1|  Citrus sinens      LQVPLIDLSDDPVAAKEASRLVGEACRKHGFFLVVNHGVDSSLIADAHRYMDHFFELPLNEKQRARRKLGE
AAC49211.1|  Spinacia ole       LEVPPIDLGGFLSGDPVAVSKATTLANEACKWHGFFLIVNHDIYFELLVKAHEAMDYFFSQPFSQKQKALRKQGD
ABF61826.1|  Vitis vinifer      LSVPLIDLGGFLSGDPAAAMEATRLVREACQKHGFFLVVNHGVDDKLIYKAHQYMDSFFGLPLAKKQRAQRKLGE CAC00709.1|  Populus tremu      LQVPLVDLGDFLSGNPVAAVEASRLVGEACKKHGFFLVVNHGVDKTLIAHAHNYVDTFFKLPLSEKQKAQRKIGE
AAT02537.1|  Populus tomen      LQVPLVDLGDFLSGNPVAAVEASRLVGEACKKHGFFLVVNHGVDKTLIAHAHNYVDTFFKLPLSEKQKAQRKIGE
BAC56963.1|  Populus nigra      LQVPLVDLGDFLSGNPVAAVEASRLVGEACQKHGFFLVVNHGVDKTLIAHAHNYMDTFFELPLSEKQKAQRKIGE
CAH59142.1|  Populus tremu      LQVPLVDLGDFLSGNPVAAVEASRLVGEACKKHGFFLVVNHGVDKTLIAHAHNYVDTFFKLPLSEKQKAQRKIGE
CAH59140.1|  Populus tremu      LQVPLVDLGDFLSGNPVAAVEASRLVGEACKKHGFFLVVNHGVDKTLIAHAHNYVDTFFKLPLSEKQKAQRKIGE
CAH59139.1|  Populus tremu      LQVPLVDLGDFLSGNPVAAVEASRLVGEACKKHGFFLVVNHGVDKTLIAHAHNYVDTFFKLPLSEKQKAQRKIGE
CAH59138.1|  Populus tremu      LQVPLVDLGDFLSGNPVAAVEASRLVGEACKKHGFFLVVNHGVDKTLIAHAHNYVDTFFKLPLSEKQKAQRKIGE
CAH59136.1|  Populus tremu      LQVPLVDLGDFLSGNPVAAVEASRLVGEACKKHGFFLVVNHGVDKTLIAHAHNYVDTFFKLPLSEKQKAQRKIGE
CAH59135.1|  Populus tremu      LQVPLVDLGDFLSGNPVAAVEASRLVGEACKKHGFFLVVNHGVDKTLIAHAHNYVDTFFKLPLSEKQKAQRKIGE
CAH59134.1|  Populus tremu      LQVPLVDLGDFLSGNPVAAVEASRLVGEACKKHGFFLVVNHGVDKTLIAHAHNYVDTFFKLPLSEKQKAQRKIGE CAH59133.1|  Populus tremu      LQVPLVDLGDFLSGNPVAAVEASRLVGEACKKHGFFLVVNHGVDKTLIAHAHNYVDTFFKLPLSEKQKAQRKIGE
CAH59132.1|  Populus tremu      LQVPLVDLGDFLSGNPVAAVEASRLVGEACKKHGFFLVVNHGVDKTLIAHAHNYVDTFFKLPLSEKQKAQRKIGE
CAH59131.1|  Populus tremu      LQVPLVDLGDFLSGNPVAAVEASRLVGEACKKHGFFLVVNHGVDKTLIAHAHNYVDTFFKLPLSEKQKAQRKIGE
CAH59130.1|  Populus tremu      LQVPLVDLGDFLSGNPVAAVEASRLVGEACKKHGFFLVVNHGVDKTLIAHAHNYVDTFFKLPLSEKQKAQRKIGE
CAH59128.1|  Populus tremu      LQVPLVDLGDFLSGNPVAAVEASRLVGEACKKHGFFLVVNHGVDKTLIAHAHNYVDTFFKLPLSEKQKAQRKIGE
BAC82104.1|  Populus alba       LQVPLVDLGDFLSGNPVAAVEASRLVGEACKKHGFFLVVNHGVDKTLIAHAHNYVDTFFKLPLSEKQKAQRKIGE
BAC82102.1|  Populus alba       LQVPLVDLGDFLSGNPVAAVEASRLVGEACKKHGFELVTNHGVDASLIVDAHRYMDLFFELPFLDKQRVQRKIGE
BAA37128.1|  Lactuca sativ      LQVPLVDLGDFLSGNPVAAVEASRLVGEACKKHGFELVTNHGVDASLIVDAHRYMDLFFELPFLDKQRVQRKIGE
O04707       GAO1A_Triticum aes LAVPLVDLRGFLSGRASSAKEASVVVGEACERHGFFQVVNHGIDEALLADAHRCVDNFFTMPLPEKQRALRRPGE
O04706       GAO1B_Triticum aes LHVPLINIGGMLSGDAAAAAEVTRLVGEACERHGFFQVVNHGIDEALLADAHCVDAFFTMPLPEKQRALRRPGE O04705       GAO1D_Triticum aes LHVPLIDIGGMLSGDPAAAAEVTRLVGEACERHGFFQVVNHGIDAELLADAHRCVDNFFTMPLPEKQRALRHPGE
P93771       GAOX1_Oryza sativa LEVALIDVGAGA-----ERSSVVGEACERHGFFQVVNHGIEAALLEEAHRCMDAFFTLPLGEKQAQRRAGE
Q8RVF5       GAOX2_Oryza sativa LDMPVVDVGVLRDGDAEGLRRAAAQVAAACATHGFFQVSEHGVDAALARAALDGASDFFRLPLAEKRRARRVPGT
AAN73384.1|  Oryza rufipog      LDMPVVDVGVLRDGDAEGLRRAAAQVAAACATHGFFQVSGHGVDAALARAALDGASDFFRLPLAEKRRARRVPGT
AAF70814.1|  Sorghum bicol      --------------------------------------------------------------------------
AAG43043.1|  Lolium perenn      LHVPLIDIGGLLSGDRVAAAEVTRLVGDACERHGFFQVVNHGIDAELLADAHRCVDAFFTMSLQGKQRALRRPGE
AAG43045.1|  Lolium perenn      LHVPLIDIGGLLSGDREAAAEVTRLVGDACERHGFFQVVNHGIDAELLGHAR-CVDAFFTMSLQDKQRALRRPGE
AAG43044.1|  Lolium perenn      LHVPLIDIGGLLSGDREAAAEVTRLVGDACERHGFFQVVNHGIDAELLADAHRCVDAFFTMSLQGKQRALRRPGE
AAG43042.1|  Lolium perenn      LHVPLIDIGGLLSGDREAAAEVTRLVGDACERHGFFQVVNHGIDAELLADAHRCVDAFFTMSLQDKQRALRRPGE
ABG67710.1|  Zea mays           LAVPLIDLSG-------DAAEVVRQVRRACDLHGFFQVVGHGIDAALTAEAHRCMDAFFTLPLPDKQRAQRRQGD
ABG33927.1|  Zoysia japoni      HHVAFQELLL-------EIGYNNGVPIG----HGFFQVVNHGIDQEPLAEAHRCMDNFFTLPLPEKQRAQRRQGE
ABF70102.1|  Musa balbisia      LEVPVVDLRGLFEGDEASISRAAEASRAACVRHGFFQVINHKVDAKVSGDALDAAGDFFKLPLSTKLRARRQPGS
```

TABLE 3-continued

Alignment of all protein sequences identified as plant GA20oxidases in one database. ▒▒▒▒▒▒▒▒▒ conserved sequences believed to be involved in substrate binding (binding to GA). Marked in light grey: conserved sequences believed to be involved in 2-oxoglutarate binding (co-substrate). Sequence fairly conserved within enzyme family 2-oxoglutarate dependent dixoygenases. ▒▒▒▒▒▒▒▒▒ $Fe^{2+}$-binding motif, conserved in enzyme family 2-oxoglutarate dependent dioxygenases.

```
                              160       170       180       190       200       210       220
                         ....|....|....|....|....|....|....|....|....|....|....|....|....|....|
ABB00359.1| Fragaria x an    HCGYASSFTGRFSSK▒▒▒▒▒▒LSFSYTADQS--SSN-VVKDYLCNAMGEEF-DEFGRVYQDYSEAMSTLSIGIME
BAB20975.1| Malus x domes    SCGYASSFTGRFSSK▒▒▒▒▒▒LSFSYSAEKG--STN-FIQDYFCDKMGEEF-KEFGRVYQDYCKAMSTLSIGIME
AAB64345.1| Cucurbita max    SYGYTNSFFGRFASN▒▒▒▒▒▒FSLRCVAAQN----SSAAHDYVLDTLGSSF-SHHGKAYQECGIALNELGTKIVE
CAA51744.1| Cucurbita max    SYGYTNSFFGRFASN▒▒▒▒▒▒FSLRCVAAQN----SSAAHDYVLDTLGPSF-SHHGKAYQECGIALNELGTKIVE
CAC83626.1| Cucurbita max    HCGYASSFTGRFSSK▒▒▒▒▒▒LSFRFAADES-LNN-LVLHYLNDKLGDQF-AKFGRVYQDYCEAMSGLSLGIME
CAA70329.1| Marah macroca    NFGYANSFIGRFSTK▒▒▒▒▒▒FSLRYLAHEN----SSTARDYVSQVLGPEF-SHHGEVYQECGKALSDLSLRIVE
AAD42693.1| Citrullus lan    NYGYANSFIGRFSNN▒▒▒▒▒▒LSLPYVANHN----STSVQDFVSKCVGPEL-SHQGKVYQECGKALSDLSLKIVE
CAA17539.1| Arabidopsis t    --------------------------------------------------NSTMEKFASESEALAYMLAE NP_176294.1| Arabidopsis     TTGYASSFVGRFKENL▒▒▒▒▒▒SFSFSPTEKSENYSQTVKNYISKTMGDGY-KDFGSVYQEYAETMSNLSLKIME
NP_175509.1| Arabidopsis     KNSYRWGNPSATSPAQYSVSEAFHIILSEVS--------------RISDDR-NNLRTIVETYVQEIARVAQMICE
Q39110|GAOX1_Arabidopsis     SVGYASSFTGRFSTKL▒▒▒▒▒▒SFRFCDDMS---RSKSVQDYFCDALGHGF-QPFGKVYQEYCEAMSSLSLKIME
Q39112|GAOX3_Arabidopsis     SSGYASSFVGRFSSKL▒▒▒▒▒▒SFKFSPEEK--IHSQTVKDFVSKKMGDGY-EDFGKVYQEYAEAMNTLSLKIME
Q39111|GAOX2_Arabidopsis     SCGYASSFTGRFSTKL▒▒▒▒▒▒SFQFSNDNS---GSRTVQDYFSDTLGQEF-EQFGKVYQDYCEAMSSLSLKIME
AAY98356.1| Sesbania rost    MWGYSGAHADRFSSKL▒▒▒▒▒▒SFPFHDNNS----EPVVTNYFNSTLGKTF-EQTGVTFQKYCEAMKGLGMKLME
AAC49721.1| Pisum sativum    HCGYASSFTGRFSSNL▒▒▒▒▒▒SFQFSDEKN--SSN-IVKDYLSNTLGEDF-QQFGEVYQEYCEAMSKLSLGIME
CAA62846.1| Pisum sativum    HCGYASSFTGRFSSNL▒▒▒▒▒▒SFQFSDEKN--PSH-IVKDYLSNTLGEDF-QQFGEVYQEYCEAMSKLSLGIME
AAB67838.1| Pisum sativum    HCGYANSFIGRFSSKL▒▒▒▒▒▒SFRYSADESC----RTVEDYFVNIMGEDF-RQFGIVYQKYCEAMSNLSLGIME
CAD21845.1| Fagus sylvati    --------------NFPWKETLSFRSSAQPD--SSN-IVQDYLCNTMGEDF-KPFGKVYQDYCDAMSTLSLGIME CAD21846.1| Fagus sylvati    HCGYASSFTGRFSFK▒▒▒▒▒▒LSFRSSAQPD--SSN-IVQDYLCNTMGEDF-KPFGKVYQDYCDAMSTLSLGIME
AAC49756.1| Phaseolus vul    HCGYASSFTGRFSSK▒▒▒▒▒▒LSFQFSAEEK--SST-IVKDYLCNTLGQEF-EQFGRVYQDYCDAMSNLSLGIME
AAC49758.1| Phaseolus vul    HCGYANSFIGRFSSK▒▒▒▒▒▒LSFHYAPDT------KTVEDYFLNSMGEEF-REFGSFFQEYCEVMSNLSLEIME
AAC49757.1| Phaseolus vul    HCGYASSFTGRFSSK▒▒▒▒▒▒LSFQYSPRND--SQT-LVKDYLCDKMGKEF-EKFGNVYQDYCEAMSNLSLGIME
AAW80969.1| Gossypium hir    SYGYASSFVGRFSSK▒▒▒▒▒▒LSFRYCPHTQ-----NIVQHYMVNWMGEDF-RDFGRLYQEYCEAMNKVSQEIMG
AAT28326.1| Gossypium hir    SYGYASSFVGRFSSK▒▒▒▒▒▒LSFRYCPHTQ-----NIVQHYMVNWMGEDF-RDFGRLYQEYCEAMNKVSQEIMG
ABA01489.1| Gossypium hir    SYGYASSFVGRFSSK▒▒▒▒▒▒LSFRYCPRTQ-----NIVQHYMVNLMGEDF-RDFGRLYQEYCEAMNKVSQEIMG
BAD90753.1| Ipomoea nil      HCGYASSFTGRFNAK▒▒▒▒▒▒LSFRFSAEKE--CSH-VVGEYFEKTLGQEF-ADLGELYQKYCNAMNTLALEITE
BAD90752.1| Ipomoea nil      SCGYASSFTGRFSAK▒▒▒▒▒▒LSFRYSAQKE--CSH-IVEEYFQESLGQDF-AHIGLVYQKYSNEMSKLALEIME
BAA32156.1| Nicotiana tab    HCGYASSFTGRFSSK▒▒▒▒▒▒LSFRYSAEED--SSH-IVEEYFQNTMGESF-SHLGNVYQEYCNSMSTLSLGIME AAT39975.1| Solanum demis    HCGYASSFIGRFSSK▒▒▒▒▒▒LSFQYSDEKG--SSH-IVEQYFQRTLGEKF-SHIGKIYQEYCNAMSTLSLGIME
CAB82616.1| Solanum dulca    HCGYASSFTGRFSSK▒▒▒▒▒▒LSFRYSAEEN--SSH-IVEEYFQRTLGESF-NHLGNVYQEYCNSMNTLSLGIME
CAB82617.1| Solanum dulca    --------------------LSFQYSDEEG--SSH-IVEDYFQRTMGEKF-SHLGKVYQDYCNAMSTLSLRIME
CAC13038.1| Solanum tuber    HCGYASSFIGGFSSK▒▒▒▒▒▒LSFQYSDEEG--SSH-IVEQYFQRTLGEQF-SYIGKIYQEYCNAMSTLSLGIME
CAC13037.1| Solanum tuber    HCGYASSFTERFSSK▒▒▒▒▒▒LSFSYSALQG--SSH-MVDQYFLKTMGEDF-SHIGKFYQEYCNAMSTLSSGIME
CAC13036.1| Solanum tuber    HCGYASSFTGRFSSK▒▒▒▒▒▒LSFRYSAEEE--SSH-IVEDIFKGHWVKIL-TILGNVYQEYCNSKNTLSLGIME
BAB32733.1| Eustoma grand    --------------------------------------------------------------------------
CAB96202.1| Citrus sinens    HCGYASSFTGRFSSK▒▒▒▒▒▒LSFRYSAEKS--LSNNIVEDYLLNTMGDEF-KQFGRVYQDYCESMSRLSLGIME
AAC49211.1| Spinacia ole     HCGYASSFLGRFATK▒▒▒▒▒▒LSFRYYDDDDDKSSK-MVQNYISNLMGTDF-QEFGRVYQEYCKAMSKLSLGIME
ABF61826.1| Vitis vinifer    HCGYASSFIGRFSSK▒▒▒▒▒▒LSFSYSAEKK--SSN-AVQEYFLNKMGEDF-SEFGQVYQDYCEAMSTLSLVIME CAC00709.1| Populus tremu    SCGYASSFTGRFSSK▒▒▒▒▒▒LSFRYKAEEN--SSK-HIEEYFHNRMGEDF-AEFGTVYQDYCEAMSTLSLGIME
AAT02537.1| Populus tomen    SCGYASSFTGRFSSK▒▒▒▒▒▒LSFRYTAEEN--SSK-HIEEYFHNRMGEDF-AEFGRVYQDYCEAMSTLSLGIME
BAC56963.1| Populus nigra    SCGYASSFTGRFSSK▒▒▒▒▒▒LSFRYTAEKN--SSK-HIEEYFHNRMGEDF-AEFGTVYQDYCEAMSTLSLGIME
CAH59142.1| Populus tremu    SCGYASSFTGRFSSK▒▒▒▒▒▒LSFRYKAEEN--SPK-HIEEYFRNRMGEDF-AEFGTVYQDYCEAMSTLSLGIME
CAH59140.1| Populus tremu    SCGYASSFTGRFSSK▒▒▒▒▒▒LSFRYKAEEN--SSK-HIEEYFHNRMGEDF-AEFGTVYQDYCEAMSTLSLGIME
CAH59139.1| Populus tremu    SCGYASSFTGRFSSK▒▒▒▒▒▒LSFRYKAEEN--SSK-HIEEYFHNRMGEDF-AEFGTVYQDYCEAMSTLSLGIME
CAH59138.1| Populus tremu    SCGYASSFTGRFSSK▒▒▒▒▒▒LSFRYKAEEN--SPK-HIEEYFHNRMGEDF-AEFGTVYQDYCEAMSTLSLGIME
CAH59136.1| Populus tremu    SCGYASSFTGRFSSK▒▒▒▒▒▒LSFRYKAEEN--SPK-HIEEYFHNRMGEDF-AEFGTVYQDYCEAMSTLSLGIME
CAH59135.1| Populus tremu    SCGYASSFTGRFSSK▒▒▒▒▒▒LSFRYKAEEN--SPK-HIEEYFHNRMGEDF-AEFGTVYQDYCEAMSTLSLGIME
CAH59134.1| Populus tremu    PCGYASSFTGRFSSK▒▒▒▒▒▒LSFRYKAEEN--SPK-HIEEYFHNRMGEDF-AEFGTVYQDYCEAMSTLSLGIME CAH59133.1| Populus tremu    SCGYASSFTGRFSSK▒▒▒▒▒▒LSFRYKAEEN--SSK-HIEEYFHNRMGEDF-AEFGTVYQDYCEAMSTLSLGIME
CAH59132.1| Populus tremu    SCGUASSFTGRFSSL▒▒▒▒▒▒LSFRYQAEEN--SPK-HIEEYFHNRMGEDF-AEFGTVYQDYCEAMSTLSLGIME
CAH59131.1| Populus tremu    SCGYASSFTGRFSSK▒▒▒▒▒▒LSFRYKAEEN--SPK-HIEEYFHNRMGEDF-AEFGTVYQDYCEAMSTLSLGIME
CAH59130.1| Populus tremu    SCGYASSFTGRFSSK▒▒▒▒▒▒LSFRYKAEEN--SSK-HIEEYFHNRMGEDF-AEFGTVYQDYCEAMSTLSLGIME
CAH59128.1| Populus tremu    SCGYASSFTGRFSSK▒▒▒▒▒▒LSFRYKAEEN--SPK-HIEEYFHNRMGEDF-AEFGTVYQDYCEAMSTLSLGIME
BAC82104.1| Populus alba     SCGYASSFTGRFSSK▒▒▒▒▒▒LSFRYKAEES--SSK-HIEEYFHNRMGEDF-AEFGTVYQDYCEAMSTLSLGIME
BAC82102.1| Populus alba     SCGYASSFTGRFSSK▒▒▒▒▒▒LSFRYKAEEN--SSK-HIEEYFHNRMGEDF-AEFGTVYQDYCEAMSTLSLGIME
BAA37128.1| Lactuca sativ    SCGYASSFTGRFSSK▒▒▒▒▒▒LSFQFSGEKK--SSK-IVEEYFEKTMGKEF-ARLGKVYQEYCNAMSRLSLGIME
O04707|GAO1A_Triticum aes   SCGYASSFTGRFASK▒▒▒▒▒▒LSFRSCPSD-----PALVVDYIVATLGEDH-RRLGEVYARYCSEMSRLSLEIME
O04706|GAO1B_Triticum aes   SCGYASSFTGRFASK▒▒▒▒▒▒LSFRSCPSD-----PALVVDYIVATLGEDH-RRLGEVYARYCSEMSRLSLEIME O04705|GAO1D_Triticum aes   SCGYASSFTGRFASK▒▒▒▒▒▒LSFRSCPSD-----PALVVDYIVATLGEDH-RRLGEVYARYCSEMSRLSLEIME
P93771|GAOX1_Oryza sativa   SCGYASSFTGRFASK▒▒▒▒▒▒LSFRYSSAG-DEEGEEGVGEYLVRKLGAEHGRRLGEVYSRYCHEMSRLSLELME
Q8RVF5|GAOX2_Oryza sativa   VSGYTSAHADRFASK▒▒▒▒▒▒LSFGFHDRAA----APVVADYFSSTLGPDF-APMGRVYQKYCEEMKELSLTIME
AAN73384.1| Oryza rufipog    VSGYTSAHADRFASK▒▒▒▒▒▒LSFGFHDRAA----APVVADYFSSTLGPDF-APMGRVYQKYCEEMKELSLTIME
AAF70814.1| Sorghum bicol    -----------FASK▒▒▒▒▒▒LSFRYSDDQ-GDG--DVVVDYFVDKLGDAY-RHHGEVYGRYCSEMSRLSLELME
AAG43043.1| Lolium perenn    SCGYASSFTGRFASK▒▒▒▒▒▒LSFRSCPSE-----PDLVVEYIVATLGEDH-RRLGEVYARYCSEMSRLSLELME
AAG43045.1| Lolium perenn    SCGYASSFTGRFASK▒▒▒▒▒▒LSFRSCPSE-----PDLVVEYIVATLGEDH-RRLGEVYARYCSEMSRLSLELME
AAG43044.1| Lolium perenn    SCGYASSFTGRFASK▒▒▒▒▒▒LSFRSCPSE-----PDLVVEYIVATLGEDH-RRLGEAYARYCSEMSRLSLELME
AAG43042.1| Lolium perenn    SCGYASSFTGRFASK▒▒▒▒▒▒LSFRSCPSE-----PDLVVDYIVATLGEDH-RRLGEVYARYCSEMSRLSLELME
ABG67710.1| Zea mays         SCGYASSFTGRFASK▒▒▒▒▒▒LSFRYTDDDDGDKSKDVVASYFVDKLGEGY-RHHGEVYGRYCSEMSRLSLELME
ABG33927.1| Zoysia japoni    SCGYASSFTGRFACK▒▒▒▒▒▒LSFRYSSNP---SSPDLVVDYFVEKLGEDY-RHHGAVYARYCSEMSRLSLEMMG
ABF70102.1| Musa balbisia    AWGYVGAHADRFASK▒▒▒▒▒▒LTFGYDYGER----GDGVVDYFTSKLGEGF-EPMGRVYRRYCEAMKELSLSIME
```

TABLE 3-continued

Alignment of all protein sequences identified as plant GA20oxidases in one database. ▓▓▓▓▓ conserved sequences believed to be involved in substrate binding (binding to GA). Marked in light grey: conserved sequences believed to be involved in 2-oxoglutarate binding (co-substrate). Sequence fairly conserved within enzyme family 2-oxoglutarate dependent dioxygenases. ▓▓▓▓▓ $Fe^{2+}$-binding motif, conserved in enzyme family 2-oxoglutarate dependent dioxygenases.

```
                             230       240       250       260       270       280       290       300
                        ....|....|....|....|....|....|....|....|....|....|....|....|....|....|....|
ABB00359.1| Fragaria x an    LLGMSLGVG---RTHFKEFFGDNDSIMRLNYYPPCQKPDQTLGTGPHCBPTSLTILHQD-QVGGPEVFV-----D
BAB20975.1| Malus x domes    LLGLSLGVD---RAYFKEFFEDNNSIMRLNYYPPCQRPEQTLGTGPHCBPTALTILHED-QVGGLEVFV-----D
AAB64345.1| Cucurbita max    LLGLSLGIS---REYFKNFYKDNDSILRLNYYPTCDKPEVVLGTGPHTBPTSVTILHQD-PVSGLQVCS-----N
CAA51744.1| Cucurbita max    LLGLSLGIS---REYFKNFFEDNDSILRLNYYPTCDKPEVVLGTGPHTBPTSVTILHQD-PVSGLQVCS-----N
CAC83626.1| Cucurbita max    LLGKSLGVE---EQCFKNFFKDNDSIMRLNFYPPCQKPHLTLGTGPHCBPTSLTILHQD-QVGGLQVFV-----D
CAA70329.1| Marah macroca    LLGLSLGIS---RETFPRKFYEDNDSIMRMNYYPRCEKPELTLGTGPHCBPTSITILHQD-DVSGLQVYV-----D
AAD42693.1| Citrullus lan    LLGLSLGVP---KEKFKKFYEDNDSIIRLNYYPPCEKPELTLGTGPHCBPTSITILHQD-HVSGLQVYV-----D
CAA17539.1| Arabidopsis t    VLAEKSGQN---SSFFKENCVRNTCYLRMNRYPPCPKPSEVYGLMPHTBSDFLTILYQD-QVGGLQLIK-----D NP_176294.1| Arabidopsis     LLGMSLGIK---REHFREFFEDNESIFRLNYYPKCKQPDLVLGTGPHCBPTSLTILQQD-QVSGLQVFV-----D
NP_175509.1| Arabidopsis     ILGKQVNVS---SEYFENIFELENSFLRLNKYHPSVFGSEVFGLVPHTBTSFLTILSQD-QIGGLELEN-----N
Q39110|GAOX1_Arabidopsis     LLGLSLGVK---RDYFREFFEEDSDSIFRLNYYPQCKQPELALGTGPHCBPTSLTILHQD-HVNGLQVFV-----E
Q39112|GAOX3_Arabidopsis     LLGLSLGVN---RDYFRGFFEENDSIFRLNYYPQCKQPELALGTGPHCBPTSLTILHQD-HVNGLQVFV-----D
Q39111|GAOX2_Arabidopsis     LLGLSLGVN---RDYFRGFFEENDSIMRLNHYPPCQTPDLTLGTGPHCBPSSLTILHQD-HVNGLQVFV-----D
AAY98356.1| Sesbania rost    LLAISLDVD---RPHYKDLFEDGCSIMRCNYYPSCQQPSLALGTGPHCBPTTLTILHQD-QVGGLDVFA-----D
AAC49721.1| Pisum sativum    LLGMSLGVG---KECFRDFFEENKSIMRLNYYPPCQKPDLTLGTGPHCBPTSLTILHQD-QVGGLQVFV-----D
CAA62846.1| Pisum sativum    LLGMSLGVG---KECFRDFFEENKSIMRLNYYPPCQKPDLTLGTGPHCBPTSLTILHQD-QVGGLQVFV-----D
AAB67838.1| Pisum sativum    LLGMSLGVG---KEYFREFFEGNESVMRLNYYPPCKNPDLAFGTGPHCBPTSLTILHQD-QVEGLQVLV-----D
CAD21845.1| Fagus sylvati    LLGMSLGVS---QGHYREFFEENESIMRLNYYPPCQKPDLTLGTGPHCBPTSLTILHQD-QVGGLQVFV-----D CAD21846.1| Fagus sylvati    LLGMSLGVS---QGHYREFFEENESIMRLNYYPPCQKPDLTLGTGPHCBPTSLTILHQD-QVGGLQVFV-----D
AAC49756.1| Phaseolus vul    LLGMSLGVG---KACFREFFEENDSIMRLNYYPPCQKPDLTLGTGPHCBPTSLTILHQD-QVGGLQVFV-----D
AAC49758.1| Phaseolus vul    LLGMSLGVS---RECFRDFFKNNESVMRLNYYPPCHKPELALGTGPHCBPTSLTVLHQD-QVEGLQVFV-----D
AAC49757.1| Phaseolus vul    LLGLSLGVG---RGYFREFFEENNSIMRLNYYPPCQKPDLTLGTGPHCBPTSLTILHQD-QVGGLQVCV-----D
AAW80969.1| Gossypium hir    LLGISLGLD---QAYFKDFFEDENDSILRLNHYPPCQKPELTLGTGPHTBPTSLTILHQD-QVGGLQVFA-----D
AAT28326.1| Gossypium hir    LLGISLGLD---QAYFKDFFEQNDSILRLNHYPPCQKPELTLGTGPHTBPTSLTILHQD-QVGGLQVFA-----D
ABA01489.1| Gossypium hir    LLGISLGLD---QAYFKDFFEQNDSILRLNHYPPCQKPELTLGTGPHTBPTSLTILHQD-QVGGLQVFA-----D
BAD90753.1| Ipomoea nil      LLGMGLGVD---RKHFSEFYQENDSVLRLNYYPPCQKPELTLGTGPHCBPTSLTILHQD-SVSGLQVFV-----D
BAD90752.1| Ipomoea nil      VLGMGLGVN---RKHFSDFFQENDSVMRLNYCPPCQKPEITLGTGPHCBPTSLTILHQDNSVNGLQVCV-----D
BAA32156.1| Nicotiana tab    LLGMSLGVG---REHFKEFFEENESIMRLNYYPPCQKPDLTLGTGPHCBPTSLTILHQD-SVGGLQVFV-----D AAT39975.1| Solanum demis    LLGLSLGVS---KNHFKEFFQENESIMRLNYYPTCQKPELTLGTGPHCBPTSLTILHQD-SVGGLQVFV-----D
CAB82616.1| Solanum dulca    LLGMSLGVE---KSHFKEFFEENDSIMRLNYYPPCQKPELTLGTGPHCBPTSLTILHQD-CVGGLQVFV-----D
CAB82617.1| Solanum dulca    LLGLSLGVS---NHHFKEFFQENESIMRLNYYPTCQKPELTLGTGPHCBPTSLTILHQD-SVGGLQVFV-----D
CAC13038.1| Solanum tuber    LLGLSLGVS---KNHFKEFFQENESIMRLNYYPTCQKPELTLGTGPHCBPTSLTILHQD-SVGGLQVFV-----D
CAC13037.1| Solanum tuber    LLGESLGVS---KNHFKQFFEENESIMRLNYYPTCQKPDLALGTGPHCBPTSLTILHQD-SVSGLQVFM-----D
CAC13036.1| Solanum tuber    LLGMSLGVE---KSHFKEFFEENDSIMRLNYYPPCQKPELTLGTGPHCBPTSLTILHQD-CVGGLQVFV-----D
BAB32733.1| Eustoma grand    ----------------------------------------GTGPHCBPTSLTILHQD-SVGGLQVFV-----D
CAB96202.1| Citrus sinens    LLAISLGVG---RAHFKEFFEENDSIMRLNYYPPCQKPELTLGTGPHCBPTSLTILHQD-QVGGLQVFV-----D
AAC49211.1| Spinacia ole     LLGMSLGVG---RNYFREFFKGNDSIIRLNYYPPCEKPDLTLGTGPHCBPTSLTILHQD-HVGGLEVFV-----D
ABF61826.1| Vitis vinifer    LLGMSLGIG---GAHFREFFEENDSIMRLNYYPPCLKPDLTLGTGPHCBPTSLTILHQD-QVGGLQVFV-----D CAC00709.1| Populus tremu    LLGMSLGVS---REHFREFFNENDSIMRLNYYPPCQKPDLTLGTGPHCBPTSLTILHQD-QVGGLQVFV-----D
AAT02537.1| Populus tomen    LLGMSLGVS---REHFREFFNENDSIMRLNYYPPCQKPDLTLGTGPHCBPTSLTILHQD-QVGGLQVFV-----D
BAC56963.1| Populus nigra    LLGMSLGVS---REHFREFFNENDSIMRLNYYPPCQKPDLTLGTGPHCBPTSLTILHQD-QVGGLQVFV-----D
CAH59142.1| Populus tremu    LLGMSLGVS---REHFREFFNENDSIMRLNYYPPCQKPDLTLGTGPHCBPTSLTILHQD-QVGGLQVFV-----D
CAH59140.1| Populus tremu    LLGMSLGVS---REHFREFFNENDSIMRLNYYPPCQKPDLTLGTGPHCBPTSLTILHQD-QVGGLQVFV-----D
CAH59139.1| Populus tremu    LLGMSLGVS---REHFREFFNENDSIMRLNYYPPCQKPDLTLGTGPHCBPTSLTILHQD-QVGGLQVFV-----D
CAH59138.1| Populus tremu    LLGMSLGVS---REHFREFFNENDSIMRLNYYPPCQKPDLPLGTGPHCBPTSLTILHQD-QVGGLQVFV-----D
CAH59136.1| Populus tremu    LLGMSLGVS---REHFREFFNENDSIMRLNYYPPCQKPDLTLGTGPHCBPTSLTILHQD-QVGGLQVFV-----D
CAH59135.1| Populus tremu    LLGMSLGVS---REHFREFFNENDSIMRLNYYPPCQKPDLTLGTGPHCBPTSLTILHQD-QVGGLQVFV-----D
CAH59134.1| Populus tremu    LLGMSLGVS---REHFREFFNENDSIMRLNYYPPCQKPDLTLGTGPHCBPTSLTILHQD-QVGGLQVFV-----D CAH59133.1| Populus tremu    LLGMSLGVS---REHFREFFNENDSIMRLNYYPPCQKPDLTLGTGPHCBPTSLTILHQD-QVGGLQVFV-----D
CAH59132.1| Populus tremu    LLGMSLGVS---REHFREFFNENDSIMRLNYYPPCQKPDLTLGTGPHCBPTSLTILHQD-QVGGLQVFV-----D
CAH59131.1| Populus tremu    LLGMSLGVS---REHFREFFNENDSIMRLNYYPPCQKPDLTLGTGPHCBPTSLTILHQD-QVGGLQVFV-----D
CAH59130.1| Populus tremu    LLGMSLGVS---REHFREFFNENDSIMRLNYYPPCQKPDLTLGTGPHCBPTSLTILHQD-QVGGLQVFV-----D
CAH59128.1| Populus tremu    LLGMSLGVS---REHFREFFNEDDSIMRLNYYPPCQKPDLTLGTGPHCBPTSLTILHQD-QVGGLQVFV-----D
BAC82104.1| Populus alba     LLGMSLGVS---REHFREFFNENDSIMRLNYYPPCQKPDLTLGTGPHCBPTSLTILHQD-QVGGLQVFV-----D
BAC82102.1| Populus alba     LLGMSLGVS---REHFREFFNENDSIMRLNYYPPCQKPDLTLGTGPHCBPTSLTILHQD-QVGGLQVFV-----D
BAA37128.1| Lactuca sativ    LLGMSLGVE---QSHFKEFFKENDSIMRLNYYPPCQKPDLTLGTGPHCBPTSLTILHQD-TVGGLEVFI-----D
O04707 GAO1A_Triticum aes    VLGESLGVG---RAHYRRFFEGNDSIMRLNYYPPCQRPLETLGTGPHCBPTSLTILHQD-NVGGLVHT-----E
O04706|GAO1B_Triticum aes    VLGESLGVG---RAHYRRFFEGNDSIMRLNYYPPCQRPMETLGTGPHCBPTSLTILHQD-NVGGLVHT-----E O04705|GAO1D_Triticum aes    VLGESLGVG---RAHYRRFFEGNDSIMRLNYYPPCQRPLETLGTGPHCBPTSLTILHQD-NVGGLVHT-----E
P93771|GAOX1_Oryza sativa    VLGESLGIVGDRRHYFRRFFQRNDSIMRLNYYPACQRPLDTLGTGPHCBPTSLTILHQD-NVGGLEVWA-----E
Q8RVF5|GAOX2_Oryza sativa    LLELSLGVE---RGYYREFFADSSSIMRCNYYPPCPEPERTLGTGPHCBPTALTILLQD-DVGGLEVLV-----D
AAN73384.1| Oryza rufipog    LLELSLGVE---RGYYREFFADSSSIMRCNYYPPCPEPERTLGTGPHCBPTALTILLQD-DVGGLEVLV-----D
AAF70814.1| Sorghum bicol    VLGESLGVG---RRHFRRFFQGNGSIMRLNYYPPCQRPYDTLGTGPHCBPTSLTILHQD-DVGGLQVFDGTGPGT
AAG43043.1| Lolium perenn    VLGESLGVG---RAHYRRFFEGNESIMRLNYYPPCQRPNETLGTGPHCBPTSLTILHQD-DVGGLQVHA-----E
AAG43045.1| Lolium perenn    VLGESLGVG---RAHYRRFFEGNESIMRLNYYPPCQRPNETLGTGPHCBPTSLTILHQD-DVGGLQVHA-----E
AAG43044.1| Lolium perenn    VLGESLGVG---RAHYRRFFEGNESIMRLNYYPPCQRPNETLGTGPHCBPTSLTILHQD-DVGGLQVHA-----E
AAG43042.1| Lolium perenn    VLGESLGVG---RAHYRRFFEGNESIMRLNYYPPCQRPNGTLGTGPHCBPTSLTILHQD-DVGGLQVHA-----E
ABG67710.1| Zea mays         VLGESLGVG---RRHFRRFFQGNESIMRLNYYPPCQRPYDTLGTGPHCBPTSLTILHQD-DVGGLQVFD---AAT
ABG33927.1| Zoysia japoni    ILGESLGVG---RDHFRRFFQPNESIMRLNYYPPCQRPLETLGTGPHCBPTSLTILHQD-HVGGLQVFT-----D
ABF70102.1| Musa balbisia    LLGISLGVG---REYYRQFFEDGSSIMRCNSYPPCQEPELALGTGPHCBPTALTILLQD-QVGGLQVFT-----E
```

TABLE 3-continued

Alignment of all protein sequences identified as plant GA20oxidases in one database. ▓▓▓▓▓▓▓ conserved sequences believed to be involved in substrate binding (binding to GA). Marked in light grey: conserved sequences believed to be involved in 2-oxoglutarate binding (co-substrate). Sequence fairly conserved within enzyme family 2-oxoglutarate dependent dixoygenases. ▓▓▓▓▓▓▓ $Fe^{2+}$-binding motif, conserved in enzyme family 2-oxoglutarate dependent dioxygenases.

```
                                  310       320       330       340       350       360       370
                              ....|....|....|....|....|....|....|....|....|....|....|....|....|....|
ABB00359.1|  Fragaria x an    EEWRSISPNLNAFVVNIGDAFMALSNGRYKSCLHRAVVNSKTPRKSLAFFLCPKDDKVVKPPR------ELIDSS
BAB20975.1|  Malus x domes    DQWHSVTPNLNAFVVNIGDTFMALSNGKYKSGLHRAVVNSETPRKSLAFFLCPRDDKVVKPPS------GLVDTS
AAB64345.1|  Cucurbita max    DQWYSIPPNPEAFVINIGDTFTSLTNGIYKGCIHRAVVNSMNARKSLAFFLCPSHDKVVRAPE------ELVEKS
CAA51744.1|  Cucurbita max    DQWYSIPPNPEAFVINIGDTFTSLTNGIYKGCIHRAVVNSMNARKSLAFFLCPSHDKVVRAPE------ELVEKS
CAC83626.1|  Cucurbita max    NQWRLITPNFDAFVVNIGDTFMALSNGRYKSCLHRAVVNSERTRKSLAFFLCPRNDKVVRPPR------ELVDTQ
CAA70329.1|  Marah macroca    DQWHSIPPTEDSFVVNVGDTFMSLTNGVYKSCFHRAVVNCKEARKSMAFFLCPAVEKVVRAPE------ELVEKY
AAD42693.1|  Citrullus lan    DEWHSIPPTKDSFVINIGDTFMALTNGVYKSCFHRAVVNCKEVRKSMAFFLCPAADKVVRAPD------EVVEKN
CAA17539.1|  Arabidopsis t    NRWIAVKPNPKALIINIGDLFQAWSNGMYKSVEHRVMTNPKVERFSTAYFMCPSYDAVIECSSD-----------

NP_176294.1|  Arabidopsis     NQWQSIPPIPQALVVNIGDTLMALTNGIYKSCLHRAVVNGETTRKTLAFFLCPKVDKVVKPPS------ELE---
NP_175509.1|  Arabidopsis     GQWISVKPCLEALTVNIGDMFQALSNGVYQSVRHRVISPANIERMSIAFFVCPYLETEIDCFGY-----------
Q39110|GAOX1_Arabidopsis      NQWRSIRPNPKAFVVNIGDTFMALSNDRYKSCLHRAVVNSESERKSLAFFLCPKKDRVVTPPR------ELLDS-
Q39112|GAOX3_Arabidopsis      NKWQSIPPNPHAFVVNIGDTFMALTNGRYKSCLHRAVVNSERERKTFAFFLCPKGEKVVKPPE------ELVNGV
Q39111|GAOX2_Arabidopsis      NQWQSIRPNPHAFVVNIGDTFMALSNGIFKSCLHRAVVNRESARKSMAFFLCPKKDKVVKPPS------DILEK-
AAY98356.1|  Sesbania rost    KKWQTVRPLPHALVVNIGDTFTALSNGRYKSCLHRAVVNQYKERRSLAFFVCPKEDKVVRPPED------IVRRD
AAC49721.1|  Pisum sativum    NEWHSIRPNPNFNAFVVNIGDTFMALSNGRYKSCLHRAVVNNKTTRKSLAFFLCPKGDKVVSPPS------ELVNDL
CAA62846.1|  Pisum sativum    NEWHSIRPNPHAFVVNIGDTFMALSNGRYKSCLHRAVVNNKTTRKSLAFFLCPKGDKVVSPPS------ELVNDL
AAB67838.1|  Pisum sativum    GIWHSVVPKEDAFVVNIGDTFMALSNGMFKSCLHRAIVNDKIVRKSLAFFLCPNEDKIVTPPK------ELIDKE
CAD21845.1|  Fagus sylvati    EEWRSITPNFNAFVVNIGDTFMALSNGRYKSCLHRAMVNSKTPRKSLAFFFEPK--------------------

CAD21846.1|  Fagus sylvati    EEWRSITPNFNAFVVNIGDTFMALSNGRYKSCLHRAVVNSKTPRKSLAFFLCPKNDKVVSPPS------ELVDSL
AAC49756.1|  Phaseolus vul    NEWHSINPNFNAFVVNIGDTFMALSNGRYKSCLHRAVVNSKTTRKSLAFFLCPKGDKVVSPPS------ELVDDL
AAC49758.1|  Phaseolus vul    GKWCSVAPKEDAFVVNIGDTFMALSNGIFKSCLHRAVVNNQIVRKSLAFFLCPNKDKVVSAPK------ELITVE
AAC49757.1|  Phaseolus vul    NEWHSIKPDVNAFVVNIGDTFMALSNGRYKSCLHRAVVNSETTRKSLAFFLCPRSDKVVSPPC------ELVDKL
AAW80969.1|  Gossypium hir    EKWHSVAPIPRAFVVNIGDTFMALTNGIYKSCLHRAVVNTETVRKSLVFFLCPKLERPVTPAA------GLVNAA
AAT28326.1|  Gossypium hir    EKWHSVAPIPGAFVVNVGDTFMALTNGFYKSCLHRAVVNTETVRKSLAFFLCPKLERPVTPAA------GLVTAE
ABA01489.1|  Gossypium hir    EKWHSVAPYPGAFVVNVGDTFMALTKAFYKSCLHRAVVNTETVRKSLRFFLCPKLERPVTPAA------GLVTAE
BAD90753.1|  Ipomoea nil      NEWRAVNPTPNAFVVNIGDTFMALSNGLYKSCMHRAVVNNEIPRKSIAFFLCPHDKVVTPPP------ELVDAT
BAD90752.1|  Ipomoea nil      NEWRSVSPSPNAFVVNIGDTFMALSNGIYKSCLHRAVVNSTITRKSMAFFLCPHEDKVVTPPP------ELVDST
BAA32156.1|  Nicotiana tab    NEWRSVSPNFNAFVVNIGDTFMALSNGRYKSCLHRAVVNNKTPRKSLAFFLVPKKDKVVSPPN------ELVDTN AAT39975.1|  Solanum demis    NEWHSITPNFNAFVVNIGDTFMALSNGRYKSCLHRALVNNKVPRKSLTFFLCPKKDKVVTPPI------ELVDSN
CAB82616.1|  Solanum dulca    DEWRSITPTFNAFVVNIGDTFMALSNGRYKSCLHRAVVNNKTPRKSLAFFLCPNKDKVVSPPN------ELVDSN
CAB82617.1|  Solanum dulca    NEWHSITPNFNAFVVNIGDTFMALSNGRYKSCLHRAVVNNKIPRKSLAFFLCPKKDKVVTPPI------ELVDSN
CAC13038.1|  Solanum tuber    NEWHSITPNFNAFVVNIGDTFMALSNGRYKSCLHRALVNNKVPRKSLTFFLCPKKDKVVTPPI------ELVDSN
CAC13037.1|  Solanum tuber    NQWRSISPNLSAFVVNIGDTFMALSNGRYKSCLHRAVVNNKTPRKSLAFFLCPKKDKVVRPPA------ELVDSN
CAC13036.1|  Solanum tuber    DEWRSISPNFNAFVVNIGDTFMALSNGRYKSCLHRAVVNNKTPRKSLAFFLCPNKDKVVSPPN------ELVDSN
BAB32733.1|  Eustoma grand    DEWRSISPNAGAFVVNIGDTFMALSNGRYKSCLHRAVVN-----------------------------------
CAB96202.1|  Citrus sinens    NEWRSISPNFEAFVVNIGDTFMALSNGRYKSCLHRAVVNSQTTRKSLAFFLCPKNDKVVSPPS------ELVDTY
AAC49211.1|  Spinacia ole     QKWYSIRPNQKAFVVNIGDTFMALSNGKYKSCLHRAVVNSKTPRKSVAFFLCPRGNKVIRPPI------ELGH--
ABF61826.1|  Vitis vinifer    DKWWSISPNFDAFVVNIGDTFMALSNGRYKSCLHRAVVNSQTPRKSLAFFLCPEKDKVVRPPT------ELVDTN CAC00709.1|  Populus tremu    NEWRSINPNFDAFVVNIGDTFMALSNGIYKSCLHRAVVNSQTPRKSLAFFLCPKNDKMVTPPH------ELVDTC
AAT02537.1|  Populus tomen    NEWRSINPNFDAFVVNIGDTFMALSNGIYKSCLHRAVVNGQTPRKSLAFFLCPKNDKMVTPPH------ELVDTC
BAC56963.1|  Populus nigra    NEWRSISPNFDAFVVNIGDTFMALSNGIYKSCLHRAVVNSQTPRKSLAFFLCPKNDKMVTPPH------ELVDTC
CAH59142.1|  Populus tremu    NEWRSINPNFDAFVVNIGDTFMALSNGIYKSCLHRAVVNSQTPRKSLAFFLCPKNDKMVTPPH------ELVDTC
CAH59140.1|  Populus tremu    NEWRSINPNFDAFVVNIGDTFMALSNGVYKSCLHRAVVNSQTPRKSLAFFLCPKNDKMVTPPH------ELVDTC
CAH59139.1|  Populus tremu    NEWRSINPNFDAFVVNIGDTFMALSNGIYKSCLHRAVVNSQTPRKSLAFFLCPKNDKMVTPPH------ELVDTC
CAH59138.1|  Populus tremu    NEWRSINPNFDAFVVNIGDTFMALSNGIYKSCLHRAVVNSQTPRKSLAFFLCPKNDKMVTPPH------ELVDTC
CAH59136.1|  Populus tremu    NEWRSINPNFDAFVVNIGDTFMALSNGIYKSCLHRAVVNSQTPRKSLAFFLCPKNDKMVTPPH------ELVDTC
CAH59135.1|  Populus tremu    NEWRSINPNFDAFVVNIGDTFMALSNGIYKSCLHRAVVNSQTPRKSLAFFLCPKNDKMVTPPH------ELVDTC
CAH59134.1|  Populus tremu    NEWRSINPNFDAFVVNIGDTFMALSNGIYKSCLHRAVVNSQTPRKSLAFFLCPKNDKMVTPPH------ELVDTC CAH59133.1|  Populus tremu    NEWRSINPNFDAFVVNIGDTFMALSNGIYKSCLHRAVVNSQTPRKSLAFFLCPKNDKMVTPPH------ELVDTC
CAH59132.1|  Populus tremu    NEWRSINPNFDAFVVNIGDTFMALSNGIYKSCLHRAVVNSQTPRKSLAFFLCPKNDKMVTPPH------ELVDTC
CAH59131.1|  Populus tremu    NEWRSINPNFDAFVVNIGDTFMALSNGIYKSCLHRAVVNSQTPRKSLAFFLCPKNDKMVTPPH------ELVDTC
CAH59130.1|  Populus tremu    NEWRSINPNFDAFVVNIGDTFMALSNGIYKSCLHRAVVNSQTPRKSLAFFLCPKNDKMVTPPH------ELVDTC
CAH59128.1|  Populus tremu    NEWRSINPNFDAFVVNIGDTFMALSNGIYKSCLHRAVVNSQTPRKSLAFFLCPKNDKMVTPPH------ELVDTC
BAC82104.1|  Populus alba     NEWRSINPNFDAFVVNIGDTFMALSNGIYRSCLHRAVVNSQTPRKSLAFFLCPKNDKMVTPPH------ELVDTC
BAC82102.1|  Populus alba     NEWRSINPNFDAFVVNIGDTFMALSNGIYRSCLHRAVVNSQTPRKSLAFFLCPKNDKMVTPPH------ELVDTC
BAA37128.1|  Lactuca sativ    NEWRSIAPNLNTFVVNIGDTFMALSNGQYRSCLHRAVVNNKIHRKSLAFFLCPKKDKVVSPPD------ELVDEK
O04707 GAO1A_Triticum aes     GRWRSIRPRADAFVVNIGDTFMALSNGRYKSCLHRAVVNSRVPRKSLAFFLCPEMDKVVAPPG------TLVDAS
O04706 GAO1B_Triticum aes     GRWRSIRPRADAFVVNIGDTFMALSNGRYKSCLHRAVVNSKVPRKSLAFFLCPEMDKVVAPPG------TLVDAA O04705 GAO1D_Triticum aes     GRWRSIRPRADAFVVNIGDTFMALSNGRYKSCLHRAVVNSRVPRKSLAFFLCPEMDKVVAPPG------TLVDAA
P93771|GAOX1_Oryza sativa     GRWRAIRPRPGALVVNVGDTFMALSNARYRSCLHRAVVNSTAPRRSLAFFLCPEMDTVVRPPD------ELVDDH
Q8RVF5|GAOX2_Oryza sativa     GEWRPVSPVPGAMVINIGDTFMALSNGRYKSCLHRAVVNQRRERRSLAFFLCPREDRVVRPP--------PSAA
AAN73384.1|  Oryza rufipog    GEWRPVSPVPGAMVINIGDTFMALSNGRYKSCLHRAVVNQRRERRSLAFFLCPREDRVVRPP--------PSAA
AAF70814.1|  Sorghum bicol    GRWRSIRPHPGAFVVNIGDTFMAL-----------------------------------------------
AAG43043.1|  Lolium perenn    GRWLSIRPRADAFVVNIGDTFMALSNGRYKSCLHRAVVNSRVPRKSLAFFLCPEMDKVVAPPG------TLVDEA
AAG43045.1|  Lolium perenn    GRWLSIRPRADAFVVNIGDTFMALSNGRYKSCLHRAVVNSRVPRKSLAFFLCPEMDKVVAPPG------TLVDEA
AAG43044.1|  Lolium perenn    GRWLSIRPRADAFVVNIGDTFMALSNGRYKSCLHRAVVNSRVPRKSLAFFLCPEMDKVVAPPE------TLVDEA
AAG43042.1|  Lolium perenn    GRWLSIRPRADAFVVNIGDTFMALSNGRYKSCLHRAVVNSRVPRKSLAFFLCPEMDKVVAPPG------TSVDEA
ABG67710.1|  Zea mays         LAWRSVRPRPGAFVVNIGDTFMALSNGRYKSCLHRAVVNSRVARRSLAFFLCPEMDKVVRPPK------ELVDDA
ABG33927.1|  Zoysia japoni    GRWRSIRPHAGAFVVNIGDTFTGALQRPVPKLLHRAVVNSLVPRKSLAFFLCPEMDKVVCPPE------GLVEAG
ABF70102.1|  Musa balbisia    GKWQAVRPVRSAVVINIGDTFMALSNGRYKSCLHRAVVNSERERLSLAFFVCPRGDRVVRPPRELLLLLEEEEEA
```

TABLE 3-continued

Alignment of all protein sequences identified as plant GA20oxidases in one database. conserved sequences believed to be involved in substrate binding (binding to GA). Marked in light grey: conserved sequences believed to be involved in 2-oxoglutarate binding (co-substrate). Sequence fairly conserved within enzyme family 2-oxoglutarate dependent dixoygenases. Fe²⁺-binding motif, conserved in enzyme family 2-oxoglutarate dependent dioxygenases.

```
                             380       390       400       410       420       430       440
                         ....|....|....|....|....|....|....|....|....|....|....|....|....|
                                                                                        (SEQ ID NO: 1)
ABB00359.1| Fragaria x an    Y---PRIYPDFTWPMLLEFTQKHYRADMKTLQAFTNWLQ--EQRSS----------------
                                                                                        (SEQ ID NO: 2)
BAB20975.1| Malus x domes    S---PRKYPDFTWSMLLEFTMKHYRADMKTLQVFSNWVQ--QKSNQKL--------------
                                                                                        (SEQ ID NO: 3)
AAB64345.1| Cucurbita max    P---PRKYPDYKWPMLLEMTQKRYRPACNTLEAFKTWVQEGKALDTGSTITAPSA-------
                                                                                        (SEQ ID NO: 4)
CAA51744.1| Cucurbita max    P---PRKYPDYKWPMLLEMTQKRYRPDCNTLEAFKTWVQEGKALDTGSTITAPSA-------
                                                                                        (SEQ ID NO: 5)
CAC83626.1| Cucurbita max    N---PRRYPDFTWSMLLRFTQTHYRADMKTLEAFSAWLQ--QEQQEQQEQQFNI--------
                                                                                        (SEQ ID NO: 6)
CAA70329.1| Marah macroca    P---PRKFPDYTWPMLLEMTQKYYRADSNTFNAFTTWIQQQ-NLDS---TASPAV-------
                                                                                        (SEQ ID NO: 7)
AAD42693.1| Citrullus lan    P---PRKFPDYTWPMLLELTQKFYRADSNTFQAFIPWLEKQKSANT---IAPPAL-------
                                                                                        (SEQ ID NO: 8)
CAA17539.1| Arabidopsis t    ----RPAYRNFSFREFRQQVQEDVKKFGFKVGLPRFLNHVY---------------------
                                                                                        (SEQ ID NO: 9)
NP_176294.1| Arabidopsis     --G-ERAYPDFTWSMFLEFTMKHYRADMNTLEEFTNWLKNKGSF------------------
                                                                                        (SEQ ID NO: 10)
NP_175509.1| Arabidopsis     ----PKKYRRFSFREYKEQSEHDVKETGDKVGLSRFLI------------------------
                                                                                        (SEQ ID NO: 11)
Q39110|GAOX1_Arabidopsis     -IT-SRRYPDFTWSMFLEFTQKHYRADMNTLQAFSDWLTK---PI-----------------
                                                                                        (SEQ ID NO: 12)
Q39112|GAOX3_Arabidopsis     KSG-ERKYPDFTWSMFLEFTQKHYRADMNTLDEFSIWLKNRRSF------------------
                                                                                        (SEQ ID NO: 13)
Q39111|GAOX2_Arabidopsis     -MK-TRKYPDFTWSMFLEFTQKHYRADVNTLDSFSNWVITNNNPI-----------------
                                                                                        (SEQ ID NO: 14)
AAY98356.1| Sesbania rost    G---TKQYPDFTWSKLLEFTQKYYRADEDTLQNFTKWLLSSKPQTL----------------
                                                                                        (SEQ ID NO: 15)
AAC49721.1| Pisum sativum    T---PRIYPDFTWPMLLEFTQKHYRADMRTLEAFTKWIQ--QKQN-----------------
                                                                                        (SEQ ID NO: 16)
CAA62846.1| Pisum sativum    T---PRIYPDFTWPMLLEFTQKHYRADMRTLEAFTKWIQ--QKQN-----------------
                                                                                        (SEQ ID NO: 17)
AAB67838.1| Pisum sativum    N---PRKYPNFTWPSLLEFTQKHYRADERTLDAFSMWLQ--EKTTT----------------
                                                                                        (SEQ ID NO: 18)
CAD21845.1| Fagus sylvati    --------------------------------------------------------------
                                                                                        (SEQ ID NO: 19)
CAD21846.1| Fagus sylvati    C---PRVYPDFTWPMLLEFTQKHYRADVKTLEVFSNWLQ--QKNS-----------------
                                                                                        (SEQ ID NO: 20)
AAC49756.1| Phaseolus vul    C---PRVYPDFTWPMLLEFTQKHYRADMKTLEAFTNWLQ--QKRS-----------------
                                                                                        (SEQ ID NO: 21)
AAC49758.1| Phaseolus vul    N---PKKYPDFTWPNLLEFTQLHYRSDPETLDAFANWVL--EKNK-----------------
                                                                                        (SEQ ID NO: 22)
AAC49757.1| Phaseolus vul    S---PRLYPDFTWPMLLEFTQKHYRADMKTLEAFTNWLQ--RRSNFDNHIM-----------
                                                                                        (SEQ ID NO: 23)
AAW80969.1| Gossypium hir    N---SRKYPDFTWAALLEFTQNHYRADMKTLVAFSKWVQ--EQESNNKLIP-----------
                                                                                        (SEQ ID NO: 24)
AAT28326.1| Gossypium hir    N---PRKYPDFTWAALLKFTQNHYRADMKTLVAFSKWVQ--EQESNYKLIP-----------
                                                                                        (SEQ ID NO: 25)
ABA01489.1| Gossypium hir    N---PRKYPDFTWAALLKFTQNHYRADMKTLVAFSKWVQ--EQESNYKLIP-----------
                                                                                        (SEQ ID NO: 26)
BAD90753.1| Ipomoea nil      H---PKLYPDFKWPALLEYTQLHYRSDTDTLLNFATWLQQNQTLHATQA-------------
                                                                                        (SEQ ID NO: 27)
BAD90752.1| Ipomoea nil      H---PRLYPDFKWPTLLEFTQKHYRSDTDTLLSFSAWLQQNQTPHATHP-------------
                                                                                        (SEQ ID NO: 28)
BAA32156.1| Nicotiana tab    N---PRIYPDFTWPTLLEFTQKHYRADMNTLQTFSNWL---KQKTAQV--------------
                                                                                        (SEQ ID NO: 29)
AAT39975.1| Solanum demis    N---PRIYPDFTWPTLLEFTQKQYRADMNTLQTFSNWL---KKTHP----------------
                                                                                        (SEQ ID NO: 30)
CAB82616.1| Solanum dulca    N---PRIYPDFTWPTLLEFTQKHYRADMNTLQTFSNWL--QHNTTAQL--------------
                                                                                        (SEQ ID NO: 31)
CAB82617.1| Solanum dulca    N---PRIYPDFTWPDLLEFTQKQYRADMNTLQTFSIWL---QKTQV----------------
                                                                                        (SEQ ID NO: 32)
CAC13038.1| Solanum tuber    N---PRIYPDFTWPTLLEFTQKQYRADMNTLQTFSNWL---KKTHP----------------
                                                                                        (SEQ ID NO: 33)
CAC13037.1| Solanum tuber    N---PRIYPDFTWPTLLEFTQKHYRADTNTLQFFSNWL---QQRTTEV--------------
                                                                                        (SEQ ID NO: 34)
CAC13036.1| Solanum tuber    N---PRIYPDFTWPTLLEFTQKHYRADMNTLQTFSNWVHDQHNTKTQV--------------
                                                                                        (SEQ ID NO: 35)
BAB32733.1| Eustoma grand    --------------------------------------------------------------
                                                                                        (SEQ ID NO: 36)
CAB96202.1| Citrus sinens    S--SPRIYPDFTWPMLLEFTQKHYRADMKTLEAFTNWLQ--QKKQLK---------------
                                                                                        (SEQ ID NO: 37)
AAC49211.1| Spinacia ole     ----PRVYPDFTWPLLLEFTQKHYRADTKTLDSFTKWLQ--KRSTEDERVK-----------
                                                                                        (SEQ ID NO: 38)
ABF61826.1| Vitis vinifer    S---PRIYPDFTWSNLLEFTQKHYRADMKTLEVFSSWLQ--QKTAEAG--------------
```

TABLE 3-continued

Alignment of all protein sequences identified as plant GA20oxidases in one database. [dark grey] conserved sequences believed to be involved in substrate binding (binding to GA). Marked in light grey: conserved sequences believed to be involved in 2-oxoglutarate binding (co-substrate). Sequence fairly conserved within enzyme family 2-oxoglutarate dependent dixoygenases. [marked in grey] $Fe^{2+}$-binding motif, conserved in enzyme family 2-oxoglutarate dependent dioxygenases.

```
                                                                              (SEQ ID NO: 39)
CAC00709.1| Populus tremu    N---PRIYPDFTWPMLLEFTQKHYRADMKTLEVFTNWLH--QRSFS----------------------
                                                                              (SEQ ID NO: 40)
AAT02537.1| Populus tomen    N---PRIYPDFTWPMLLEFTQKHYRADMKTLEVFTNWLH--QRSFT----------------------
                                                                              (SEQ ID NO: 41)
BAC56963.1| Populus nigra    N---PRIYPDFTWPMLLEFTQKHYRADMKTLEVFTNWLH--QQSFS----------------------
                                                                              (SEQ ID NO: 42)
CAH59142.1| Populus tremu    N---PRIYPDFTWPMLLEFTQKHYRADMKTLEVFTNWLH--QRSFS----------------------
                                                                              (SEQ ID NO: 43)
CAH59140.1| Populus tremu    N---PRIYPDFTWPMLLEFTQKHYRADMKTLEVFTNWLH--QRSFS----------------------
                                                                              (SEQ ID NO: 44)
CAH59139.1| Populus tremu    N---PRIYPDFTWPMLLEFTQKHYRADMKTLEVFTNWLH--QRSFS----------------------
                                                                              (SEQ ID NO: 45)
CAH59138.1| Populus tremu    D---PRIYPDFTWPMLLEFTQKHYRADMKTLEVFTNWLH--QRSFS----------------------
                                                                              (SEQ ID NO: 46)
CAH59136.1| Populus tremu    N---PRIYPDFTWPMLLEFTQKHYRADMKTLEVFTNWLH--QRSFS----------------------
                                                                              (SEQ ID NO: 47)
CAH59135.1| Populus tremu    N---PRIYPDFTWPMLLEFTQKHYRADMKTLEVFTNWLH--QRSFS----------------------
                                                                              (SEQ ID NO: 48)
CAH59134.1| Populus tremu    N---PRIYPDFTWPMLLEFTQKHYRADMKTLEVFTNWLH--QRSFS----------------------
                                                                              (SEQ ID NO: 49)
CAH59133.1| Populus tremu    N---PRIYPDFTWPMLLEFTQKHYRADMKTLEVFTNWLH--QRSFS----------------------
                                                                              (SEQ ID NO: 50)
CAH59132.1| Populus tremu    N---PRIYPDFTWPMLLEFTQKHYRADMKTLEVFTNWLH--QRSLS----------------------
                                                                              (SEQ ID NO: 51)
CAH59131.1| Populus tremu    N---PRIYPDFTWPMLLEFTQKHYRADMKTLEVFTNWLH--QRSFS----------------------
                                                                              (SEQ ID NO: 52)
CAH59130.1| Populus tremu    N---PRIYPDFTWPMLLEFTQKHYRADMKTLEVFTNWLH--QRSLS----------------------
                                                                              (SEQ ID NO: 53)
CAH59128.1| Populus tremu    N---PRIYPDFTWPMLLEFTQKHYRADMKTLEVFTNWLH--QRSLS----------------------
                                                                              (SEQ ID NO: 54)
BAC82104.1| Populus alba     N---PRIYPDFTWPMLLEFTQKHYRADMKTLEVFTNWLH--QRSLS----------------------
                                                                              (SEQ ID NO: 55)
BAC82102.1| Populus alba     N---PRIYPDFTWPMLLEFTQKHYRADMKTLEVFTNWLH--QRSLS----------------------
                                                                              (SEQ ID NO: 56)
BAA37128.1| Lactuca sativ    N---PRIYPDFTWSTFLEFTQKHYRADMNTLQAFTNWI---QQKNS----------------------
                                                                              (SEQ ID NO: 57)
O04707 GAO1A_Triticum aes    N---PRAYPDFTWRSLLDFTQKHYRADMKTLEVFSSWIVQQQQGQLALQPAMT----------------
                                                                              (SEQ ID NO: 58)
O04706 GAO1B_Triticum aes    N---PRAYPDFTWRSLLDFTQKHYRADMKTLEVFSSWIVQQQQGQLLPPLASH----------------
                                                                              (SEQ ID NO: 59)
O04705|GAO1D_Triticum aes    N---PRAYPDFTWRSLLDFTQKHYRADMKTLEVFSSWIVQQQQ----PQPART----------------
                                                                              (SEQ ID NO: 60)
P93771|GAOX1_Oryza sativa    H---PRVYPDFTWRALLDFTQRHYRADMRLFQAFSDWLNHHRHLQPTIYS-------------------
                                                                              (SEQ ID NO: 61)
Q8RVF5|GAOX2_Oryza sativa    T---PQHYPDFTWADLMRFTQRHYRADTRTLDAFTRWLAPPAADAAATAQVEAAS--------------
                                                                              (SEQ ID NO: 62)
AAN73384.1| Oryza rufipog    T---PRHYPDFTWADLMRFTQRHYRADTRTLDAFTRWLAPPAADAAATAQVEAAS--------------
                                                                              (SEQ ID NO: 63)
AAF70814.1| Sorghum bicol    ---------------------------------------------------------------------
                                                                              (SEQ ID NO: 64)
AAG43043.1| Lolium perenn    N---PRAYPDFTWRALLDFTQKHYRADMKTLEVFSDWIQQGHQPAATTTTT------------------
                                                                              (SEQ ID NO: 65)
AAG43045.1| Lolium perenn    N---PRAYPDFTWRALLDFTQKHYRADMKTLEVFSDWIQQGHQPAATTTTT------------------
                                                                              (SEQ ID NO: 66)
AAG43044.1| Lolium perenn    N---PRAYPDFTWRALLDFTQKHYRADMKTLEVFSDWIQQGHQPAATTTTT------------------
                                                                              (SEQ ID NO: 67)
AAG43042.1| Lolium perenn    N---PRAYPDFTWRALLDFTQKHYRADMKTLEVFSDWIQQGHQPAATTTTTQDQRTYTASASLHLLACCT
                                                                              (SEQ ID NO: 68)
ABG67710.1| Zea mays         N---PRAYPDFTWRTLLDFTMRHYRSDMRTLEAFSNWLST--RSNGGQHLLEKK----------------
                                                                              (SEQ ID NO: 69)
ABG33927.1| Zoysia japoni    M---PRAYPDFTWRTLLDFTQRRYRADMRTLEVFSNWLRHGQDKTPPTLSIHRSKIVTVHHPS-------
                                                                              (SEQ ID NO: 70)
ABF70102.1| Musa balbisia    V---PRAFPDFTWTELLEFTQTHYRADTTTLQSFSRHRFLASSP-------------------------
```

We claim:

1. A transgenic *Populus* plant comprising a heterologous nucleic acid molecule encoding a GA 20-oxidase, the nucleic acid molecule operably linked to a promoter, wherein expression of the nucleic acid molecule in the *Populus* plant results in increased xylem fibre length, wherein the GA 20-oxidase exhibits at least 70% amino acid identity to SEQ ID NO:39.

2. The transgenic *Populus* plant according to claim 1, wherein the transgenic *Populus* plant is a *Populus tremula×P. tremuloides* species.

3. A transgenic *Populus* plant comprising a heterologous nucleic acid molecule encoding a GA 20-oxidase, the nucleic acid molecule operably linked to a promoter, wherein expression of the nucleic acid molecule in the *Populus* plant results in increased xylem fibre length, wherein the GA 20-oxidase exhibits at least 70% amino acid identity to SEQ ID NO:39, and wherein the polypeptide comprises three motifs in the following order from N-terminal to C-terminal: LPWKET (SEQ ID NO: 71), NYYP (SEQ ID NO: 72), and HXD (SEQ ID NO: 73).

4. The transgenic *Populus* plant according to claim 3, wherein the transgenic *Populus* plant is a *Populus tremula×P. tremuloides* species.

5. The transgenic *Populus* plant according to claim 3, wherein the GA 20-oxidase has at least 80% amino acid identity to SEQ ID NO: 39.

6. The transgenic *Populus* plant according to claim 3, wherein the GA 20-oxidase has at least 90% amino acid identity to SEQ ID NO: 39.

7. The transgenic *Populus* plant according to claim 3, wherein the GA 20-oxidase has at least 95% amino acid identity to SEQ ID NO: 39.

8. The transgenic *Populus* plant according to claim 3, wherein the GA 20-oxidase has at least 99% amino acid identity to SEQ ID NO: 39.

9. A transgenic seed that produces a *Populus* plant comprising a heterologous nucleic acid molecule encoding a GA 20-oxidase, the nucleic acid molecule operably linked to a promoter, wherein expression of the nucleic acid molecule in the *Populus* plant results in increased xylem fibre length, wherein the GA 20-oxidase exhibits at least 70% amino acid identity to SEQ ID NO:39.

10. A transgenic cell derived from the transgenic *Populus* plant of claim 1, wherein the cell comprises the nucleic acid molecule.

11. A transgenic cell derived from the transgenic *Populus* plant of claim 3, wherein the cell comprises the nucleic acid molecule.

12. A transgenic, propagating material derived from the transgenic *Populus* plant of claim 1, wherein the propagating material comprises the nucleic acid molecule.

13. A transgenic, propagating material derived from the transgenic *Populus* plant of claim 3, wherein the propagating material comprises the nucleic acid molecule.

14. A method of increasing xylem fibre length in a *Populus* tree comprising introducing a heterologous nucleic acid molecule encoding a GA 20-oxidase into the *Populus* tree's genome, wherein the nucleic acid molecule is operably linked to a promoter, wherein expression of the nucleic acid molecule in the *Populus* tree results in increased xylem fibre length, and wherein the GA 20-oxidase exhibits at least 70% amino acid identity to SEQ ID NO:39.

15. The transgenic *Populus* plant according to claim 1, wherein the nucleic acid molecule is DNA.

16. The transgenic *Populus* plant according to claim 1, wherein the GA 20-oxidase has at least 80% amino acid identity to SEQ ID NO: 39.

17. The transgenic *Populus* plant according to claim 1, wherein the GA 20-oxidase has at least 90% amino acid identity to SEQ ID NO: 39.

18. The transgenic *Populus* plant according to claim 1, wherein the GA 20-oxidase has at least 95% amino acid identity to SEQ ID NO: 39.

19. The transgenic *Populus* plant according to claim 1, wherein the GA 20-oxidase has at least 99% amino acid identity to SEQ ID NO: 39.

20. The transgenic *Populus* plant according to claim 1, wherein the GA 20-oxidase is SEQ ID NO: 39.

21. The transgenic *Populus* plant according to claim 1, wherein the GA 20-oxidase comprises three motifs in the following order from N-terminal to C-terminal: LPWKET (SEQ ID NO: 71), NYYP (SEQ ID NO: 72), and HXD (SEQ ID NO: 73).

22. The transgenic *Populus* plant according to claim 3, wherein the nucleic acid molecule is DNA.

23. The transgenic *Populus* plant according to claim 3, wherein the GA 20-oxidase is SEQ ID NO: 39.

\* \* \* \* \*

UNITED STATES PATENT AND TRADEMARK OFFICE
CERTIFICATE OF CORRECTION

| | | |
|---|---|---|
| PATENT NO. | : 7,807,878 B2 | |
| APPLICATION NO. | : 11/590211 | |
| DATED | : October 5, 2010 | |
| INVENTOR(S) | : Maria Eriksson et al. | |

Page 1 of 1

It is certified that error appears in the above-identified patent and that said Letters Patent is hereby corrected as shown below:

On the front page, in the section entitled "(75) Inventors:", change the fourth inventor's name from "Oloff Olsson" to --Olof Olsson--, therefor.

Signed and Sealed this
Twenty-eighth Day of December, 2010

David J. Kappos
*Director of the United States Patent and Trademark Office*